United States Patent
Kooij et al.

(10) Patent No.: US 10,245,404 B2
(45) Date of Patent: Apr. 2, 2019

(54) PATIENT INTERFACE SYSTEMS

(71) Applicant: ResMed Limited, Bella Vista, New South Wales (AU)

(72) Inventors: Michiel Kooij, Sydney (AU); Scott Alexander Howard, Sydney (AU); Justin John Formica, Sydney (AU); Gerard Michael Rummery, Woodford (AU); Renee Frances Flower, Sydney (AU); Adam Francis Barlow, Sydney (AU); Joel Edward Gibson, Sydney (AU); Damien Julian Mazzone, Sydney (AU); Aaron Samuel Davidson, Sydney (AU); Bernd Christoph Lang, Graefelfing (DE); Achim Biener, Aufkirchen (DE); Michael John Reid, Sydney (AU); Dieter Heidmann, Geretsried (DE)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 14/810,525

(22) Filed: Jul. 28, 2015

(65) Prior Publication Data
US 2015/0328425 A1 Nov. 19, 2015

Related U.S. Application Data

(60) Continuation of application No. 13/619,512, filed on Sep. 14, 2012, now Pat. No. 9,149,594, which is a
(Continued)

(51) Int. Cl.
*A61M 16/06* (2006.01)
*A61M 16/08* (2006.01)

(52) U.S. Cl.
CPC .... *A61M 16/0666* (2013.01); *A61M 16/0611* (2014.02); *A61M 16/0616* (2014.02);
(Continued)

(58) Field of Classification Search
CPC .......... A61M 16/0683; A61M 16/0688; A61M 16/0694
(Continued)

(56) References Cited

U.S. PATENT DOCUMENTS

| | | |
|---|---|---|
| 443,191 A | 12/1890 | Illing |
| 781,516 A | 1/1905 | Guthrie, Jr. |

(Continued)

FOREIGN PATENT DOCUMENTS

| | | |
|---|---|---|
| AU | 199651130 | 10/1996 |
| AU | 2005100738 | 11/2005 |

(Continued)

OTHER PUBLICATIONS

Notice of Reasons for Rejection dated Aug. 1, 2016 issued in Japanese Application No. 2015-185135 with English translation (34 pages).
(Continued)

*Primary Examiner* — (Jackie) Tan-Uyen T Ho
*Assistant Examiner* — Joseph D Boecker
(74) *Attorney, Agent, or Firm* — Nixon & Vanderhye P.C.

(57) ABSTRACT

A patient interface system for delivering a flow of breathable gas to a patient includes a patient interface structure configured to sealingly engage the face of the patient and a retaining element configured for application to the patient. The retaining element is configured to support the patient interface structure in sealing engagement with the face of the patient. The retaining element includes an adhesive and/or at least one strap. In addition, the patient interface structure is configured to be released from and re-engaged with the retaining element for re-positioning of the patient interface structure relative to the patient's face in a plurality of positions while the retaining element remains supported by the patient.

11 Claims, 56 Drawing Sheets

Related U.S. Application Data division of application No. 12/478,537, filed on Jun. 4, 2009, now Pat. No. 8,291,906.

(60) Provisional application No. 61/058,659, filed on Jun. 4, 2008, provisional application No. 61/080,847, filed on Jul. 15, 2008.

(52) U.S. Cl.
CPC .... *A61M 16/0683* (2013.01); *A61M 16/0688* (2014.02); *A61M 16/0633* (2014.02); *A61M 16/0825* (2014.02); *A61M 16/0875* (2013.01)

(58) Field of Classification Search
USPC ............. 128/206.14, 206.25, 207.11, 207.17
See application file for complete search history.

(56) References Cited

U.S. PATENT DOCUMENTS

| | | | |
|---|---|---|---|
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,357,426 A | 12/1967 | Cohen |
| 3,670,726 A | 3/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 11/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 11/1986 | Chu et al. |
| 4,630,604 A | 12/1986 | Montesi |
| 4,641,647 A | 2/1987 | Behan |
| 4,648,398 A | 3/1987 | Agdanowski et al. |
| 4,660,555 A * | 4/1987 | Payton .............. A61M 16/0488 |
| | | 128/207.18 |
| 4,665,566 A * | 5/1987 | Garrow ............ A61M 16/0666 |
| | | 128/201.22 |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 11/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,304,146 A | 4/1994 | Johnson et al. |
| 5,299,599 A | 5/1994 | Farmer et al. |
| 5,320,092 A | 6/1994 | Ryder |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |

(56) References Cited

U.S. PATENT DOCUMENTS

| | | | |
|---|---|---|---|
| 5,396,885 A | 3/1995 | Nelson | |
| 5,398,676 A | 3/1995 | Press et al. | |
| 5,400,776 A | 3/1995 | Bartholomew | |
| 5,419,318 A | 5/1995 | Tayebi | |
| 5,425,359 A | 6/1995 | Liou | |
| 5,429,683 A | 7/1995 | Le Mitouard | |
| 5,437,267 A | 8/1995 | Weinstein et al. | |
| 5,441,046 A | 8/1995 | Starr et al. | |
| 5,462,528 A | 10/1995 | Roewer | |
| 5,477,852 A | 12/1995 | Landis et al. | |
| 5,488,948 A | 2/1996 | Dubruille et al. | |
| 5,509,409 A * | 4/1996 | Weatherholt | A61M 16/0666 128/200.26 |
| 5,513,634 A | 5/1996 | Jackson | |
| 5,513,635 A | 5/1996 | Bedi | |
| 5,526,806 A * | 6/1996 | Sansoni | A61M 16/0666 128/206.11 |
| 5,533,506 A | 7/1996 | Wood | |
| 5,538,000 A | 7/1996 | Rudolph | |
| 5,538,001 A | 7/1996 | Bridges | |
| 5,560,354 A | 10/1996 | Berthon-Jones et al. | |
| 5,570,684 A | 11/1996 | Behr | |
| 5,592,938 A | 1/1997 | Scarberry et al. | |
| 5,623,923 A | 4/1997 | Bertheau et al. | |
| 5,647,357 A | 7/1997 | Barnett et al. | |
| 5,653,224 A | 8/1997 | Johnson | |
| 5,653,228 A | 8/1997 | Byrd | |
| 5,655,527 A | 8/1997 | Scarberry et al. | |
| 5,662,101 A | 9/1997 | Ogden et al. | |
| 5,669,377 A | 9/1997 | Fenn | |
| 5,682,881 A | 11/1997 | Winthrop et al. | |
| 5,704,345 A | 1/1998 | Berthon-Jones et al. | |
| 5,704,916 A * | 1/1998 | Byrd | A61M 25/02 128/207.17 |
| 5,707,342 A | 1/1998 | Tanaka | |
| 5,724,965 A | 3/1998 | Handke et al. | |
| 5,727,544 A * | 3/1998 | Miura | A41D 13/11 128/201.13 |
| 5,735,272 A * | 4/1998 | Dillon | A61F 5/08 128/207.18 |
| 5,740,799 A | 4/1998 | Nielson | |
| 5,752,511 A | 5/1998 | Simmons et al. | |
| 5,794,619 A | 8/1998 | Edeiman et al. | |
| 5,803,066 A * | 9/1998 | Rapoport | A61B 5/0002 128/204.21 |
| 5,807,341 A | 9/1998 | Heim | |
| 5,842,469 A | 12/1998 | Rapp et al. | |
| 5,906,203 A | 5/1999 | Klockseth et al. | |
| 5,918,598 A | 7/1999 | Belfer et al. | |
| 5,921,239 A | 7/1999 | McCall et al. | |
| 5,931,854 A | 8/1999 | Dillon | |
| 5,954,049 A | 9/1999 | Foley et al. | |
| 5,975,079 A | 11/1999 | Hellings et al. | |
| 5,976,173 A * | 11/1999 | Berke | A61F 5/08 128/858 |
| 6,019,101 A | 1/2000 | Cotner et al. | |
| 6,026,811 A | 2/2000 | Settle | |
| 6,044,844 A | 4/2000 | Kwok et al. | |
| 6,050,260 A | 4/2000 | Daniell et al. | |
| 6,082,360 A | 7/2000 | Rudolph et al. | |
| 6,086,118 A | 7/2000 | McNaughton et al. | |
| 6,093,169 A * | 7/2000 | Cardoso | A61M 16/0666 128/207.18 |
| 6,095,996 A | 8/2000 | Steer et al. | |
| 6,098,205 A | 8/2000 | Schwartz et al. | |
| 6,109,263 A | 8/2000 | Feuchtgruber | |
| 6,112,746 A | 9/2000 | Kwok et al. | |
| 6,119,693 A | 9/2000 | Kwok et al. | |
| 6,119,694 A | 9/2000 | Correa et al. | |
| 6,123,071 A | 9/2000 | Berthon-Jones et al. | |
| 6,123,082 A | 9/2000 | Berthon-Jones | |
| 6,139,787 A | 10/2000 | Harrison | |
| 6,152,137 A | 11/2000 | Schwartz et al. | |
| 6,193,914 B1 | 2/2001 | Harrison | |
| 6,196,223 B1 * | 3/2001 | Belfer | A41D 13/1176 128/205.25 |
| 6,211,263 B1 | 4/2001 | Cinelli et al. | |
| 6,231,548 B1 | 5/2001 | Bassett | |
| 6,241,930 B1 | 6/2001 | Harrison | |
| 6,258,066 B1 | 7/2001 | Urich | |
| 6,295,366 B1 | 9/2001 | Haller et al. | |
| 6,328,038 B1 | 12/2001 | Kessler et al. | |
| 6,341,606 B1 | 1/2002 | Bordewick et al. | |
| 6,347,631 B1 | 2/2002 | Hansen et al. | |
| 6,357,441 B1 | 3/2002 | Kwok et al. | |
| 6,358,279 B1 | 3/2002 | Tahi et al. | |
| 6,374,826 B1 | 4/2002 | Gunaratnam et al. | |
| 6,412,487 B1 | 7/2002 | Gunaratnam et al. | |
| 6,412,488 B1 | 7/2002 | Barnett et al. | |
| 6,412,593 B1 | 7/2002 | Jones | |
| 6,419,660 B1 | 7/2002 | Russo | |
| 6,422,238 B1 | 7/2002 | Lithgow | |
| 6,423,036 B1 | 7/2002 | Van Huizen | |
| 6,431,172 B1 | 8/2002 | Bordewick | |
| 6,434,796 B1 | 8/2002 | Speirs | |
| 6,439,234 B1 | 8/2002 | Curti et al. | |
| 6,448,303 B1 | 9/2002 | Paul | |
| 6,467,482 B1 | 10/2002 | Boussignac | |
| 6,467,483 B1 | 10/2002 | Kopacko et al. | |
| 6,470,886 B1 | 10/2002 | Jestrabek-Hart | |
| 6,470,887 B1 | 10/2002 | Martinez | |
| 6,478,026 B1 | 11/2002 | Wood | |
| 6,482,178 B1 | 11/2002 | Andrews et al. | |
| 6,491,034 B1 | 12/2002 | Gunaratnam et al. | |
| 6,513,526 B2 | 2/2003 | Kwok et al. | |
| 6,530,373 B1 | 3/2003 | Patron et al. | |
| 6,532,961 B1 | 3/2003 | Kwok et al. | |
| 6,536,435 B1 | 3/2003 | Fecteau et al. | |
| 6,536,436 B1 | 3/2003 | McGlothen | |
| 6,561,188 B1 | 5/2003 | Ellis | |
| 6,561,190 B1 | 5/2003 | Kwok et al. | |
| 6,561,192 B2 | 5/2003 | Palmer | |
| 6,561,193 B1 | 5/2003 | Noble | |
| 6,571,798 B1 | 6/2003 | Thornton | |
| 6,579,267 B2 | 6/2003 | Lynch et al. | |
| 6,581,601 B2 | 6/2003 | Ziaee | |
| 6,581,602 B2 | 6/2003 | Kwok et al. | |
| 6,584,975 B1 | 7/2003 | Taylor | |
| 6,595,214 B1 | 7/2003 | Hecker et al. | |
| 6,595,215 B2 | 7/2003 | Wood | |
| 6,607,516 B2 | 8/2003 | Cinelli et al. | |
| 6,627,289 B1 | 9/2003 | Dilnik et al. | |
| 6,631,718 B1 | 10/2003 | Lovell | |
| 6,634,358 B2 | 10/2003 | Kwok et al. | |
| 6,637,434 B2 | 10/2003 | Noble | |
| 6,644,315 B2 | 11/2003 | Ziaee | |
| 6,655,385 B1 | 12/2003 | Curti et al. | |
| 6,663,600 B2 | 12/2003 | Bierman et al. | |
| 6,669,712 B1 | 12/2003 | Cardoso | |
| D485,905 S | 1/2004 | Moore et al. | |
| 6,679,257 B1 | 1/2004 | Robertson et al. | |
| 6,679,265 B2 | 1/2004 | Strickland et al. | |
| 6,701,927 B2 | 3/2004 | Kwok et al. | |
| 6,710,099 B2 | 3/2004 | Cinelli et al. | |
| 6,766,800 B2 | 7/2004 | Chu et al. | |
| 6,766,817 B2 | 7/2004 | da Silva | |
| 6,776,162 B2 | 8/2004 | Wood | |
| 6,776,163 B2 | 8/2004 | Dougill et al. | |
| 6,789,543 B2 | 9/2004 | Cannon | |
| 6,805,117 B1 * | 10/2004 | Ho | A61M 16/0633 128/201.22 |
| 6,807,967 B2 | 10/2004 | Wood | |
| 6,817,362 B2 | 11/2004 | Gelinas et al. | |
| 6,820,617 B2 | 11/2004 | Robertson et al. | |
| 6,823,865 B2 | 11/2004 | Drew et al. | |
| 6,823,869 B2 | 11/2004 | Raje et al. | |
| 6,834,650 B1 | 12/2004 | Fini | |
| 6,860,270 B2 | 3/2005 | Sniadach | |
| 6,895,965 B2 | 5/2005 | Scarberry et al. | |
| 6,907,882 B2 | 6/2005 | Ging et al. | |
| 6,918,404 B2 | 7/2005 | Dias da Silva | |
| 6,926,004 B2 | 8/2005 | Schumacher | |
| 6,938,620 B2 | 9/2005 | Payne, Jr. | |

(56) References Cited

U.S. PATENT DOCUMENTS

| | | |
|---|---|---|
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,077,140 B1* | 7/2006 | Berke ............. A41D 13/1176 128/200.18 |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,156,097 B2 | 1/2007 | Cardoso |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,237,551 B2 | 7/2007 | Ho et al. |
| 7,243,723 B2 | 7/2007 | Surjaatmadja |
| 7,255,107 B1 | 8/2007 | Gomez |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,331,348 B1 | 2/2008 | Beevers |
| 7,523,754 B2 | 4/2009 | Lithgow |
| 7,658,189 B2 | 2/2010 | Davidson |
| 7,902,420 B2 | 3/2011 | Kase |
| 8,291,906 B2 | 10/2012 | Kooij et al. |
| 8,714,158 B2* | 5/2014 | Hernandez ........... A61M 16/06 128/206.24 |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | Devoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0117177 A1 | 8/2002 | Kwok |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1* | 12/2002 | Bishop ............... A41D 13/1176 128/206.25 |
| 2003/0000526 A1 | 1/2003 | Goebel |
| 2003/0019495 A1 | 1/2003 | Palkon et al. |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0172936 A1 | 9/2003 | Wilkie et al. |
| 2003/0196656 A1 | 10/2003 | Moore et al. |
| 2003/0196658 A1 | 10/2003 | Ging et al. |
| 2003/0209246 A1 | 11/2003 | Schroeder et al. |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0045553 A1 | 3/2004 | Cardoso |
| 2004/0065328 A1 | 4/2004 | Amarasinghe et al. |
| 2004/0083534 A1 | 5/2004 | Ruiz et al. |
| 2004/0106891 A1 | 6/2004 | Langan et al. |
| 2004/0111104 A1 | 6/2004 | Schein et al. |
| 2004/0112377 A1* | 6/2004 | Amarasinghe .... A61M 16/0683 128/201.22 |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0200476 A1 | 10/2004 | Bamford |
| 2004/0211428 A1 | 10/2004 | Jones |
| 2004/0226564 A1 | 11/2004 | Persson |
| 2004/0226566 A1 | 11/2004 | Gunaratnam et al. |
| 2004/0244799 A1* | 12/2004 | Landis .............. A61M 16/0683 128/206.21 |
| 2004/0245658 A1 | 12/2004 | Niland et al. |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0034730 A1 | 2/2005 | Wood |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0066976 A1* | 3/2005 | Wondka ............... A61M 16/06 128/207.18 |
| 2005/0098183 A1* | 5/2005 | Nash ................... A61M 16/06 128/206.21 |
| 2005/0101933 A1 | 5/2005 | Marrs et al. |
| 2005/0103346 A1 | 5/2005 | Noble |
| 2005/0150495 A1 | 7/2005 | Rittner et al. |
| 2005/0155604 A1 | 7/2005 | Ging et al. |
| 2005/0199242 A1* | 9/2005 | Matula, Jr. ........... A61M 16/06 128/207.13 |
| 2005/0211252 A1 | 9/2005 | Lang et al. |
| 2005/0241644 A1 | 11/2005 | Gunaratnam et al. |
| 2005/0284481 A1 | 12/2005 | Meyer |
| 2006/0028346 A1 | 2/2006 | White |
| 2006/0060200 A1 | 3/2006 | Ho et al. |
| 2006/0081250 A1 | 4/2006 | Bordewick et al. |
| 2006/0081256 A1 | 4/2006 | Palmer |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1* | 10/2006 | Davidson ............ A61M 16/06 128/205.25 |
| 2006/0283461 A1 | 12/2006 | Lubke et al. |
| 2007/0023044 A1 | 2/2007 | Kwok et al. |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0277832 A1 | 12/2007 | Doshi et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0041373 A1 | 2/2008 | Doshi et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0105257 A1 | 5/2008 | Klasek et al. |
| 2008/0110469 A1 | 5/2008 | Weinberg |
| 2008/0190436 A1* | 8/2008 | Jaffe ................. A61M 16/0666 128/207.18 |
| 2008/0200880 A1 | 8/2008 | Kyvik et al. |
| 2008/0257354 A1 | 10/2008 | Davidson et al. |
| 2008/0295835 A1* | 12/2008 | Han ................... A61M 16/0683 128/204.18 |
| 2008/0295846 A1* | 12/2008 | Han ..................... A61M 16/06 128/207.13 |
| 2008/0302365 A1* | 12/2008 | Cohen ................. A61M 16/06 128/206.12 |
| 2009/0044808 A1 | 2/2009 | Guney et al. |
| 2009/0078259 A1 | 3/2009 | Kooij et al. |
| 2009/0223514 A1 | 9/2009 | Smith et al. |
| 2010/0000534 A1 | 1/2010 | Kooij et al. |
| 2010/0018534 A1 | 1/2010 | Veliss et al. |
| 2010/0229872 A1* | 9/2010 | Ho ..................... A61M 16/06 128/206.25 |

(56) References Cited

U.S. PATENT DOCUMENTS

| | | | |
|---|---|---|---|
| 2010/0307502 A1 | 12/2010 | Rummery et al. | |
| 2013/0032154 A1 | 2/2013 | Kooij et al. | |
| 2014/0238407 A1 | 8/2014 | Ho | |

FOREIGN PATENT DOCUMENTS

| | | | |
|---|---|---|---|
| CN | 1217179 A | 5/1999 | |
| CN | 1280477 A | 1/2001 | |
| CN | 1450866 A | 10/2003 | |
| CN | 1784250 A | 6/2006 | |
| CN | 101287515 A | 10/2008 | |
| DE | 185017 | 5/1907 | |
| DE | 30 11 900 | 10/1980 | |
| DE | 146 688 | 2/1981 | |
| DE | 37 19 009 | 12/1988 | |
| DE | 39 27 038 | 2/1991 | |
| DE | 297 23 101 | 7/1998 | |
| DE | 197 03 526 A1 | 8/1998 | |
| DE | 199 44 242 | 3/2001 | |
| DE | 100 02 571 | 7/2001 | |
| DE | 102 13 905 | 10/2002 | |
| DE | 10 2004 055 433 | 11/2004 | |
| DE | 10 2006 016 125 A1 | 10/2007 | |
| EP | 0 288 937 | 11/1988 | |
| EP | 0 427 474 | 5/1991 | |
| EP | 0 466 960 A1 | 1/1992 | |
| EP | 0 303 090 | 4/1992 | |
| EP | 0 658 356 | 6/1995 | |
| EP | 0 776 679 A1 | 6/1997 | |
| EP | 0845278 | 6/1998 | |
| EP | 1 099 452 | 5/2001 | |
| EP | 1 258 266 | 11/2002 | |
| EP | 1 481 702 | 12/2004 | |
| FR | 2 720 280 | 12/1995 | |
| GB | 532214 | 1/1941 | |
| GB | 2 176 404 | 12/1986 | |
| GB | 2 368 533 | 5/2002 | |
| GB | 2 385 533 | 8/2003 | |
| JP | 61-276566 | 12/1986 | |
| JP | 2002-543936 | 12/2002 | |
| JP | 2005-87766 | 4/2005 | |
| JP | 2005-304574 A | 11/2005 | |
| JP | 2007-516750 | 6/2007 | |
| JP | 2008-522763 | 7/2008 | |
| JP | 2008-200061 | 9/2008 | |
| JP | 2009-502429 | 1/2009 | |
| JP | 2009-545408 | 12/2009 | |
| WO | WO 1982/003548 | 10/1982 | |
| WO | WO 1987/001950 | 4/1987 | |
| WO | WO 1992/020392 | 11/1992 | |
| WO | WO 1992/020395 | 11/1992 | |
| WO | WO 1996/028207 | 9/1996 | |
| WO | WO 1998/004310 | 2/1998 | |
| WO | WO 1998/012965 | 4/1998 | |
| WO | WO 98/23305 A1 | 6/1998 | |
| WO | WO 99/16327 A1 | 4/1999 | |
| WO | WO 99/25410 A1 | 5/1999 | |
| WO | WO 1999/043375 | 9/1999 | |
| WO | WO 1999/061088 | 12/1999 | |
| WO | WO 2000/020072 | 4/2000 | |
| WO | WO 2000/038772 | 7/2000 | |
| WO | WO 00/50121 A1 | 8/2000 | |
| WO | 00/69497 A1 | 11/2000 | |
| WO | WO 00/64521 A1 | 11/2000 | |
| WO | WO 2000/069521 | 11/2000 | |
| WO | WO 2000/072905 | 12/2000 | |
| WO | WO 2000/074758 | 12/2000 | |
| WO | WO 2000/076568 | 12/2000 | |
| WO | WO 2000/078384 | 12/2000 | |
| WO | WO 2001/062326 | 8/2001 | |
| WO | WO 2001/095965 | 12/2001 | |
| WO | WO 2001/097892 | 12/2001 | |
| WO | WO 2001/097893 | 12/2001 | |
| WO | WO 02/38221 A1 | 5/2002 | |
| WO | WO 2002/045784 | 6/2002 | |
| WO | WO 2003/090827 | 11/2003 | |
| WO | WO 2003/105921 | 12/2003 | |
| WO | WO 2004/022146 | 3/2004 | |
| WO | WO 2004/041342 | 5/2004 | |
| WO | WO 2004/073778 | 9/2004 | |
| WO | WO 2004/078230 | 9/2004 | |
| WO | 2004/096332 A1 | 11/2004 | |
| WO | WO 2005/018524 A2 | 3/2005 | |
| WO | WO 2005/053781 | 6/2005 | |
| WO | WO 2005/063328 | 7/2005 | |
| WO | WO 2005/086943 | 9/2005 | |
| WO | WO 2005/099801 | 10/2005 | |
| WO | WO 2005/110220 | 11/2005 | |
| WO | WO 2005/118040 | 12/2005 | |
| WO | PCT/AU2006/000031 | 1/2006 | |
| WO | PCT/AU2006/000417 | 3/2006 | |
| WO | 2006/063339 | 6/2006 | |
| WO | PCT/AU2006/000770 | 6/2006 | |
| WO | WO 2006/069415 | 7/2006 | |
| WO | WO 2006/074513 | 7/2006 | |
| WO | WO 2006/074516 | 7/2006 | |
| WO | WO 2006/099658 | 9/2006 | |
| WO | WO 2006/130903 | 12/2006 | |
| WO | WO 2007/009182 | 1/2007 | |
| WO | 2007/016424 A2 | 2/2007 | |
| WO | WO 2007/016424 | 2/2007 | |
| WO | WO 2007/041751 | 4/2007 | |
| WO | WO 2007/041786 | 4/2007 | |
| WO | WO 2007/048174 | 5/2007 | |
| WO | WO 2007/053878 | 5/2007 | |
| WO | PCT/AU2007/001936 | 12/2007 | |
| WO | WO 2007/143772 A2 | 12/2007 | |
| WO | WO 2007/145534 | 12/2007 | |
| WO | WO 2008/011682 | 1/2008 | |
| WO | WO 2008/011683 | 1/2008 | |
| WO | 2008/019294 A2 | 2/2008 | |
| WO | WO 2008/019294 | 2/2008 | |
| WO | WO 2008/040050 | 4/2008 | |
| WO | WO 2008/070929 | 6/2008 | |
| WO | WO 2009/108994 | 9/2009 | |
| WO | WO 2009/109004 | 9/2009 | |
| WO | WO 2009/146484 A1 | 12/2009 | |
| WO | WO 2010/028425 | 3/2010 | |

OTHER PUBLICATIONS

Notification of Reexamination dated Nov. 23, 2015 issued in Chinese Application No. 200910163947.3 with English translation (13 pages).

Notice of Reasons for Rejection dated May 11, 2015 issued in Japanese Application No. 2014-7642 with English translation (7 pages).

Decision of Rejection dated Feb. 28, 2015 issued in Chinese Application No. 200910163947.3 with English translation (15 pages).

Patent Examination Report No. 1 for corresponding Australian Application No. 2009202232, dated Sep. 4, 2012, 4 pages.

Office Action issued in Chinese Patent Application No. 200910163947.3 dated Aug. 29, 2013 (with translation).

Chinese Notification of First Office Action and English Translation for corresponding Chinese Application No. 200910163947.3, dated Dec. 13, 2012, 8 pages.

Decision of Rejection and English Translation for corresponding Japanese Application No. 2009-135413, dated Dec. 24, 2013, 6 pages.

Notice of Reasons for Rejection and English Translation issued in corresponding Japanese Application No. 2009-135413, dated Jul. 2, 2013. 7 pages.

Notification of Fourth Office Action dated Oct. 10, 2014 in Chinese Application No. 200910163947.3, with English Translation (11 pages).

Notification of Third Office Action and English Translation for corresponding Chinese Application No. 200910163947.3, dated Mar. 13, 2014, 11 pages.

"Ear Loop Face Mask".

Webster's Third New International Dictionary, 1993, Dictionary definition for adjustable, bendable, and mild steel.

(56) References Cited

OTHER PUBLICATIONS

ComfortLite™, Respironics, http://comfortlite.respironics.com.
ComfortLite™ 2, Respironics, http://comfortlite2.respironics.com.
"If You Hate CPAP! You Need CPAP Pro®," www.cpappro.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, dated Dec. 1, 2009.
Examination Report filed in New Zealand Application 539836, dated Aug. 25, 2005.
Examiner's Report No. 3 dated Nov. 18, 2009 in New Zealand Application No. 2003275762.
Extended European Search Report dated Mar. 19, 2009 in European Application No. EP 08161249.
Extended European Search Report dated Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Merriam-Webster Online Dictionary definition of moveable from the 14th century.
Office Action dated Dec. 22, 2009 in European Appln. No. 04802133.1.
ResMed Co.—Mask Products—http://resmed.com/portal/site/ResMedUS/index.jsp?. . .
Respironics Co.—Mask Family—http://masksfamily.respironics.com/.
Snapp Nasal Interface, Tiara Medical Systems, Inc.—http://www.tiaramed.com/asp_shops/shopdisplayproducts.asp?id=109&cat=SNAPP%2A+Nasal+Interface.
Supplementary European Search Report dated Sep. 8, 2009 in European Appln. No. 04802133.1.
Supplementary Search Report issued in European Appln. 05746824.1, dated Dec. 17, 2009.
Supplementary European Search Report dated Dec. 18, 2009 in European Application No. 03810331.3.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Examination Report dated Dec. 8, 2010 in New Zealand Application No. 589634 (3 pages).
Adam J. Singer MD et al., "The Cyanoacrylate Topical Skin Adhesives," American Journal of Emergency Medicine, vol. 26, 2008, pp. 490-496.
Subbu Venkatraman et al., "Review Skin Adhesives and Skin Adhesion 1. Transdermal Drug Delivery Systems," Biomaterials, vol. 19, 1998, pp. 1119-1136.
Examination Report for corresponding New Zealand Application No. 589634, dated Apr. 26, 2012, 2 pages.
Examination Report dated Feb. 28, 2011 in European Application No. 09 161 984.1 (4 pages).
Joel W. Beam, "Tissue Adhesives for Simple Traumatic Lacerations," Journal of Athletic Training, 2008, vol. 43, No. 2, pp. 222-224.
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Decision of Reexamination dated Mar. 30, 2016 issued in Chinese Application No. 200910163947.3 with English translation (26 pages).
Notice of Reasons for Rejection dated Apr. 10, 2017 issued in Japanese Application No. 2015-185135 with English translation (18 pages).
Office Action dated Feb. 21, 2017 issued in Chinese Application No. 201510369858.X with English translation (23 pages).

(56) References Cited

OTHER PUBLICATIONS

Notification of the Second Office Action dated Sep. 19, 2017 issued in Chinese Application No. 201510369858.X with English translation (27).
Decision of Rejection dated Apr. 16, 2018 issued in Chinese Application No. 201510369858.X with English translation (11 pages).
First Office Action dated Jan. 29, 2018 issued in Chinese Application No. 201610509138.3 with English translation (20 pages).
Office Action dated Oct. 15, 2018 issued in Chinese Application No. 201610509138.3 with English translation (12 pages).
Jan. 4, 2019 Appeal Decision issued in Japanese Application No. 2015-185135 (with translation).

* cited by examiner

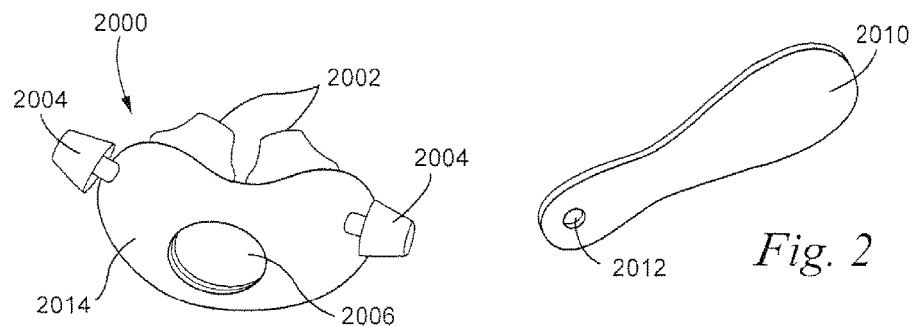
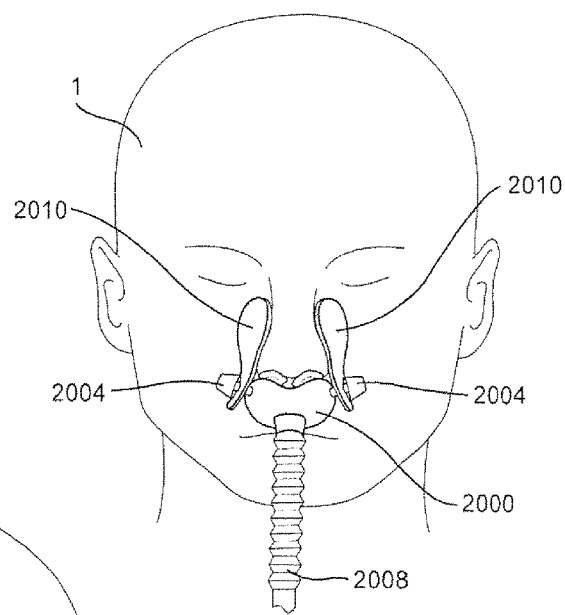
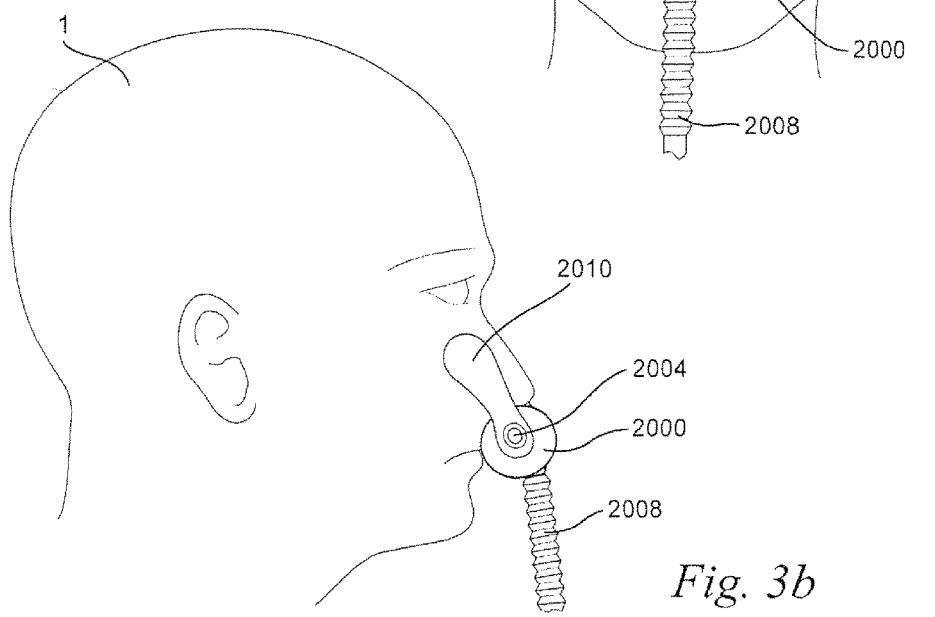

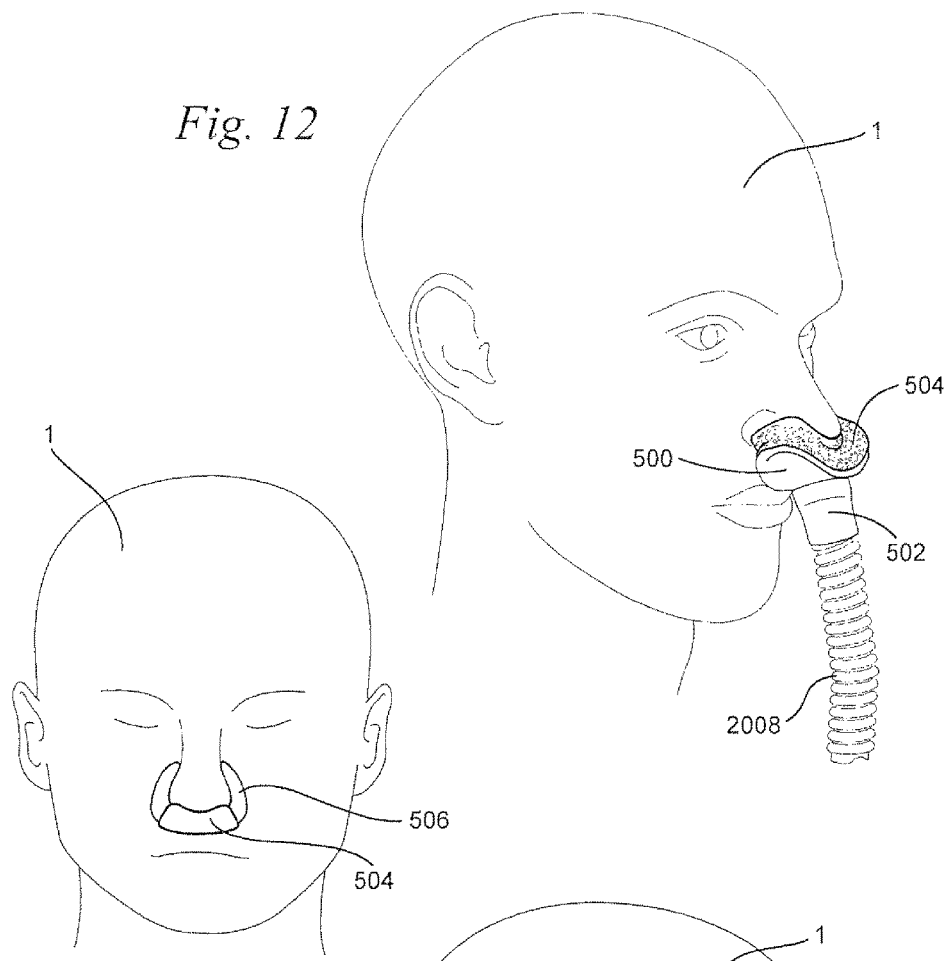
Fig. 12
Fig. 13a
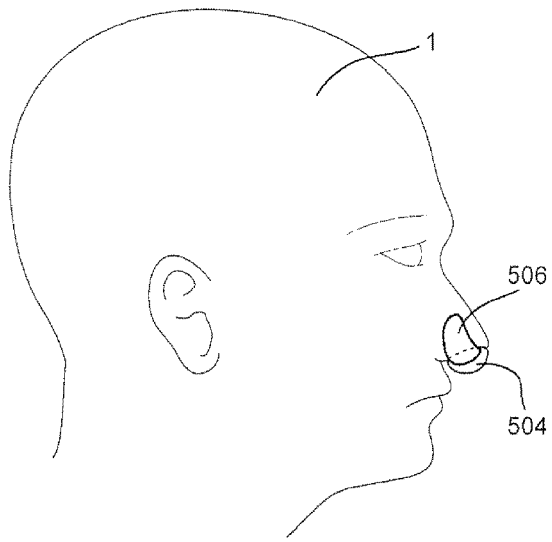
Fig. 13b

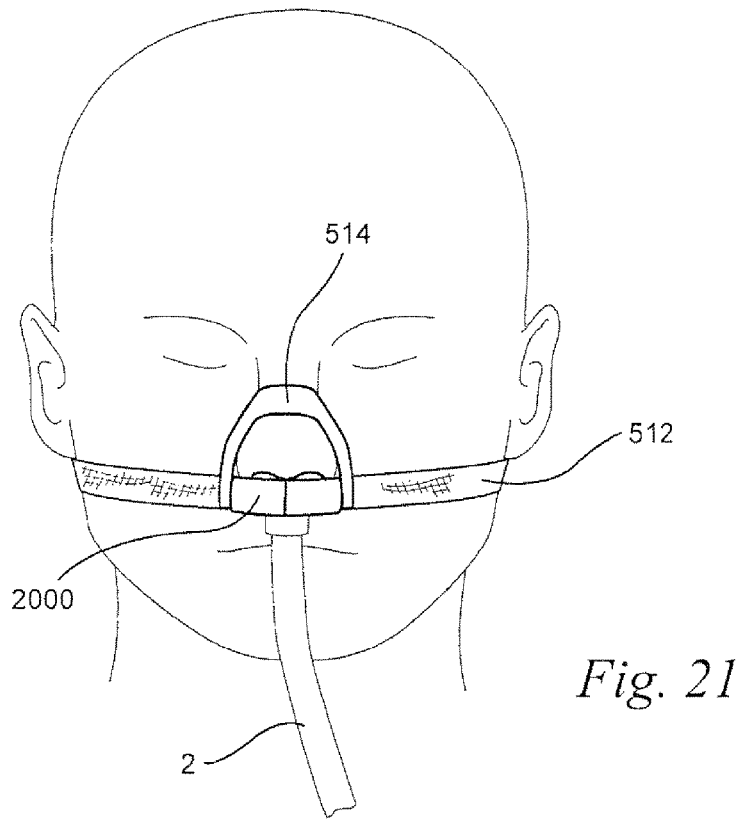
Fig. 21
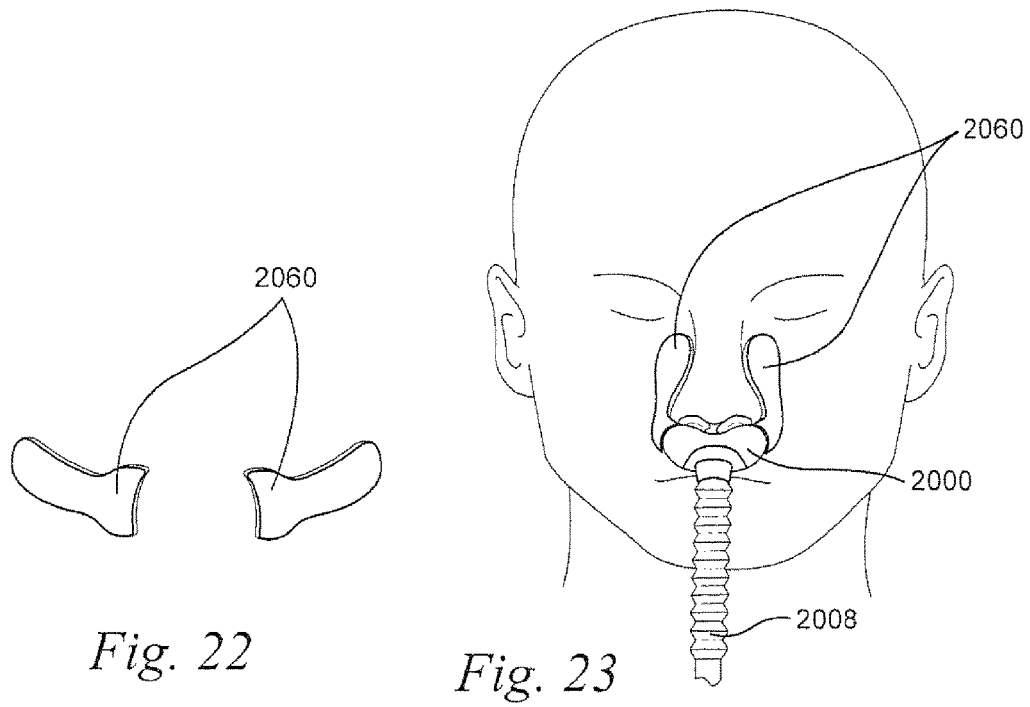
Fig. 22
Fig. 23

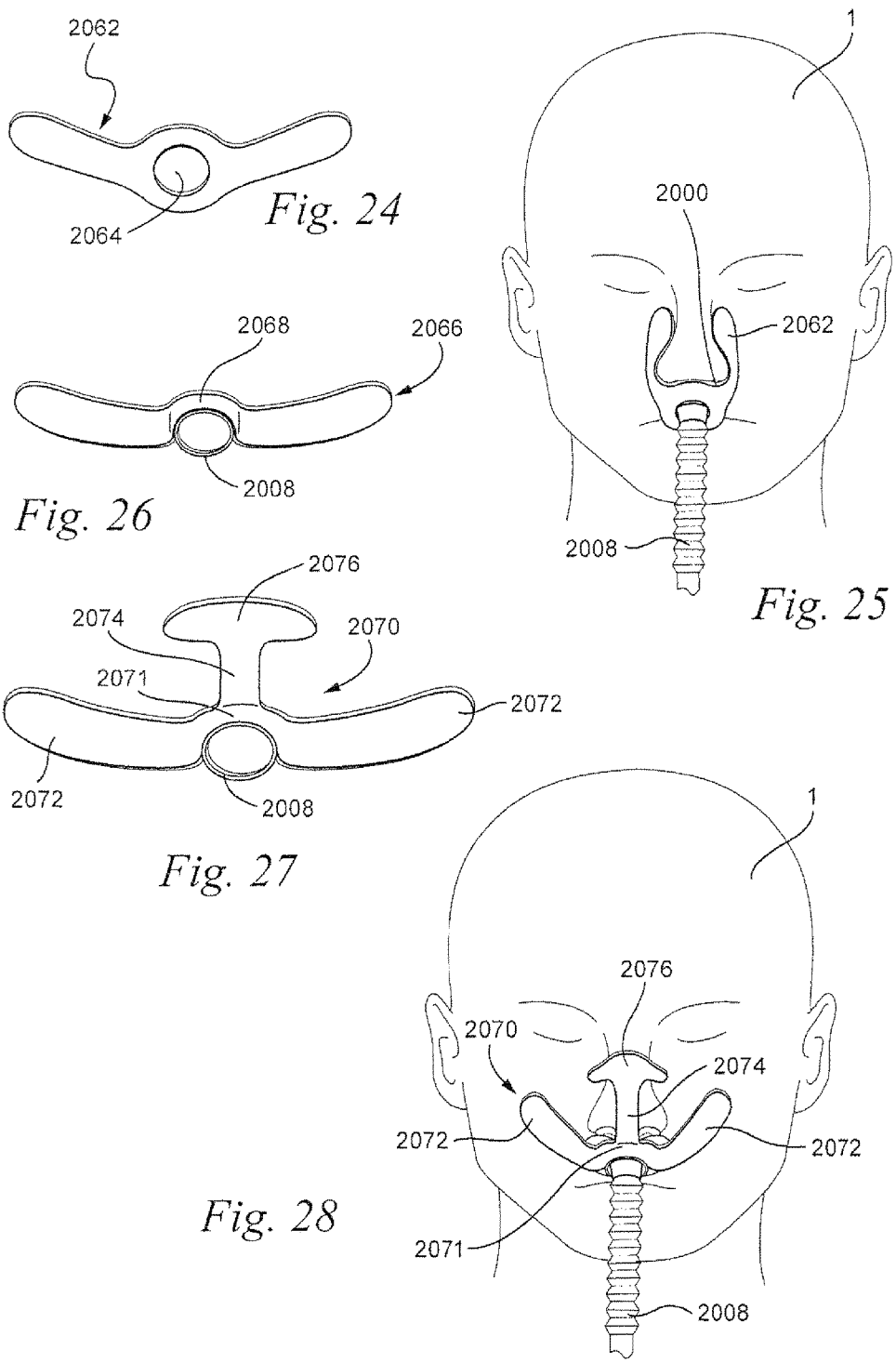

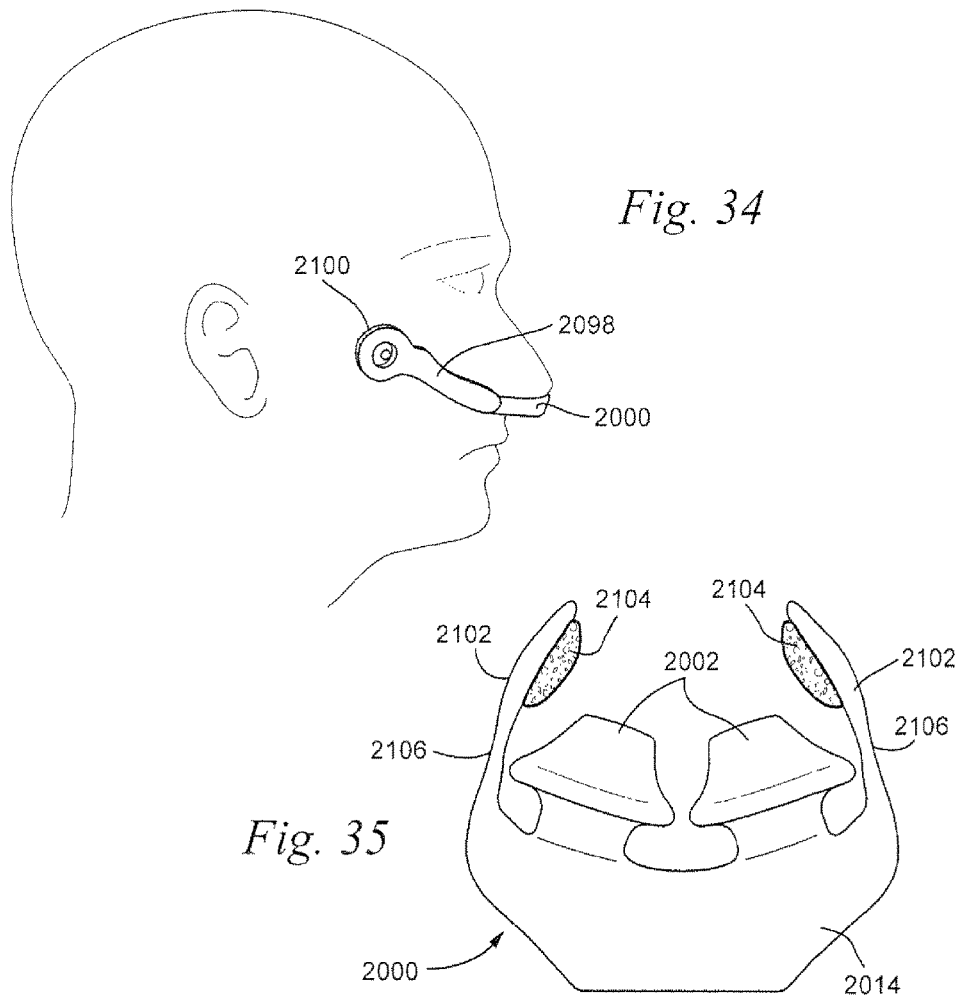
Fig. 34
Fig. 35
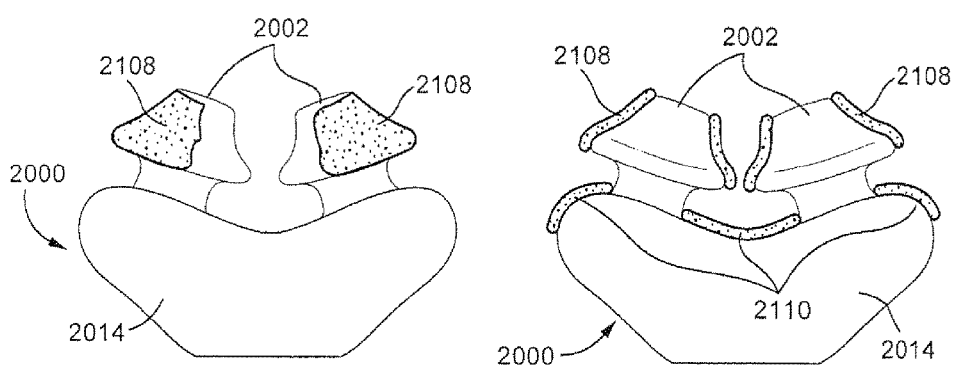
Fig. 36
Fig. 37

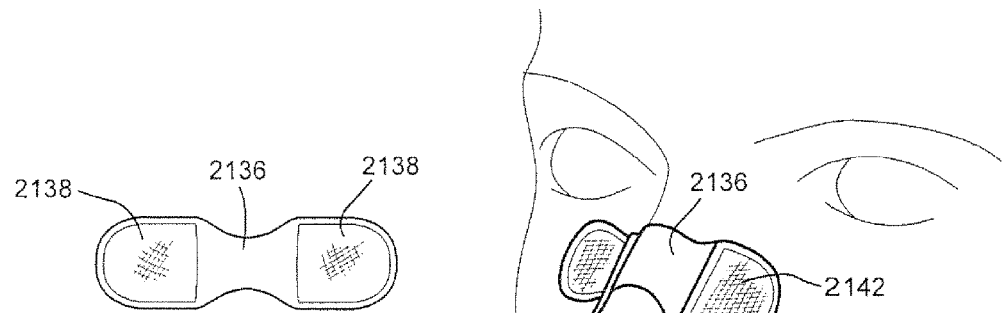
Fig. 48
Fig. 49
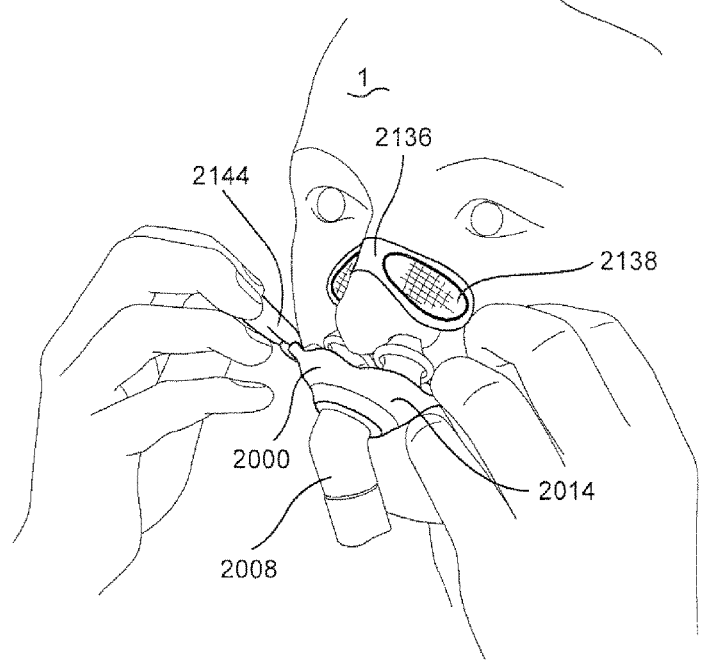
Fig. 50a

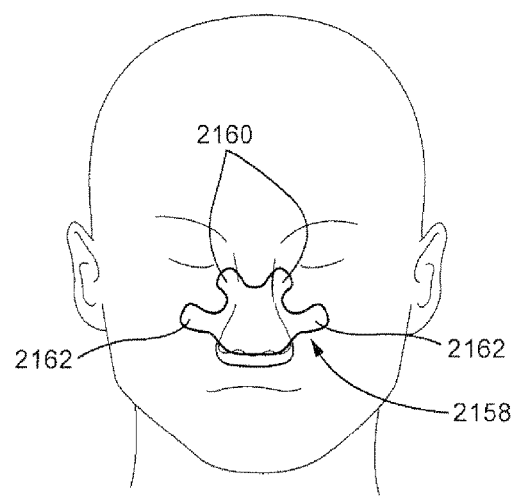
Fig. 64
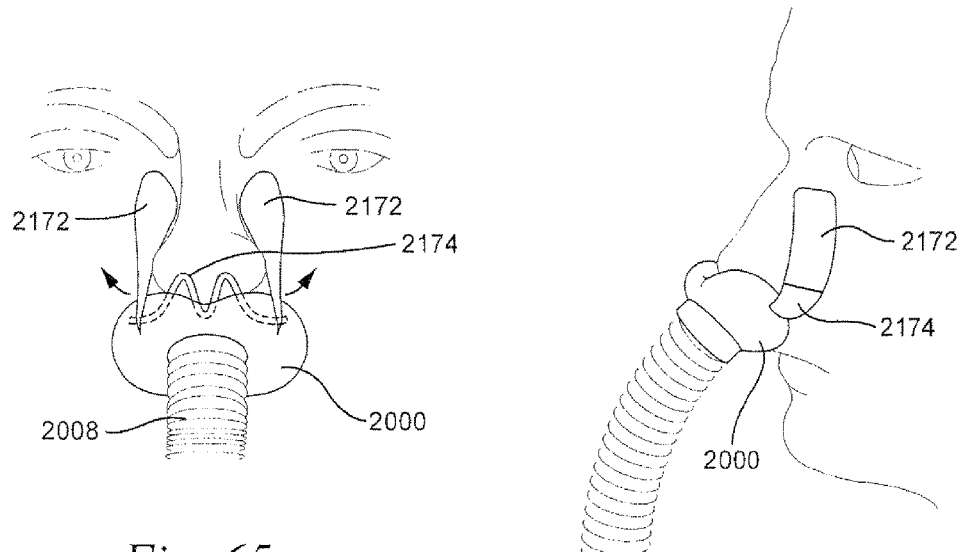
Fig. 65a
Fig. 65b

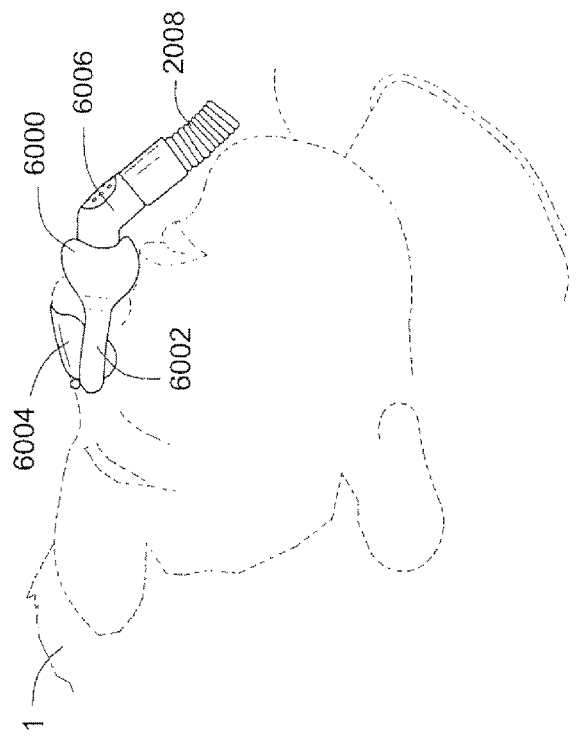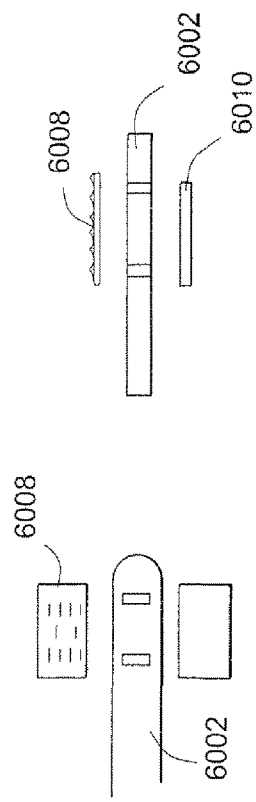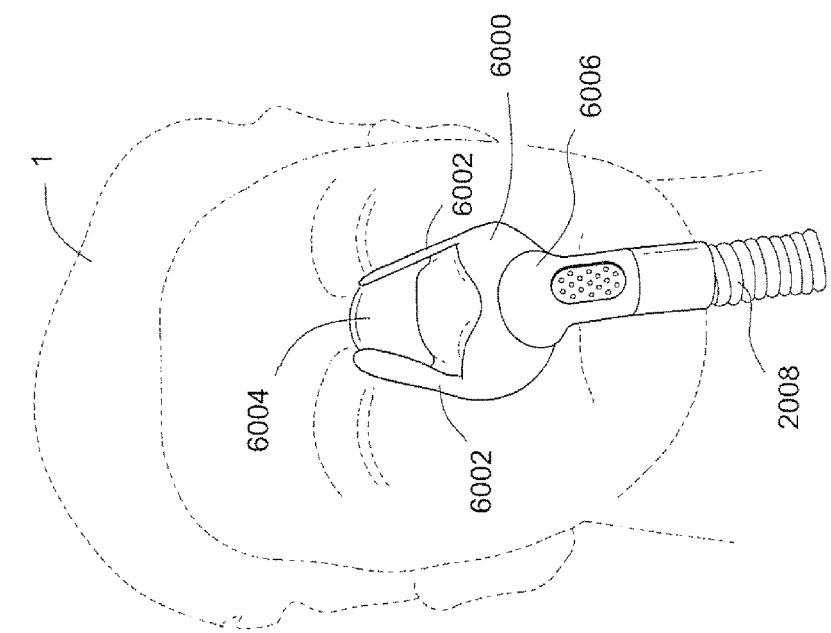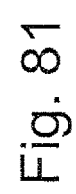

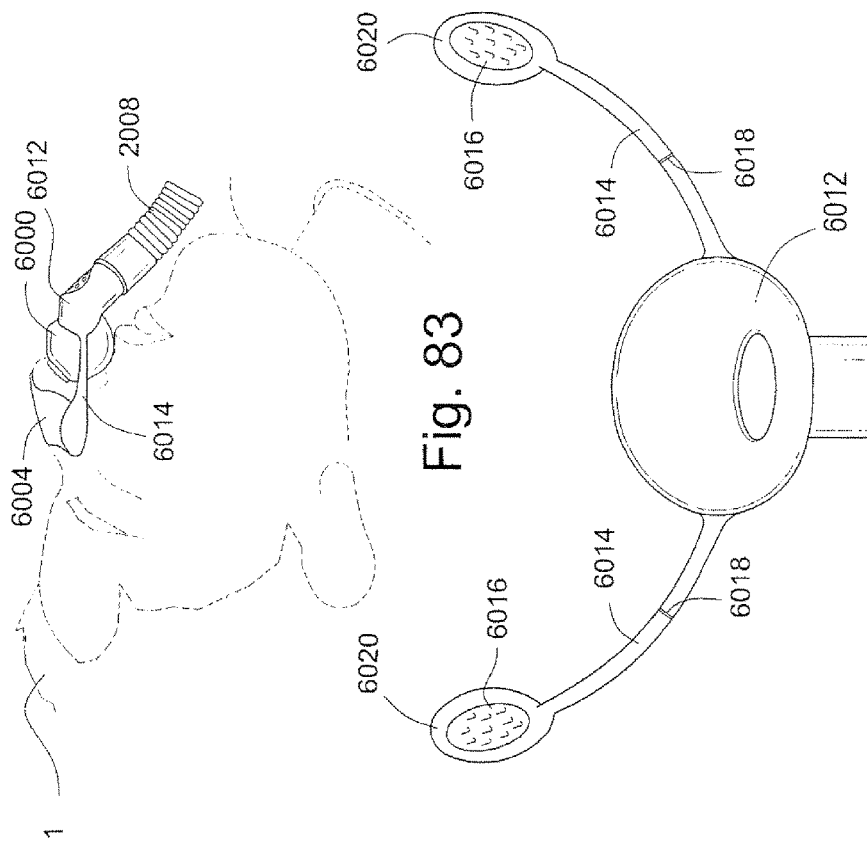
Fig. 83
Fig. 84
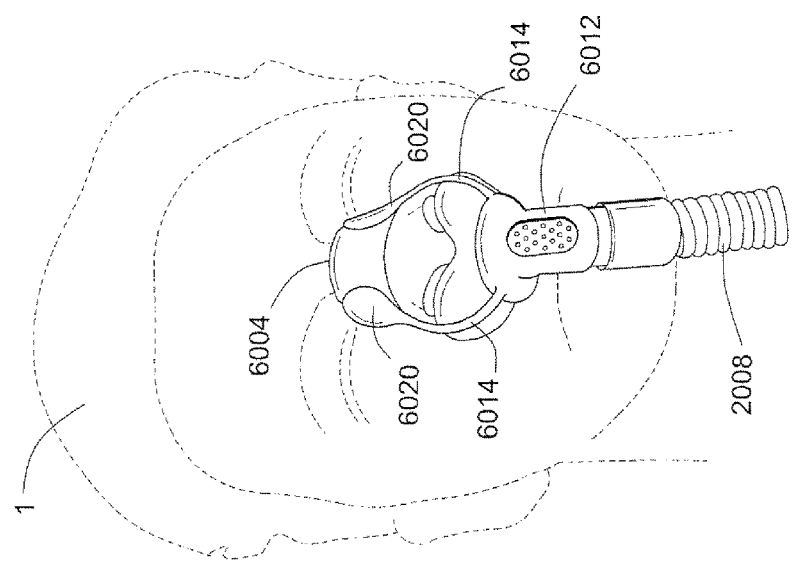
Fig. 82

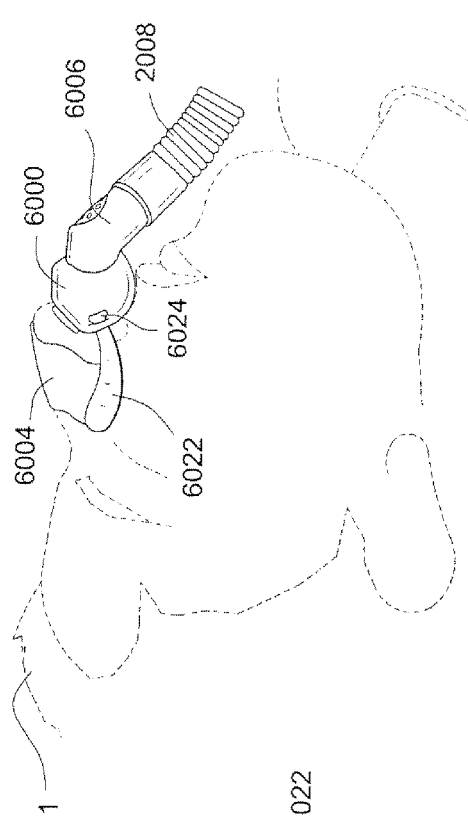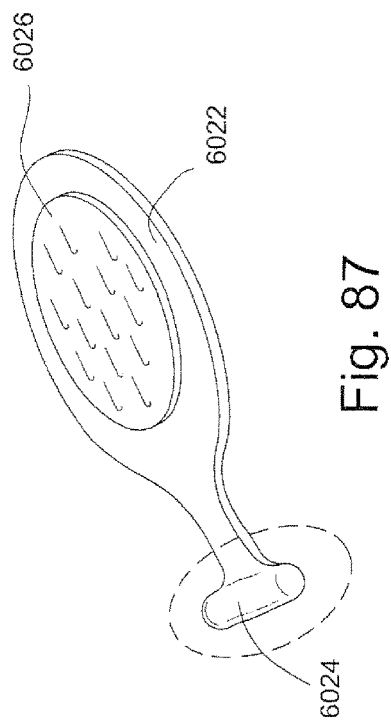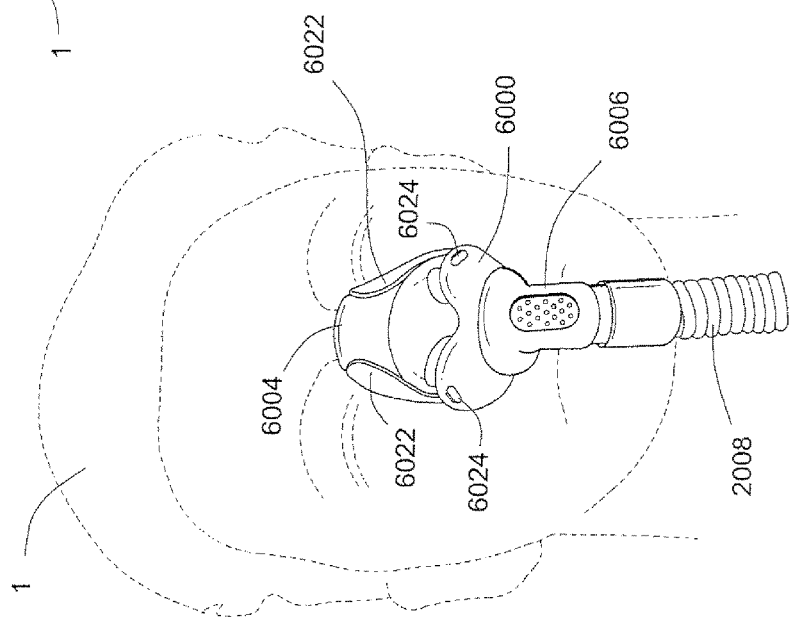
Fig. 86
Fig. 87
Fig. 85

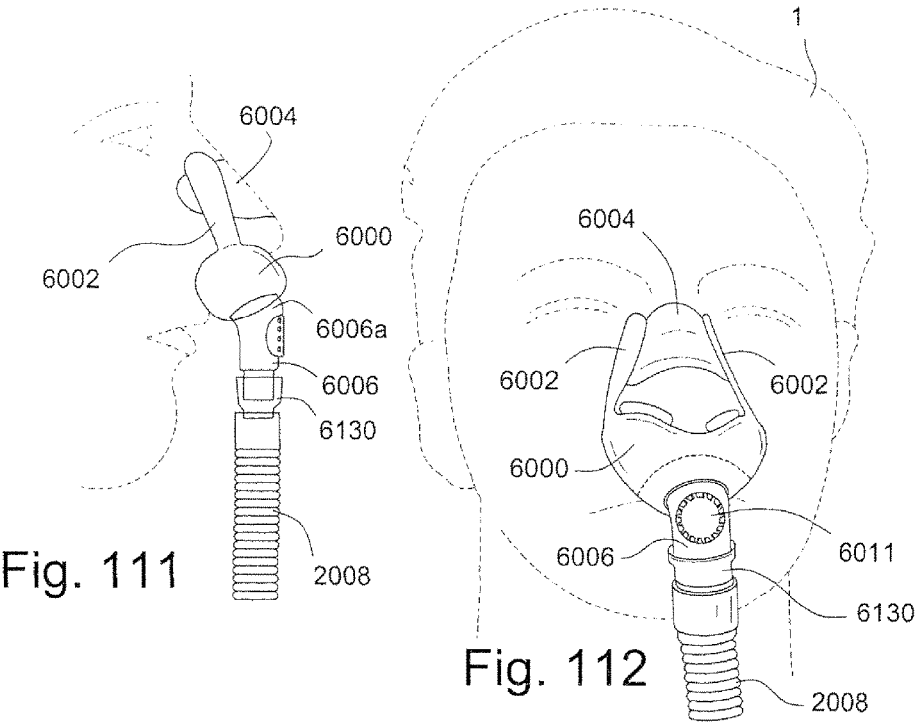
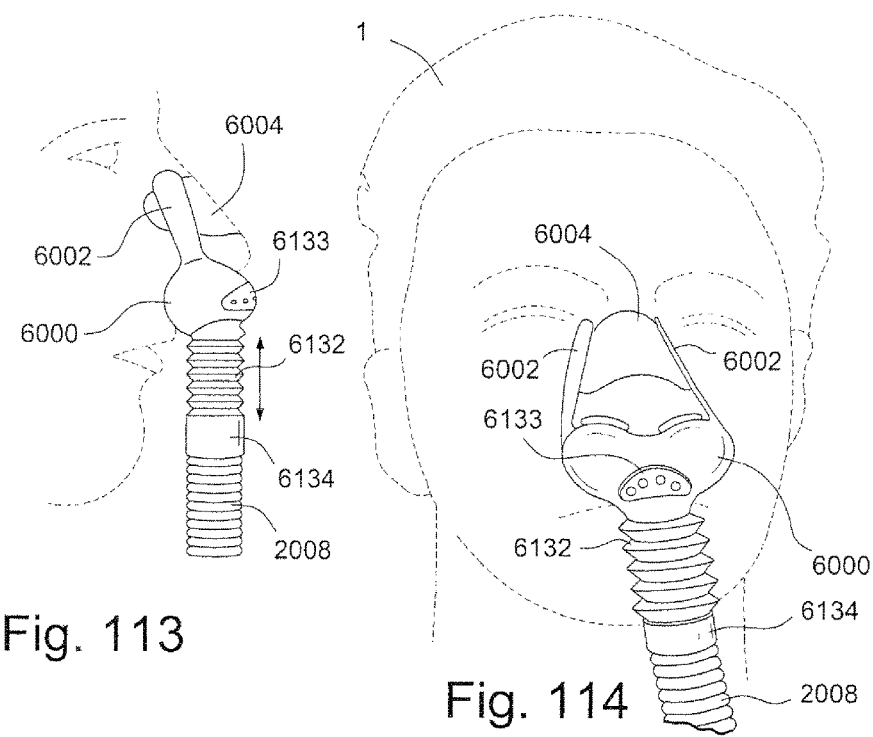

PATIENT INTERFACE SYSTEMS

CROSS REFERENCE TO RELATED APPLICATIONS

This application is a continuation of U.S. application Ser. No. 13/619,512, filed Sep. 14, 2012, now allowed, which is a divisional of U.S. application Ser. No. 12/478,537, filed Jun. 4, 2009, now U.S. Pat. No. 8,291,906, which claims priority to U.S. Applications 61/058,659, filed Jun. 4, 2008, and 61/080,847, filed Jul. 15, 2008, each incorporated herein by reference in its entirety.

FIELD OF THE INVENTION

The present invention relates to patient interface systems for delivery of a flow of breathable gas to a patient. The present invention also relates to patient interface systems that may include adhesive(s) to support the patient interface in engagement with the patient and/or a patient interface positioning and/or support structure.

BACKGROUND OF THE INVENTION

The use of positive airway pressure (PAP) for the treatment of sleep disordered breathing (SDB), such as obstructive sleep apnea (OSA), was disclosed in U.S. Pat. No. 4,944,310. Treatment using PAP, which may be continuous PAP (CPAP), involves the use of a patient interface which is attached to the patient's face for the provision of the flow of breathable gas. PAP treatment involving the use of a patient interface that is sealingly attached to the wearer's face may be referred to as closed PAP.

Mild or moderate cases of SDB may not be suitable for treatment using closed PAP methods. For example, patients who experience mild sleep apnea, or who may snore, may not gain a significant benefit from the use of closed PAP treatment. In addition, such patients may tend to resist treatment as closed PAP treatment methods generally are obtrusive.

For patients that require a higher prescribed pressure for treatment of OSA, a patient interface, e.g. a mask, that forms a seal with the patient's airways may be required. However, the patient may find adapting to current interfaces difficult. For example, the patient may have difficulty sleeping in a familiar, comfortable position once the mask, including the headgear and air delivery hose, are fitted to the patient to provide the required seal. Although the mask is capable of providing a seal and the prescribed pressure, the patient may be reluctant to use the mask due to the problem of sleeping comfortably while wearing the mask. This may result in the patient abandoning the treatment.

SUMMARY OF THE INVENTION

One aspect relates to patient interface systems for delivering a flow of breathable gas to a patient's airways while sealing the patient's airways.

Another aspect relates to patient interface systems that are securable to the patient using an adhesive. Still another aspect relates to the use of adhesive that adheres to the patient's face and the patient interface structure that engages the patient's nose. A further aspect relates to the use of adhesive to secure the patient interface structure to the patient and the adhesive is adhesively or mechanically connected to the patient interface structure.

Another aspect relates to the use of adhesive to position and stabilize the patient interface structure to deliver a flow of breathable gas. Still other aspects relate to the use of adhesive and additional fastening arrangements, such as hook and loop fastening material, magnets, interference fittings, or electrostatic connectors, to position and stabilize the patient interface structure. Even further aspects relate to additional positioning and stabilizing arrangements usable with or without adhesive.

Yet another aspect relates to a patient interface system that includes adhesive to adhere the patient interface structure to the face of the patient and permits the repositioning of the patient interface structure while the patient interface structure remains adhered to the face of the patient.

A further aspect relates to patient interface systems that are securable to the patient using adhesive and that provide for dilation of the patient's nasal passageways.

Still another aspect relates to a patient interface system that includes an inflatable nozzle, such as a nasal pillow, that is configured to expand and sealingly engage the patient's nares upon the application of a flow of breathable gas. Another aspect relates to support for the patient interface structure including the inflatable nozzle which may be secured across the bridge of the patient's nose with adhesive.

Yet another aspect relates to patient interface structure that includes an inflatable membrane that may be connected to the inflatable nozzles.

According to a sample embodiment, a patient interface system for delivering a flow of breathable gas to a patient comprises a patient interface structure configured to sealingly engage the patient's nares; a pair of arms configured to be connected to opposite sides of the patient interface structure; and adhesive configured to secure the patient interface structure in sealing engagement with the patient's nares, wherein the adhesive is provided on the arms, and the arms are configured to be adhered to sides of the patient's nose by the adhesive.

Another aspect of the present technology is a two part arrangement. A first part is adhesively secured to the face of the patient, e.g. sides of the nose. A second part, comprising a seal forming structure such as nasal pillows, is removably attachable to the first part. Removable attachment between the first and second parts may be achieved by a range of mechanisms such as adhesive and mechanical interlocking structures such as hook and loop material or interlocking fasteners, e.g. manufactured by 3M Corporation.

According to another sample embodiment, a patient interface system for delivering a flow of breathable gas to a patient comprises a first component comprising adhesive on a first side and a first fastener element on a second side, wherein the adhesive is configured to adhere the component to the face of the patient; and a patient interface structure configured to sealingly engage the patient's airways, the patient interface structure including a second component comprising a second fastener element configured to engage the first fastener element of the first strip to secure the patient interface structure in sealing engagement with the patient's face. The patient interface structure is repositionable by disengaging the second component from the first component and reengaging the second component with the first component.

According to a further sample embodiment, a patient interface system for delivering a flow of breathable gas to a patient comprises a patient interface structure, the patient interface structure including a base portion defining a breathing cavity configured to receive the flow of breathable gas through an aperture in the patient interface structure, pair of nasal pillows or prongs configured to engage the nares of the patient to deliver the flow of breathable gas from the breathing cavity to the patient; and adhesive on the pair of nasal pillows or prongs configured to secure the patient interface structure to the patient.

According to a still further sample embodiment, a patient interface system for delivering a flow of breathable gas to a patient comprises a patient interface structure comprising a pair of nasal prongs or pillows configured to sealingly engage the patient's nares; and at least one spring configured to bias the nasal prongs or pillows outwards into engagement with the nares of the patient.

According to yet another sample embodiment, a patient interface system for delivering a flow of breathable gas to a patient comprises a patient interface support structure configured to be connected to a hose that delivers the flow of breathable gas; a pair of nasal pillows supported by the patient interface support structure, wherein each nasal pillow is configured to inflate and seal against an interior of the patient's nares by an increase of pressure in the patient interface support structure from receipt of the flow of breathable gas; a support member configured to engage a bridge of the patient's nose; and a connecting member configured to connect the support member and the patient interface support structure.

According to a further sample embodiment, a patient interface system for delivering a flow of breathable gas to a patient comprises a patient interface structure configured to sealingly engage the face of the patient; and a retaining element configured for application to the patient, said retaining element being configured to support the patient interface structure in sealing engagement with the face of the patient, the retaining element comprising an adhesive and/or at least one strap. The patient interface structure is configured to be released from and re-engaged with the retaining element for re-positioning of the patient interface structure relative to the patient's face in a plurality of positions while the retaining element remains supported by the patient Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various sample embodiments, wherein:

FIG. 1 schematically illustrates a patient interface structure according to a sample embodiment;

FIG. 2 schematically illustrates an adhesive strip connector according to a sample embodiment usable with the patient interface structure of FIG. 1;

FIGS. 3a and 3b are schematic front and side views of an interface system according to a sample embodiment including the patient interface structure of FIG. 1 and the adhesive strip connectors of FIG. 2;

FIG. 12 schematically illustrates an interface system according to a sample embodiment;

FIGS. 13a-13f schematically illustrate an interface system according to another sample embodiment;

FIG. 21 schematically illustrates an interface system according to another sample embodiment;

FIGS. 22 and 23 schematically illustrate an interface system according to another sample embodiment;

FIGS. 24 and 25 schematically illustrate an interface system according to another sample embodiment;

FIG. 26 schematically illustrates an adhesive strip connector according to another sample embodiments;

FIGS. 27 and 28 schematically illustrate an interface system according to another sample embodiment of the invention;

FIG. 34 schematically illustrates an interface system according to another sample embodiment;

FIG. 35 schematically illustrates an interface system according to another sample embodiment;

FIG. 36 schematically illustrates a patient interface structure according to another sample embodiment;

FIG. 37 schematically illustrates an interface system according to another sample embodiment;

FIGS. 48 and 49 schematically illustrate an interface system according to another sample embodiment;

FIGS. 50a-50c schematically illustrate an interface system according to another sample embodiment;

FIG. 64 schematically illustrates an adhesive strip for positioning an interface system according to another sample embodiment;

FIGS. 65a and 65b schematically illustrate an interface system according to another sample embodiment;

FIGS. 78-81 schematically illustrate a patient interface system according to another sample embodiment;

FIGS. 82-84 schematically illustrate a patient interface system according to another sample embodiment;

FIGS. 85-87 schematically illustrate a patient interface system according to another sample embodiment;

FIGS. 111 and 112 schematically illustrate a patient interface system according to another sample embodiment;

FIGS. 113 and 114 schematically illustrate a patient interface system according to another sample embodiment;

DETAILED DESCRIPTION

Figure 4:
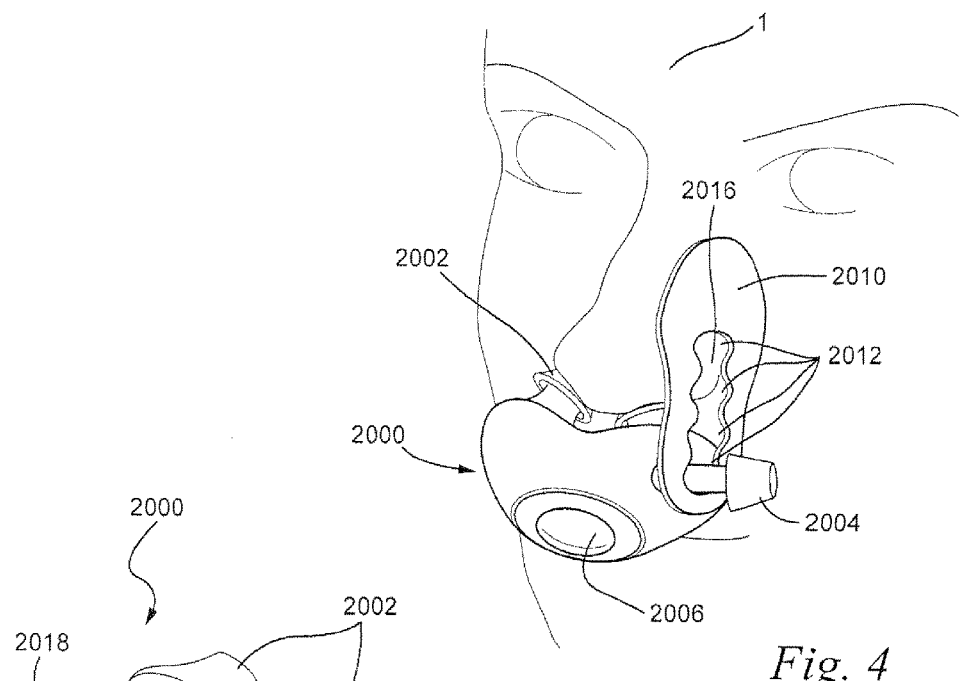
FIG. 4 schematically illustrates an adhesive strip connector according to another sample embodiment that is usable with the patient interface structure of FIG. 1.

The following description is provided in relation to several sample embodiments which may share common characteristics and features. It is to be understood that one or more features of any one embodiment may be combinable with one or more features of the other embodiments. In addition, any single feature or combination of features in any of the sample embodiments may constitute additional embodiments.

In this specification, the word "comprising" is to be understood in its "open" sense, that is, in the sense of "including", and thus not limited to its "closed" sense, that is the sense of "consisting only of" A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

As used herein, the term "patient interface structure" refers to a structure configured to engage the face of a patient and deliver the flow of breathable gas to the patient's airways.

1.0 Positioning and Stabilizing Using Adhesive

Adhesive may be used to secure the patient interface structure in engagement with the patient's airways. Adhesive that is intended to engage the face of the patient will be referred to as the patient adhesive. The patient adhesive may engage the patient's face and position and stabilize the patient interface structure on the face of the user, but it is not necessary for forming a sealing engagement of the patient interface with the user. The patient adhesive may be repositionable to allow the patient to adjust the position of the patient interface structure. In general, the patient adhesive may be mechanically fixed to the patient interface structure or adhesively fixed to the patient interface structure. In the following sections a range of technologies that do not require adhesive will be described as mechanical fixation. However in some forms adhesive may be used. Adhesive fixation includes the use of adhesive to join the patient adhesive to the patient interface structure.

1.1.1 Mechanical Fixation First Embodiment

Referring to FIGS. 1-3b, a patient interface structure may comprise a patient interface structure, e.g. a cushion, 2000 comprising nasal pillows, puffs, or prongs 2002. The patient interface structure 2000 may also comprise tabs, or studs, 2004 at opposite ends of a base portion 2014. The patient interface structure 2000 may further include an aperture 2006 configured to allow for connection of a tube, hose, or conduit 2008. The tube 2008 may be, for example, a retractable tube, such as disclosed in U.S. Patent Application Publication 2009/0078259 A1, the entire contents of which are incorporated herein by reference.

The studs 2004 are each configured to be connected to a patient adhesive strip 2010 that includes a hole 2012 at a first end. The studs 2004 are inserted through the holes 2012 of the patient adhesive strip 2010 to secure the patient adhesive strips 2010 to the patient interface structure. The top portion of stud 2004 may be wider than hole 2012 such that the stud is secured in position once placed through the hole by an interference fit. The holes 2012 may be reinforced to prevent damage to, or degradation of, the patient adhesive strips 2010. The patient adhesive strips 2010 may be connected to the studs 2004 such that the patient adhesive strips 2010 are rotatable with respect to the patient interface structure 2000 in order to locate the patient adhesive strips 2010 in the desired position on the face of the patient 1. As shown in FIGS. 3a and 3b, the patient adhesive strips 2010 are engaged with the sides of the nose of the patient 1. The patient adhesive strips 2010 include adhesive on one side that is engaged with the side of the patient's nose.

The patient adhesive strips 2010 may be generally elliptical, rectangular, or any other desired shape. As shown in FIG. 2, the proximal end of the patient adhesive strip 2010, i.e. the end including the hole 2012, may be smaller than the distal end that engages the side of the patient's nose. A middle section of the patient adhesive strip 2010 may be narrowed. It should be appreciated that the patient adhesive strips 2010 may be provided in different sizes and shapes to accommodate a variety of patient facial features.

It should also be appreciated that the patient adhesive strips 2010 may include tabs or studs that are configured to be inserted into holes or apertures provided in the patient interface structure 2000. It should also be appreciated that the patient adhesive strips 2010 may include adhesive in selected or localized regions, for example, at the distal end that engages the side of the patient's nose.

This embodiment demonstrates an aspect of the present technology where the adhesive is used to locate the patient interface in position however remains separate from the sealing of the patient interface to the patient.

1.1.2 Mechanical Fixation Second Embodiment

Referring to FIG. 4, the patient adhesive strips 2010 (only one shown) may include a plurality of holes or spacings 2012 that are each configured to accept the tab or stud 2004 of the patient interface structure 2000. As shown in FIG. 4, the plurality of holes 2012 are joined by a channel 2016 formed in the patient adhesive strip 2010 that permits the stud 2004 to be disengaged from one hole and engaged with another hole without completely disengaging the patient adhesive strip 2010 from the stud 2004. The stud 2004 may be disengaged from one hole 2012 and engaged with another hole 2012 to permit adjustment of the position of the patient adhesive strip 2010 without completely disengaging the adhesive strip 2010 from the patient interface structure 2000. It should be appreciated that the holes 2012 of the patient adhesive strip 2010 may be formed separately, i.e. without a channel, so that adjustment of the position of the patient adhesive strip 2010 requires disengagement of the stud 2004 from one hole, and from the patient adhesive strip 2010, and re-engagement with a different hole and the patient adhesive strip 2010. It should also be appreciated that the patient adhesive strip may include a tab or stud and the patient interface structure may include a plurality of holes each configured to receive the tab or stud to permit adjustment of the adhesive strip.

1.1.3 Mechanical Fixation Third Embodiment

Figure 5:
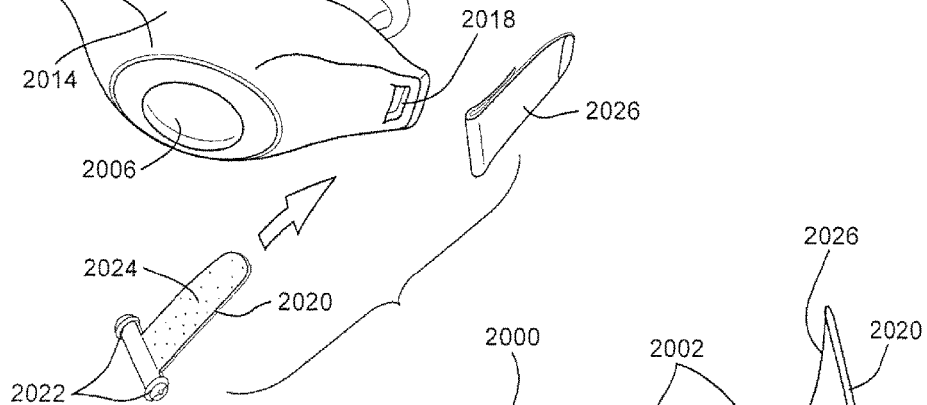
FIGS. 5-7 schematically illustrate an interface system according to another sample embodiment.
Figure 6:
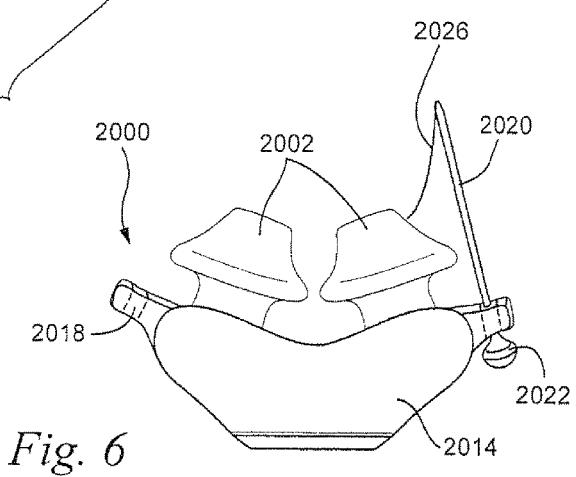
Figure 7:
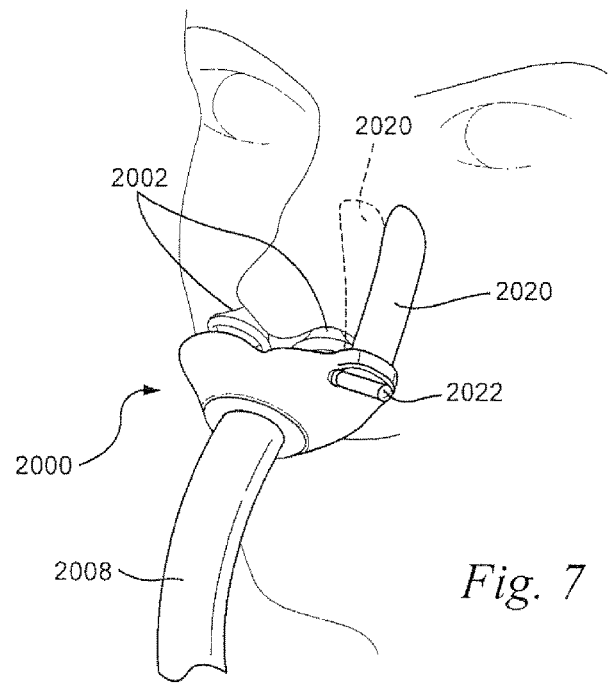

Referring to FIGS. 5-7, the patient interface system may comprise a patient interface structure 2000 provided with loops 2018 on opposite sides of the patient interface structure 2000. Patient adhesive strips 2020 (only one shown) may be inserted through the loops 2018 and locked in place on the patient interface structure 2000 by locking tabs 2022. The locking tabs 2022 may be rigid or semi-rigid (for example, silicone, polycarbonate, polypropylene, thermoplastic elastomers (TPE), etc.) and are provided to the adjoining ends of the patient adhesive strips 2020. The adhesive 2024 of the patient adhesive strips 2020 may be covered by, for example, release paper 2026 to allow the patient adhesive strips 2020 to be inserted through the loops 2018 so that the patient adhesive strips 2020 can be pulled through the loops 2018 until the locking tabs 2022 engage with the loops 2018.

The locking tabs 2022 may be molded onto the patient adhesive strips 2020. It should also be appreciated that the locking tabs 2022 may be adhered to the patient adhesive strips 2020. It should further be appreciated that the locking tabs 2022 may be secured within a portion of the patient adhesive strip 2020 by wrapping the patient adhesive strip 2020 around the locking tab 2022. The wrapped portion of the patient adhesive strip 2020 may be secured by adhesive, stitching, or any other securement method. The locking tabs 2022 may be secured to the patient adhesive strip 2020 by any other securement method.

The loops 2018 may be integrally formed with the patient interface structure 2000, or they may be separately provided, e.g. clipped or glued, onto the patient interface structure 2000. As shown in FIGS. 5 and 6, the loops 2018 may be provided on the base portion 2014 of the patient interface structure 2000. The base portion 2014 of the patient interface structure 2000 may include a decoupling arrangement configured to decouple drag forces on the hose or tube 2008 from the nasal prongs 2002 of the patient interface structure 2000. Such a decoupling arrangement is disclosed in, for example, International Application PCT/AU2008/001557, filed Oct. 22, 2008, the entire contents of which are incorporated by reference.

As shown in FIG. 7, the position of the patient adhesive strips 2020 may be adjusted, as shown in dashed lines, to permit adjustment of the position of the patient interface structure.

1.1.4 Mechanical Fixation Fourth Embodiment

Figure 8A:
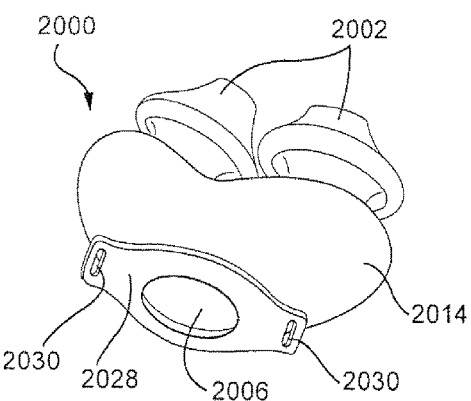
FIGS. 8a and 8b schematically illustrate an interface system according to another sample embodiment.
Figure 8B:
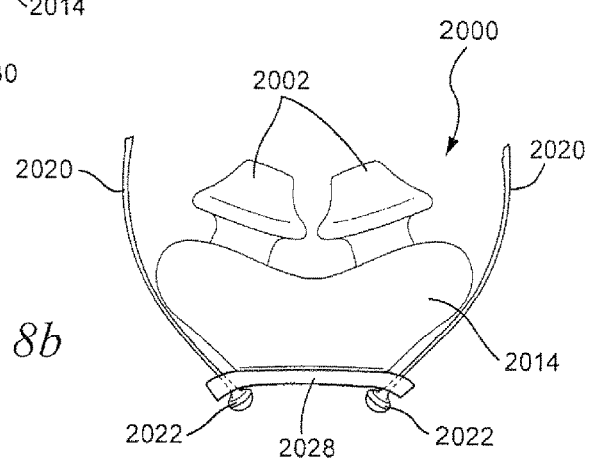

Referring to FIGS. 8a and 8b, in another sample embodiment of the invention, a sealing ring 2028 is provided around the aperture 2006 of the patient interface structure 2000. The sealing ring 2028 is configured to connect a tube or hose to the patient interface structure 2000. The sealing ring 2028 includes loops 2030 which are configured to receive patient adhesive strips 2020 comprising locking tabs 2022 to secure the patient adhesive strips 2020 to the sealing ring 2028. The sealing ring 2028 may be part of a decoupling arrangement as disclosed in, for example, International Application PCT/AU2008/001557, filed Oct. 22, 2008, the entire contents of which are incorporated by reference. Sealing ring 2028 may be otherwise attached to base portion 2014 of the patient interface structure 2000, for example, by gluing, co-molding, insert molding, interference fit, or any other suitable means. Sealing ring 2028 may be made from a rigid material.

1.1.5 Mechanical Fixation Fifth Embodiment

Figure 9:
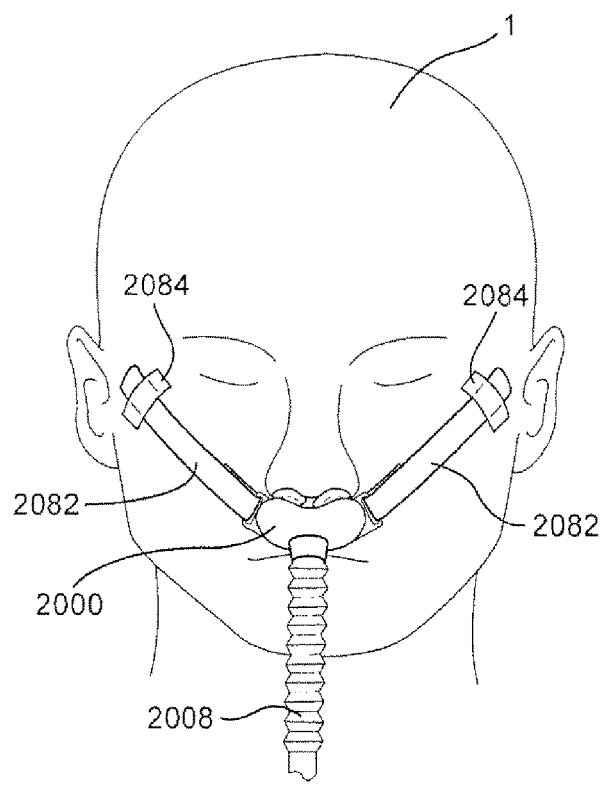
FIG. 9 schematically illustrates an interface system according to another sample embodiment.

Referring to FIG. 9, the patient interface structure 2000 may be secured to the patient 1 by connectors 2082. Such connectors are disclosed, for example, in International Application PCT/AU2008/001557, filed Oct. 22, 2008, the entire contents of which are incorporated by reference. The patient interface structure 2000 is held in sealing engagement with the nares of the patient by the connectors 2082 which are secured to the face of the patient by adhesive strips 2084 which adhesively secure the connectors 2082 to the patient 1.

Although a single adhesive strip 2084 is shown for each corresponding connector 2082 in FIG. 9, it should be appreciated that multiple strips may be secured in a variety of places on the patient interface system, or a single piece may be configured around components of the interface system, such as the delivery tube 2008 or a gusset of the base portion 2014 of the patient interface structure 2000.

1.1.6 Mechanical Fixation Sixth Embodiment

Figure 10:
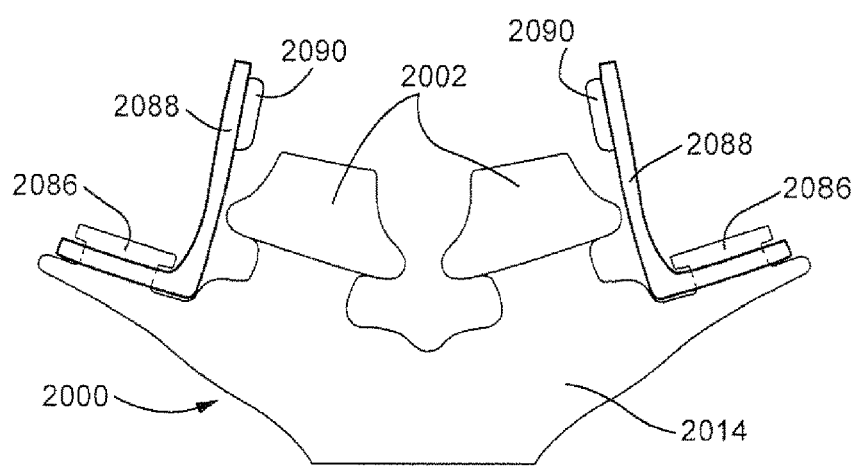
FIG. 10 schematically illustrates an interface system according to another sample embodiment.

Referring to FIG. 10, the patient interface system may comprise a patient interface structure 2000 comprising connectors 2086 that are configured to secure strips 2088 to the patient interface structure 2000. The strips 2088 may be formed of a rigid, semi-rigid, or non-rigid material, for example, of silicone, textile, polycarbonate, polypropylene, nylon, TPE, and may hook around the connectors 2086 and extend upward towards the nose of the patient. The strips 2088 may comprise adhesive tabs 2090 that are configured to engage the sides of the nose of the patient to secure the strips 2088, and thus the patient interface structure 2000, in engagement with the face of the patient.

1.2.1 Adhesive Fixation First Embodiment

Figure 11A:
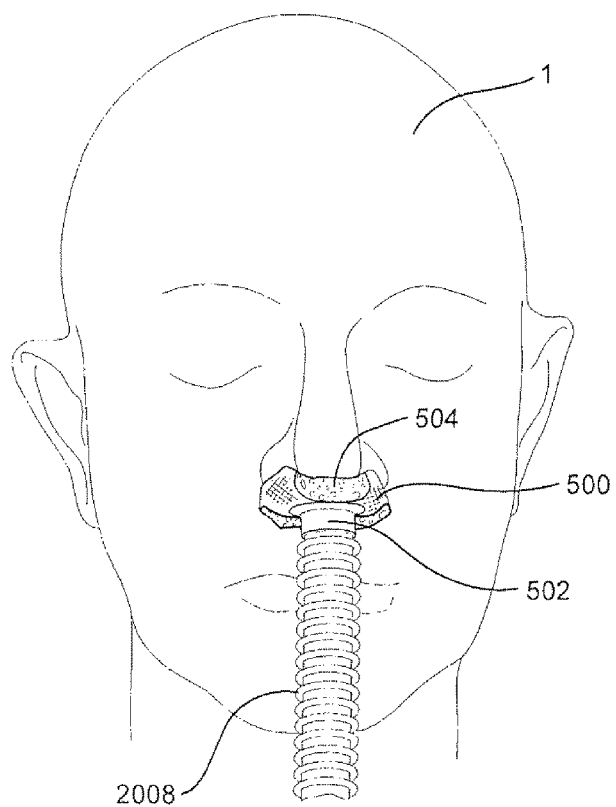
FIGS. 11a and 11b schematically illustrate an interface system according to another sample embodiment.
Figure 11B:
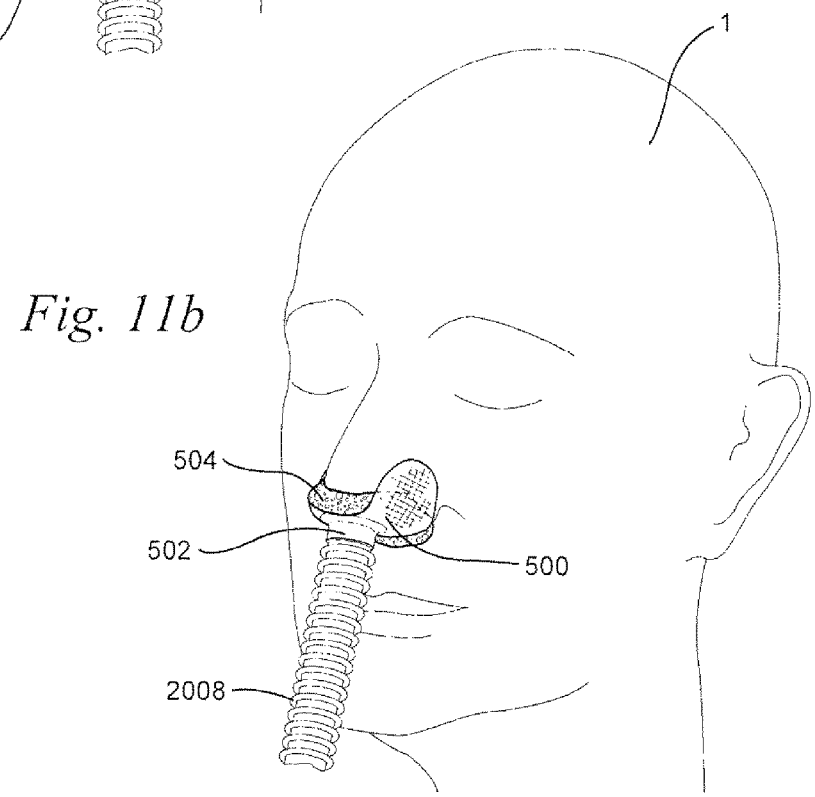
Figure 13C:
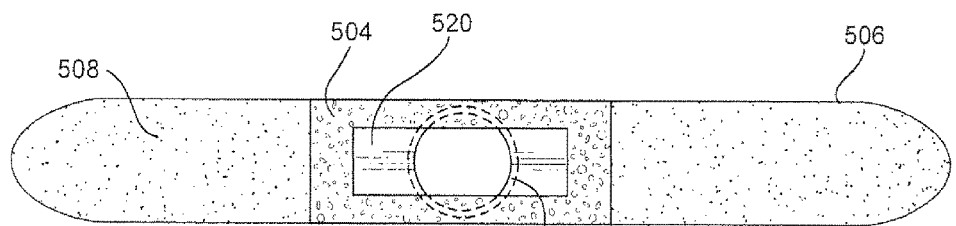
Figure 13D:
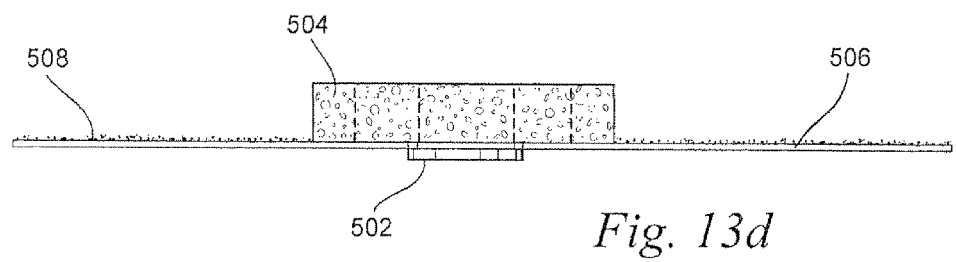
Figure 13E:
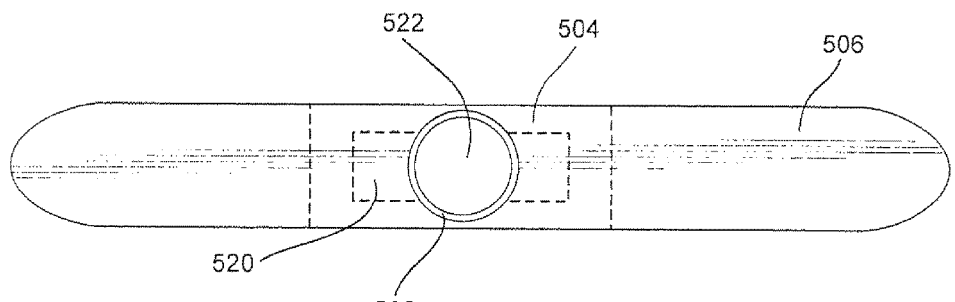
Figure 13F:
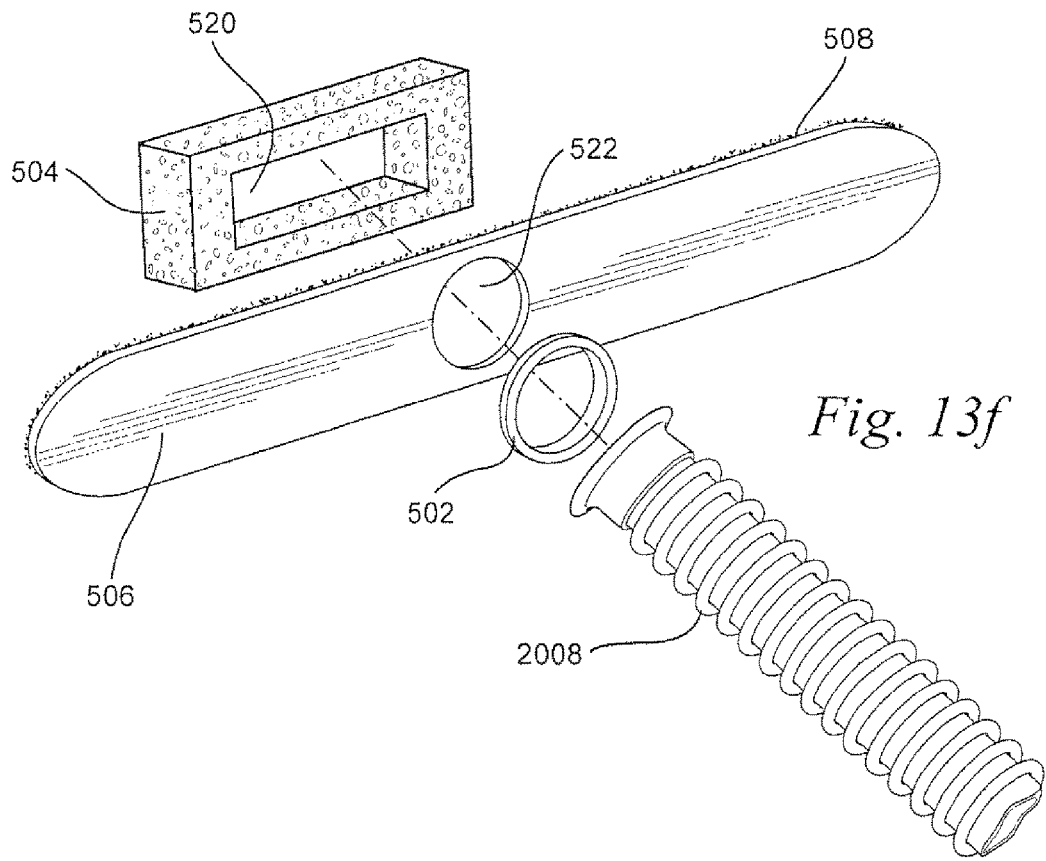

Referring to FIGS. 11a and 11b, a patient interface system according to another embodiment may comprise a patient interface structure in the form of a cushion 504 that is adhesively connected to the nose of the patient 1. The cushion 504 may be connected to a frame, or support, 500 that is connectable to a supply of breathable gas by, for example, a retractable tube 2008. The frame 500 may be connected to the retractable tube 2008 by a sealing ring 502. The sealing ring 502 may connect the retractable tube 2008 to the frame 500 so that the retractable tube 2008 and the frame 500 are swivelable with respect to one another. The use of a retractable tube will impart less tube drag forces on the patient interface structure and thus enable more effective maintenance of the mask seal at the nares and/or mouth.

The adhesive may be a sticky element that can mechanically or chemically join or bond two adjacent members, e.g. the cushion 504 and the nose of the patient 1. The adhesive is configured to maintain the patient interface system, including the cushion 504, in place while minimizing obtrusiveness. The patient interface system allows the patient to sleep in any position and does not obscure any part of the patient's face, thereby enabling the patient to wear, for example, eye glasses or an eye shield. The attachment of the adhesive to the patient's face is simple and intuitive and provides a user friendly interface. Compared to other patient interface structures and systems currently available, for example ResMed's SWIFT II™, the adhesively secured patient interface system of FIGS. 11a and 11b is smaller. With the smaller appearance, the patient interface system will also appear less medical; reducing the patient's psychological barriers to respiratory treatment, and therefore may be more appealing to patients. The smaller appearance may also motivate and encourage more people to seek treatment for sleep apnea.

In a sample embodiment, the adhesive may be used to locate the patient interface system on the face of the patient 1. In one form, the adhesive may not impart any force on the sealing mechanism of the interface system. That is, the sealing of the interface, including the cushion 504, is independent or isolated from its attachment to the patient's face. This means that the interface system will be more comfortable for the patient to wear as less force will be imposed on the face of the patient by the adhesive. In other sample embodiments, the adhesive may not be the only structure that can locate or locate and seal the interface to the patient's face. For example, a headgear may be used in conjunction with an adhesive to locate the interface.

In one sample embodiment, the cushion 504 may seal on the nares and/or mouth of the patient by, for example, a dual wall silicone, foam, or gel cushion. In another sample embodiment, the cushion may not seal on the nares and/or mouth of the patient and may comprise, for example, nasal cannula(e).

1.2.2 Adhesive Fixation Second Embodiment

Referring to FIG. 12, in another sample embodiment of the invention, the patient interface system includes a cushion 504 connected to a frame, or support, 500. The frame 500 is connected a source of breathable gas by, for example, a retractable tube 2008 that is connected to the frame 500 by a sealing ring 502. As shown in FIG. 12, the cushion 504 and the frame 500 are curved to encompass the area around the patient's nares. The curved frame 500 may provide a better sealing engagement for patient's with higher and/or smaller nares. The cushion 504 may be adhesively connected to the nose of the patient 1.

1.2.3 Adhesive Fixation Third Embodiment

Referring to FIGS. 13a-13f, a patient interface system may comprise a patient interface structure, for example a cushion 504, that is configured to be held in sealing engagement with the nose of the patient 1 by a strap 506 that comprises adhesive. The strap 506 is configured to be adhesively connected to the sides of the patient's nose to hold the cushion 504 in the proximity of the nares. The cushion 504 may be connected to a source of breathable gas by, for example, a retractable tube 2008 as discussed above. The cushion 504 may also be supported by a strap 506 and the cushion 504 may be connected to the tube by, for example, a sealing ring 502 that may swivelably couple the tube to the cushion 504.

The cushion 504 may comprise an aperture 522 configured to receive the sealing ring 502. The cushion further defines a nasal breathing cavity 520 into which the flow of breathable gas is delivered by the tube 2008.

As shown in FIGS. 13c-13f, the strap 506 is provided between the cushion 504 and the sealing ring 502. The strap 506 may include adhesive 508 that is provided on the same side of the strap as the cushion 504. The strap 506 may be substantially flexible to permit the strap 506 to be folded around the sides of the patient's nose.

1.2.4 Adhesive Fixation Fourth Embodiment

Figure 14:
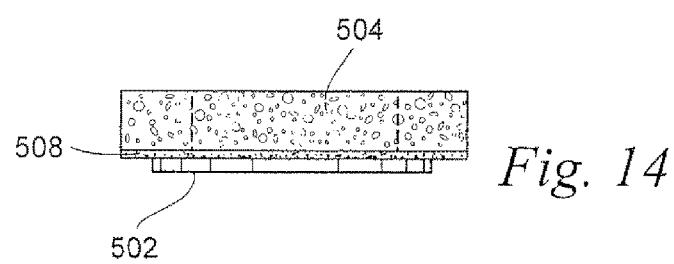
FIG. 14 schematically illustrates a patient interface structure according to another sample embodiment.

Referring to FIG. 14, a patient interface structure comprising a cushion 504 may have a generally rectangular configuration. The cushion 504 defines a nasal breathing cavity 520 having a shape generally corresponding to the shape of the cushion 504. An adhesive 508 may be provided on a side of the cushion 504 that is configured for connection to the sealing ring 502. The adhesive 508 may be used to connect the cushion 504 to a strap in a manner similar to that described above.

1.2.5 Adhesive Fixation Fifth Embodiment

Figure 15:
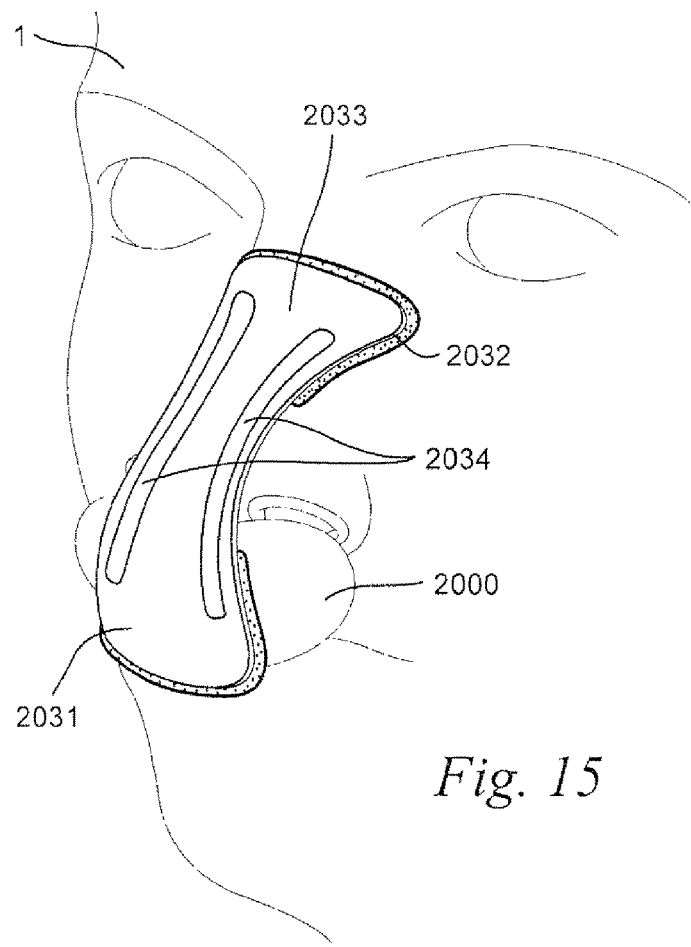
FIG. 15 schematically illustrates an interface system according to another sample embodiment.

Referring to FIG. 15, an adhesive strip 2032 may be configured to maintain a patient interface system comprising a patient interface structure, e.g. a cushion, 2000 in sealing engagement with the nares of the patient 1. The adhesive strip 2032 comprises a bottom portion 2031 configured to adhesively engage the patient interface structure 2000 and a top portion 2033 configured to adhesively engage the bridge of the nose of the patient 1. The adhesive strip 2032 may comprise reinforcements 2034 to provide structure and/or force retention to better support the patient interface structure 2000. The reinforcements may comprise, for example, plastic or metal strips. The adhesive provided to the adhesive strip 2032 need not be continuously provided along the entire length of the adhesive strip 2032. For example, the adhesive may be provided at the bottom portion 2031 and the top portion 2033, but not at a portion therebetween, as shown in FIG. 15.

1.2.6 Adhesive Fixation Sixth Embodiment

Figure 16:
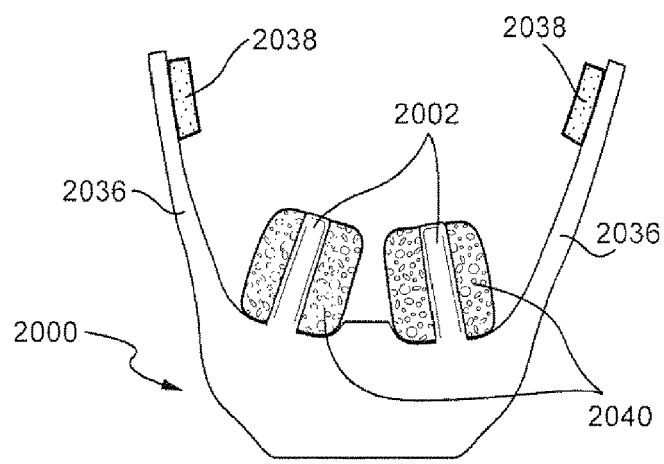
FIG. 16 schematically illustrates an interface system according to another sample embodiment.

As shown in FIG. 16, a patient interface system comprising a patient interface structure 2000 may be provided with connectors 2036 that are configured to engage the face, e.g. the nose, of the patient. Adhesive tabs 2038 may be provided at ends of the connectors 2036 to adhesively secure the patient interface structure 2000 in sealing engagement with the nares of the patient. The nasal prongs, or nozzles, 2002 of the patient interface structure 2000 may be provided with foam cylinders 2040 that are configured to sealingly engage the nares of the patient. The cylinders 2040 may be formed of a foam, for example, similar to that used for earplugs.

1.2.7 Adhesive Fixation Seventh Embodiment

Figure 17:
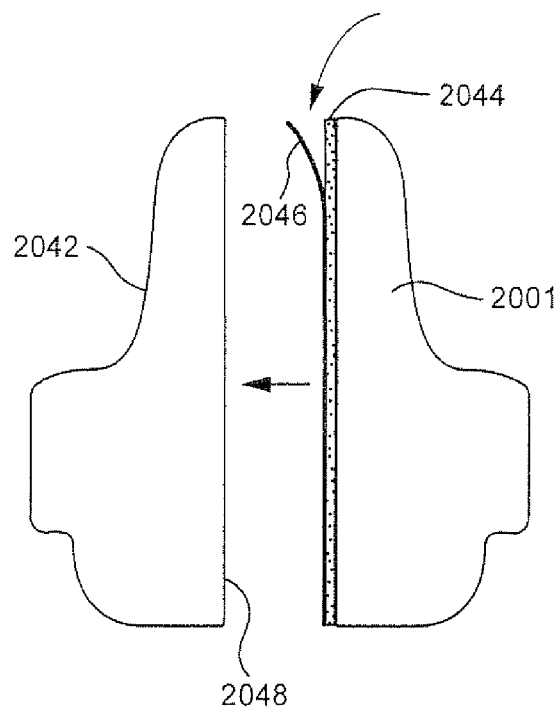
FIGS. 17 and 18 schematically illustrate an interface system according to a sample embodiment.

Referring to FIG. 17, a patient interface system comprising a patient interface structure, e.g. a cushion, 2001 may comprise adhesive 2044 that is covered by, for example, release paper 2046. The cushion 2001 may be adhesively secured to a mask frame or shell 2042 that includes a flat interface 2048. The adhesive 2044 may be double-sided adhesive that adheres the cushion 2001 to the mask frame or shell 2042 upon removal of the release paper 2046 and engagement of the cushion 2001 and the mask frame or shell 2042 along the interface 2048. The cushion 2001 may be held in sealing engagement with the face of the patient by, for example, a headgear assembly (not shown) connected to the mask frame 2042.

1.2.8 Adhesive Fixation Eighth Embodiment

Figure 18:
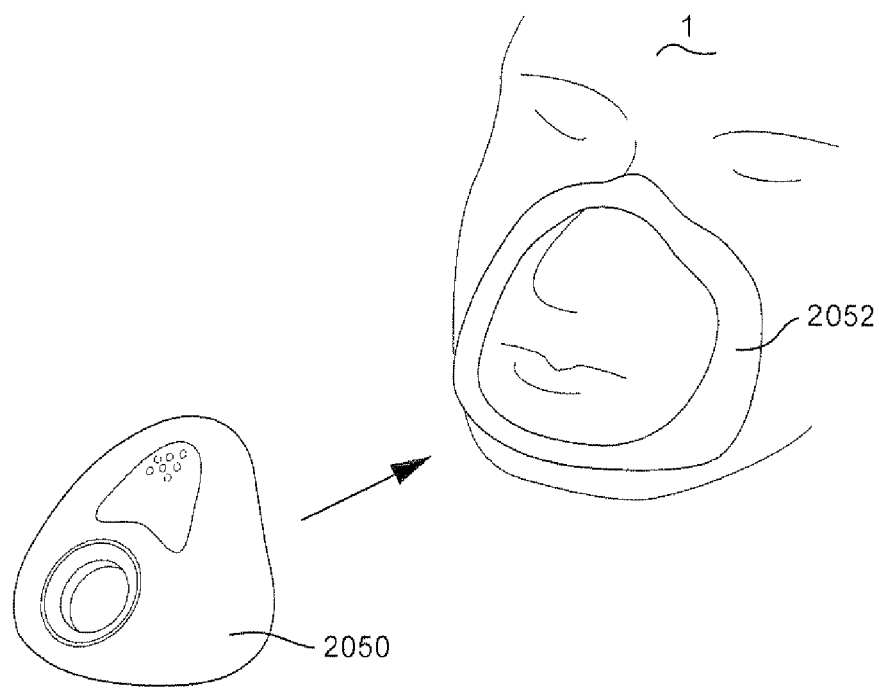

As shown in FIG. 18, according to another sample embodiment of the invention, a patient interface structure comprising a soft mask 2050 may be attached to the face of the patient 1 by adhesive 2052 that is applied to the face of the patient. In this instance, the adhesive 2052 is configured to act as a seal, or assist in forming a seal between the soft mask 2050 and the face of the patient 1. As shown, the soft mask 2050 is in the form of a full face mask, i.e. a mask that is configured to cover the patient's mouth and nasal passageways, but it should be appreciated that the soft mask 2050 may be configured to cover only the patient's mouth or only the patient's nasal passageways.

1.2.9 Adhesive Fixation Ninth Embodiment

Figure 19:
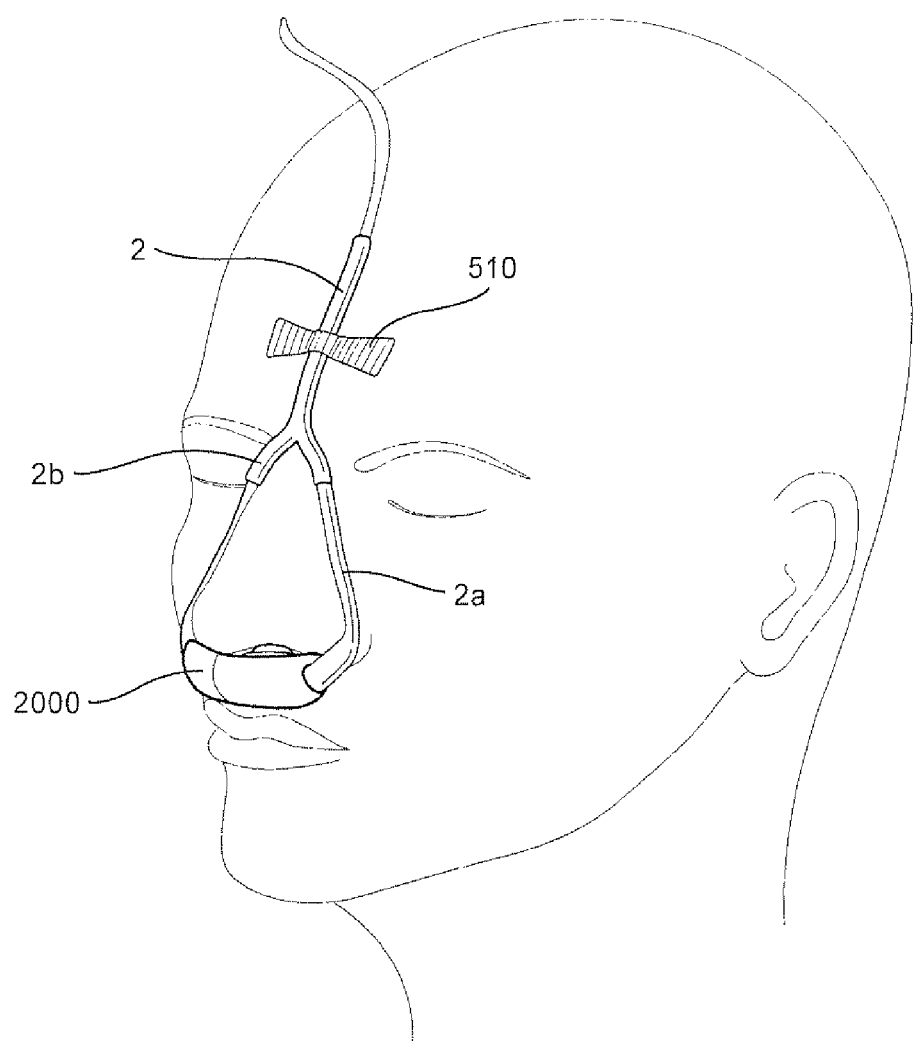
FIG. 19 schematically illustrates an interface system according to another sample embodiment.

Referring to FIG. 19, the patient interface system comprises a patient interface structure, e.g. a cushion, 2000. The flow of breathable gas may be delivered to the patient interface structure 2000 by a cannula 2 comprising cannula branches 2a, 2b that extend on opposite sides of the patient's nose. As shown in FIG. 19, the cannula 2, and branches 2a, 2b may deliver the flow of breathable gas from a position above the patient's nose. The cannula 2 may be secured to the patient's face, e.g. forehead, by adhesive tape 510.

The cannula branches 2a, 2b may be connected to the patient interface structure 2000 for delivery of the flow of breathable gas to a nasal breathing cavity defined by the patient interface structure 2000. For example, the patient interface structure 2000 may include apertures that receive the cannula branches 2a, 2b. As another example, the cannula branches 2a, 2b may be connected to the patient interface structure 2000 such that the cannula branches 2a, 2b extend through the patient interface structure 2000 for insertion into the nares of the patient's nose.

In a variant, the patient interface structure 2000 may include nasal prongs or pillows and the interface system may include a headgear, e.g. a strap, and/or the adhesive tape 510.

1.2.10 Adhesive Fixation Tenth Embodiment

Figure 20A:
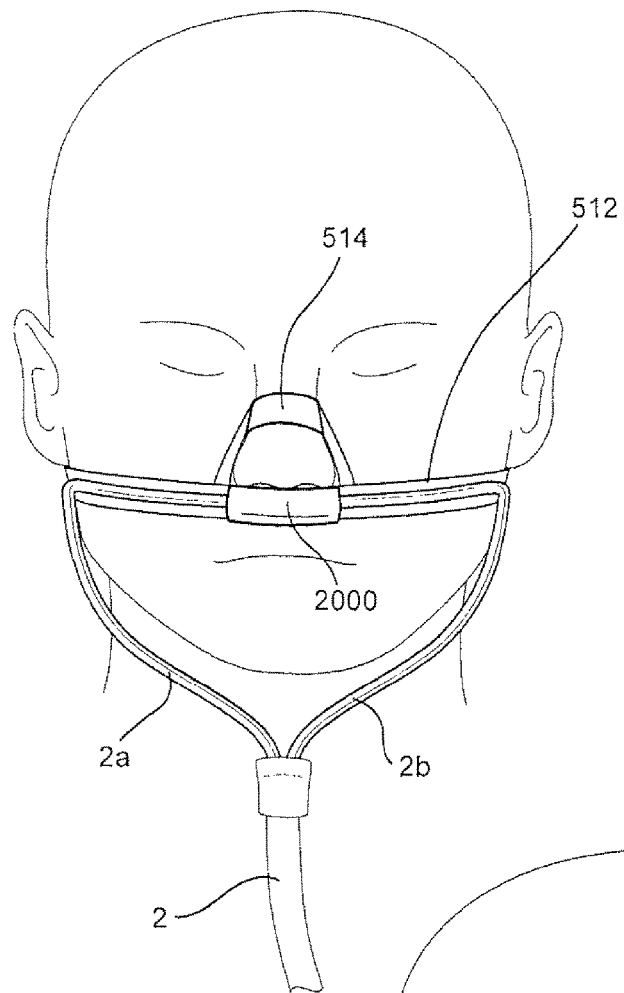
FIGS. 20a and 20b schematically illustrate an interface system according to another sample embodiment.
Figure 20B:
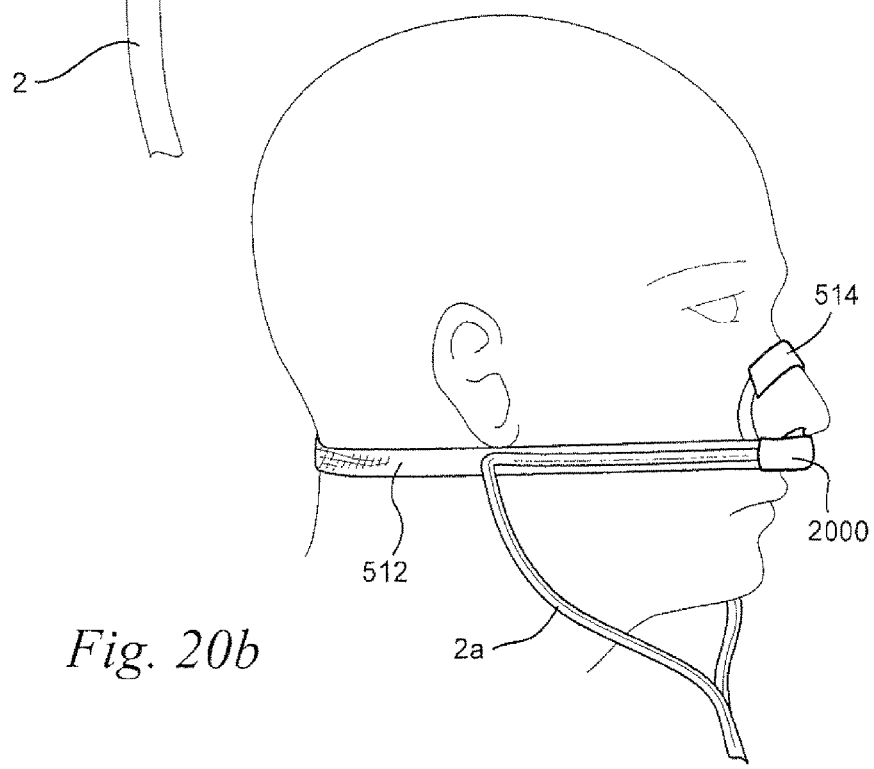

Referring to FIGS. 20a and 20b, the patient interface structure 2000 may be held in position with the patient's nose by a strap 512, for example an elastic strap, that is configured to extend around the patient's head. The strap 512 may extend below the patient's ears, although it should be appreciated that the strap may extend above the patient's ears, or the strap may be bifurcated to include a portion that extends below the patient's ears and a portion that extends above the patient's ears.

A second strap 514 may be connected at opposite ends to the strap 512 and extend across the bridge of the patient's nose. The strap 514 may comprise an adhesive to assist in securing the patient interface structure 2000 in position with the patient's nose, for example when tube drag forces act on the patient interface structure 2000.

The flow of breathable gas may be delivered to the patient interface structure 2000 by a cannula 2 that comprises two cannula branches 2a, 2b that extend along each side of the patient's face. The cannula branches 2a, 2b may be secured to the strap 512 to further reduce the effects of tube drag forces.

1.2.11 Adhesive Fixation Eleventh Embodiment

Referring to FIG. 21, a patient interface structure 2000 is held in position with a patient's nose by a strap 512, e.g. an elastic strap, configured to extend around the patient's head. A second strap 514, which may comprise adhesive, is connected at opposite ends to the strap 512 and extends across the bridge of the patient's nose. A cannula or tube 2 may be connected to the patient interface structure 2000 to deliver a flow of breathable gas to the patient interface structure 2000.

1.2.12 Adhesive Fixation Twelfth Embodiment

Referring to FIGS. 22 and 23, the patient interface structure may comprise a patient interface structure 2000 that may be held in engagement with the face of the patient 1 by adhesive strips 2060. The adhesive strips 2060 are provided on opposite sides of the patient interface structure 2000 and are configured to engage the sides of the nose of the patient 1. As shown in FIGS. 22 and 23, a pair of adhesive strips 2060 is provided to secure the patient interface structure 2000 to the patient 1. Each adhesive strip 2060 may be individually adhered to the patient interface structure 2000 to provide for individual adjustment of the attachment of the adhesive strip 2060 to the face of the patient 1.

1.2.13 Adhesive Fixation Thirteenth Embodiment

Referring to FIGS. 24 and 25, in another sample embodiment of the invention, an adhesive strip 2062 comprises an aperture 2064 that is configured to extend coextensively with the aperture 2006 of the patient interface structure 2000. The hose or tube 2008 is securable to the patient interface structure 2000 through the aperture 2064 of the adhesive strip 2062. The aperture 2064 of the adhesive strip 2062 is configured to loop around either the delivery tube 2008 and/or a sealing ring connecting the tube 2008 to the patient interface structure 2000.

In a variant shown in FIG. 26, the adhesive strip 2066 comprises a semi-circular loop 2068 that is configured to loop around the tube 2008 and/or a sealing ring. As shown in FIG. 26, the loop 2068 extends around the top of the tube 2008, but it should be appreciated that the loop 2068 may extend below the tube 2008.

1.2.14 Adhesive Fixation Fourteenth Embodiment

Referring to FIGS. 27 and 28, an adhesive strip 2070 comprises lateral strips 2072 that are configured to engage the sides of the patient's face, for example the cheeks. A nasal bridge strip portion 2074 is configured to extend along the bridge of the patient's nose and extends to a nasal bridge lateral strip 2076 that is configured to extend laterally across the bridge of the patient's nose. As shown in FIG. 27, the adhesive strip 2070 includes a loop 2071 extending around the top of the delivery tube 2008, but it should be appreciated that the adhesive strip 2070 may include an aperture, similar to the one shown in FIG. 24 and extend completely around the delivery tube 2008.

1.2.15 Adhesive Fixation Fifteenth Embodiment

Figure 29:
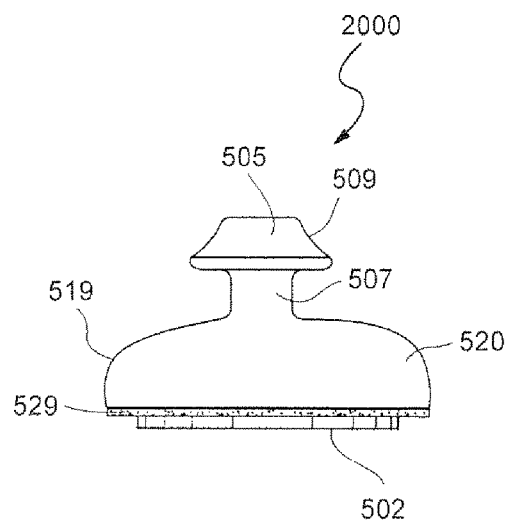
FIG. 29 schematically illustrates a patient interface structure according to another sample embodiment.

Referring to FIG. 29, the patient interface structure 2000 may comprise a pair of nasal pillows 505 (only one shown). Each nasal pillow 505 may comprise a generally cylindrical portion 507 and a conical portion 509 configured to sealingly engage a nare of the patient. The patient interface structure 2000 may include a flexible base portion 519 defining a nasal breathing cavity 520. Such a flexible base portion is disclosed in, for example, International Application PCT/AU2008/001557, filed Oct. 22, 2008, the entire contents of which are incorporated herein by reference. The pair of nasal pillows 505 may be connected to a flow of breathable gas delivered by a tube that is connected to the patient interface structure 2000 by a sealing ring 502. Adhesive 529 may be provided to the bottom of the base portion 519 to allow the cushion 504 to connect to a strap in a manner similar to that described above.

The nasal pillows may be as disclosed, for example, U.S. Patent Application Publications 2007/0144525 A1 and 2006/0283461 A1, and International Application PCT/AU2008/001557, filed Oct. 22, 2008, the entire contents of each being incorporated herein by reference. It should also be appreciated that the nasal pillows may be as described in, for example, U.S. Pat. No. 7,318,437, the entire contents of which are incorporated herein by reference. It should further be appreciated that in addition to nasal pillows, the patient interface structure may include nasal pillows or prongs as disclosed, for example, in U.S. Pat. No. 4,782,832 (Trimble), U.S. Pat. No. 7,201,169 (Wilkie et al.), U.S. Pat. No. 7,059,328 (Wood), and WO 2000/074758 (Lovell). It should also be appreciated that the cannula(e) and/or nasal pillows or prongs may include features configured to diffuse the flow of air so that noise may be reduced. Such features are disclosed in, for example U.S. Patent Application Publication 2009/0044808 A1, and WO 2008/014543 A1, the entire contents of each being incorporated herein by reference.

1.2.16 Adhesive Fixation Sixteenth Embodiment

Figure 30:
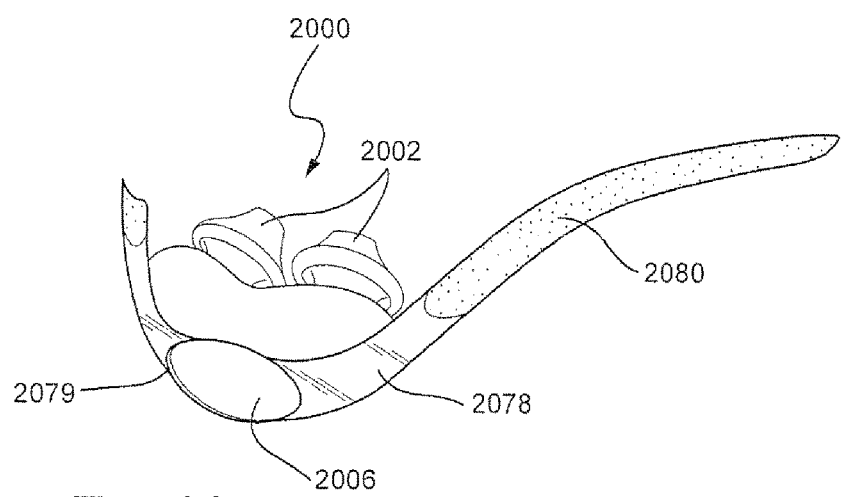
FIG. 30 schematically illustrates an interface system according to another sample embodiment.

Referring to FIG. 30, the patient interface structure 2000 may be supported by a frame 2078 that is, for example, formed of a clear, or transparent, flexible material. The frame 2078 comprises an aperture 2079 that is configured to be coextensive with the aperture 2006 of the patient interface structure 2000. The frame 2078 also comprises adhesive 2080, for example an adhesive strip, that is configured to adhesively secure the frame 2078 to the face of the patient.

1.2.17 Adhesive Fixation Seventeenth Embodiment

Figure 31:
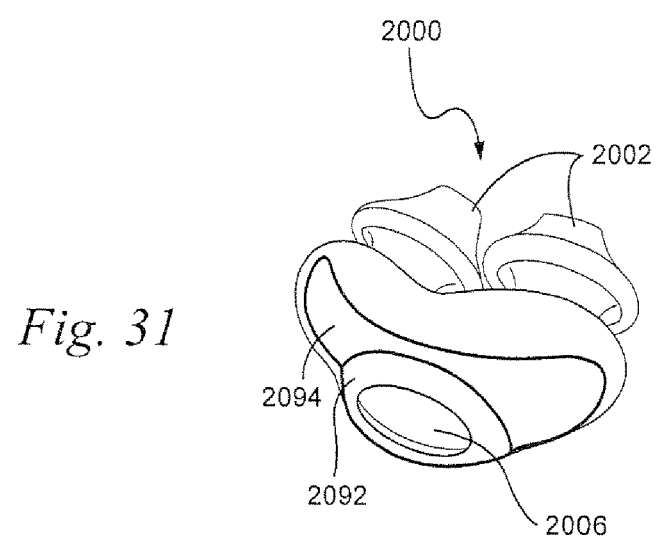
FIG. 31 schematically illustrates an interface system according to another sample embodiment.
Figure 32:
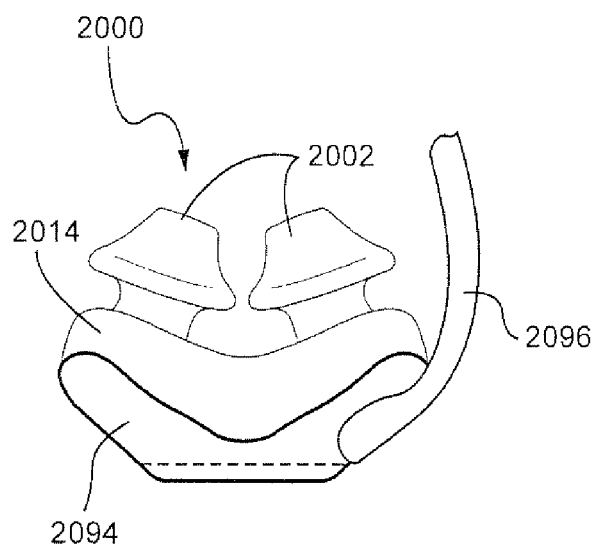
FIGS. 32 and 33 schematically illustrates an interface system according to another sample embodiment.
Figure 33:
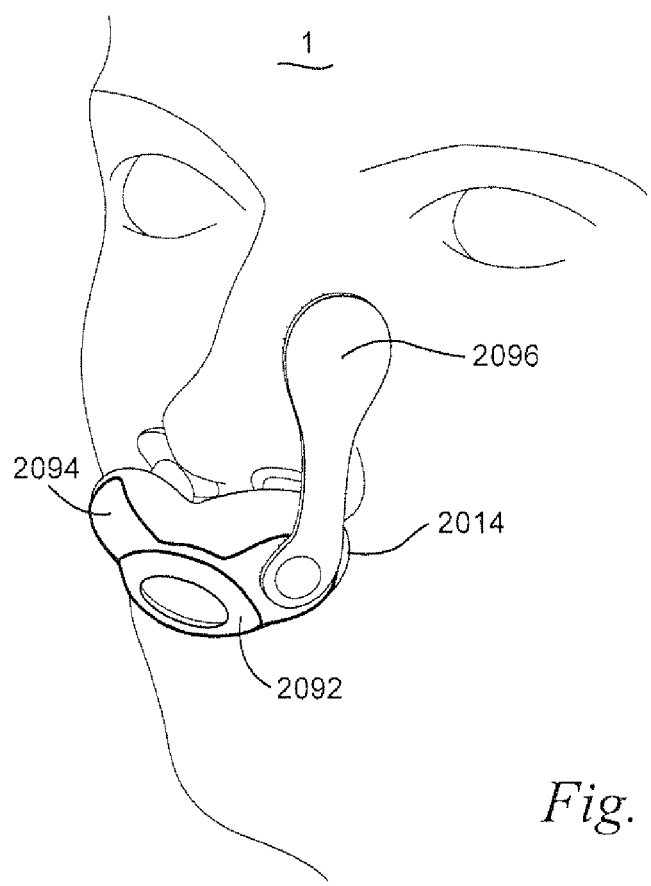

Referring to FIGS. 31-33, the patient interface structure 2000 may be connected to a sealing ring 2092 that is configured to connect a delivery tube or conduit to the patient interface structure 2000. The sealing ring 2092 may comprise a shroud 2094 that is configured to extend along the flexible base portion 2014 of the patient interface structure 2000. As shown in FIG. 33, adhesive strips 2096 (only one shown) may be secured to the shroud 2094 and to the patient's face, for example, along the sides of the patient's nose, to secure the patient interface structure 2000 in sealing engagement with the patient's airways.

1.2.18 Adhesive Fixation Eighteenth Embodiment

Referring to FIG. 34, the patient interface structure 2000 may be connected to a stiffening element, or rigidizer, 2098 that is secured to the face of the patient by adhesive 2100. The stiffening element or rigidizer 2098 may be formed, for example, of non-silicone, and the adhesive may be chosen for securing a non-silicone component. It should also be appreciated that the adhesive may be used to join other non-silicone components to the patient's face, for example, a sealing ring or headgear.

1.2.19 Adhesive Fixation Nineteenth Embodiment

As shown in FIG. 35, the patient interface structure 2000 may comprise connectors 2102 extending from opposite sides. The connectors 2102 may comprise a hinge 2106 which may be formed by a portion of the connectors 2102 that has been reduced in thickness. The ends of the connectors 2102 may comprise adhesive 2104 which may be a tacky gel that is co-molded or otherwise integrated with the connectors 2102. The tackiness of the gel adhesive 2104 will cause the gel to adhere to the face of the patient thus securing the nasal prongs or pillows 2002 of the patient interface structure 2000 in sealing engagement with the patient.

1.2.20 Adhesive Fixation Twentieth Embodiment

Referring to FIG. 36, the nasal prongs or pillows 2002 of the patient interface structure 2000 may be provided with adhesive 2108 that may be, for example, a tacky gel co-molded with the patient interface structure 2000. The adhesive 2108 is thereby provided at the sealing interface of the patient interface structure 2000. As shown in FIG. 37, in addition to the adhesive 2108 provided on the nasal prongs or pillows 2002, additional adhesive 2110, in the form of tacky gel for example, may be provided on the flexible base portion 2014 of the patient interface structure 2000 in a location that does not form a sealing engagement with the face of the patient. The adhesive 2110 may thus adhere to, for example, the upper lip and/or cheeks of the patient.

Figures 38, 39:
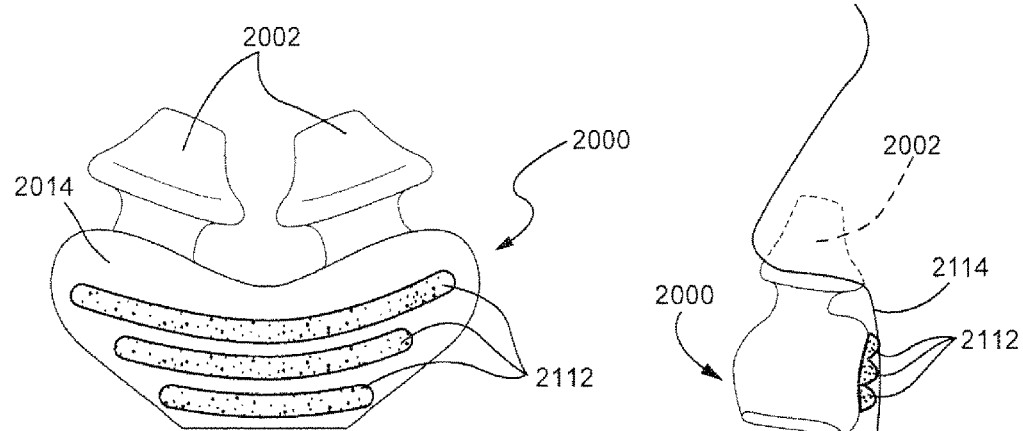
FIGS. 38 and 39 schematically illustrate a patient interface structure according to another sample embodiment.

Referring to FIGS. 38 and 39, adhesive 2112, which may be a co-molded tacky gel, on the base portion 2014 of the patient interface structure 2000 is configured to adhesively secure the patient interface structure 2000 to the upper lip 2114 of the patient.

1.2.21 Adhesive Fixation Twenty—First Embodiment

Figure 40:
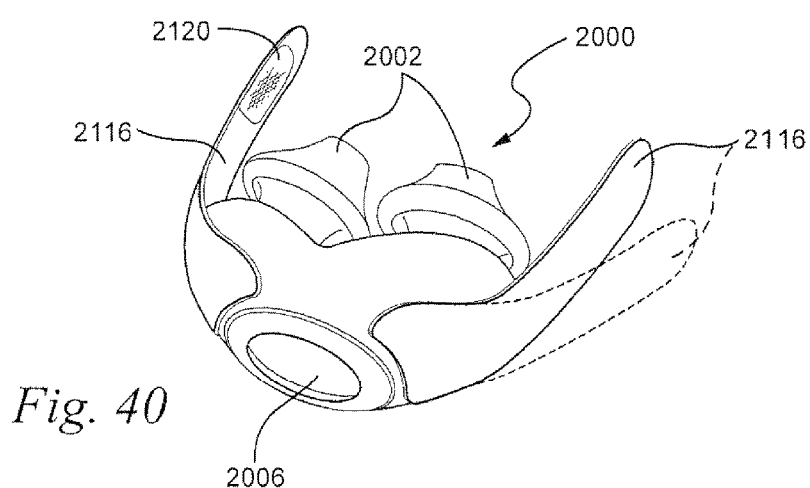
FIGS. 40 and 41 schematically illustrate an interface system according to another sample embodiment.
Figure 41:
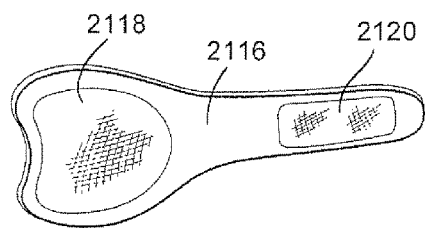
Figure 42:
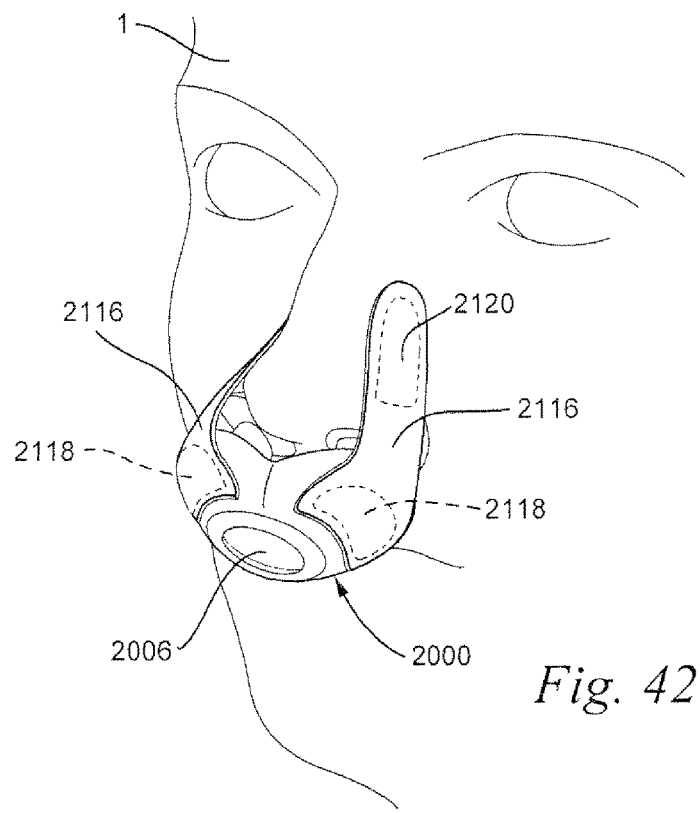
FIGS. 42-44 schematically illustrate an interface system according to another sample embodiment of the invention.

Referring to FIGS. 40-42, the patient interface system may comprise adhesive strips 2116 that are adhesively securable to the patient interface structure 2000. As shown in FIG. 41, the adhesive strips 2116 may comprise adhesive divided into two portions. An adhesive 2118 is configured for securing the adhesive strips 2116 to the patient interface structure 2000 which may be formed of, for example, of silicone material. The adhesive strips 2116 may also comprise an adhesive 2120 that is configured to adhesively secure to the skin of the patient. The adhesive 2120 for securing the interface structure 2000 to the skin of the patient may be, for example, a synthetic rubber (e.g. hydrocolloid).

The adhesive 2120 may releasably adhere the strips 2116 to the face of the patient to permit adjustment of the fit of the patient interface structure 2000 to the face of the patient, as shown in FIG. 40.

1.2.22 Adhesive Fixation Twenty—Second Embodiment

Figure 43:
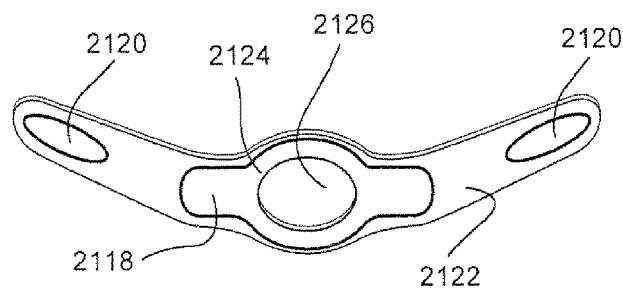
Figure 44:
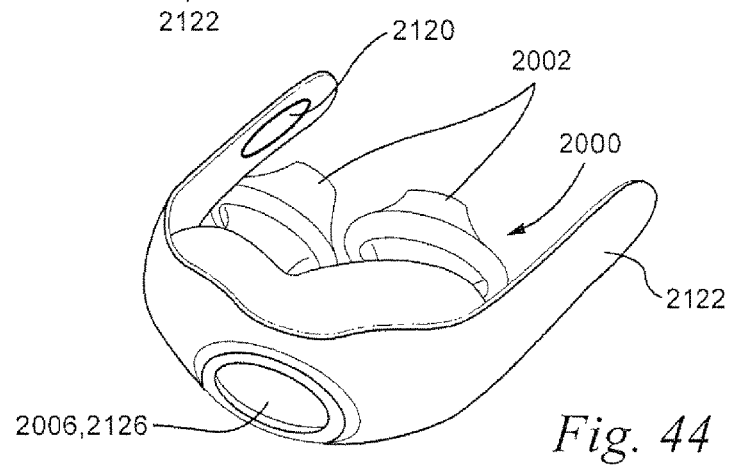

Referring to FIGS. 43 and 44, in another sample embodiment of the invention, the patient interface structure 2000 is adhesively secured to an adhesive strip 2122 that includes a loop 2124 comprising an aperture 2126 that is configured to be coextensive with the aperture 2006 of the patient interface structure 2000 when the adhesive strip 2122 is secured to the patient interface structure 2000. The loop 2124 is provided with adhesive 2118 that is configured to adhere to, for example, the silicone material of the patient interface structure 2000. The ends of the adhesive strip 2122 may comprise adhesive 2120 that is configured to adhere to the skin of the patient.

Although the patient interface systems shown in FIGS. 40-44 show one or two adhesive strips provided to the system, it should be appreciated that multiple adhesive strips may be provided, for example three or four. Each adhesive strip of the system may be provided with two adhesive regions, i.e. a patient interface structure engaging adhesive and a patient, or skin engaging, adhesive.

1.2.23 Adhesive Fixation Twenty—Third Embodiment

Figure 45:
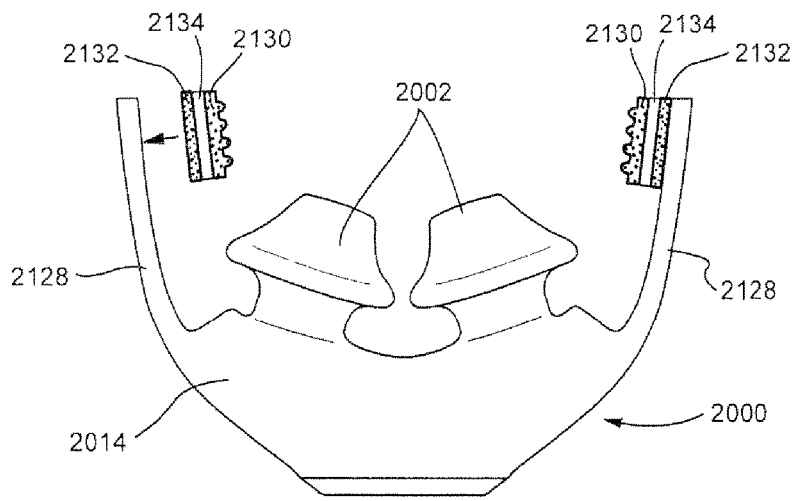
FIGS. 45-47 schematically illustrate an interface system according to another sample embodiment.
Figure 46:
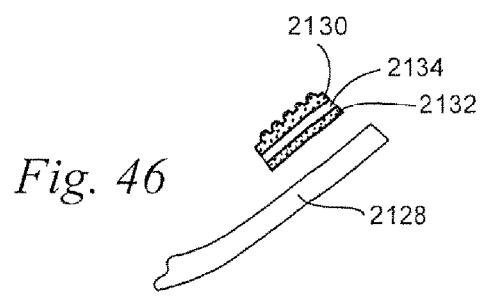
Figure 47:
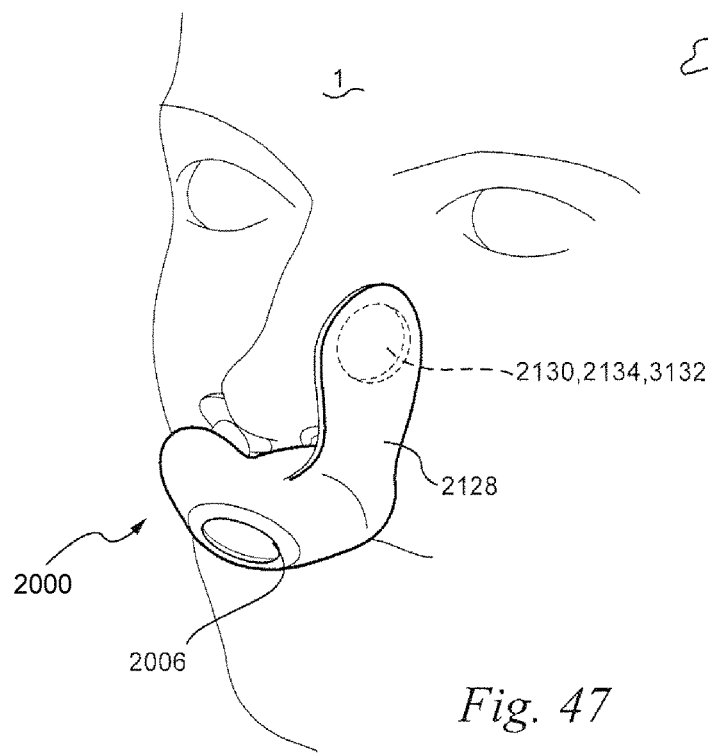

Referring to FIGS. 45-47, the patient interface structure 2000 may comprise connector strips 2128 extending from opposite sides. The connector strips 2128 may be integrally formed with the patient interface structure 2000, or separately provided and secured to the patient interface structure 2000. The ends of the connector strips 2128 may comprise double sided adhesive strips 2130, 2132. The double sided adhesive strip 2132 may comprise adhesive that is configured to secure to the material of the connector strips 2128, which may be formed, for example, of silicone. The double sided adhesive strips 2130 may comprise adhesives that are configured to secure the connector strips 2128 to the skin of the patient. The adhesive strips 2130 may be, for example, synthetic rubber.

An intermediate portion 2134 may be provided between the double sided adhesive strips 2130, 2132 to form an impermeable barrier and prevent contamination of each double sided adhesive strip 2130, 2132. It should be appreciated, however, that the double sided adhesive strips 2130, 2132 may be bonded together without an intermediate portion therebetween or that a single double sided adhesive strip may be provided to each connector strip 2128.

2.0 Positioning and Stabilizing Using Adhesive and Additional Fastening Arrangements It may be desirable to provide fastening arrangements in addition to adhesive for positioning and stabilizing the patient interface structure in engagement with the patient's face. The use of additional fastening arrangements, or materials, permit the position of the patient interface structure and/or the position of the fastening arrangement to be adjusted to provide a comfortable fit while providing efficient therapy via the flow of breathable gas.

2.1.1 Adhesive and Hook and Loop Fastening Material First Embodiment

Referring to FIGS. 48 and 49, an adhesive strip 2136 may comprise hook or loop fastener material 2138 on an opposite side to the adhesive layer such that the hook or loop fastener material 2138 may be on the non-patient contacting side of the adhesive strip 2136. The adhesive strip 2136 may be applied to the face of the patient, for example, across the nasal bridge or cheeks, with the hook or loop fastener material 2138 provided to the top of the strip 2136. A frame or support 2140 may engage the patient interface structure 2000, which may comprise a flexible base portion and a pair of nasal pillows or prongs. The frame or support 2140 comprises corresponding loop and hook fastener material 2142 configured to engage the hook and loop fastener material 2138 of the adhesive strip 2136 to secure the patient interface structure 2000 in sealing engagement with the patient's airways.

As shown in FIG. 48, the hook or loop fastener material 2138 is provided at opposite portions of the strip 2136. It should be appreciated that the hook and loop fastener material may be continuous across the adhesive strip 2136, or may be provided in zones or areas of the adhesive strip 2136.

The frame or support 2140 may be connected to the patient interface structure 2000 by any method, for example, gluing, co-molding or interference fit. It should also be appreciated that the hook and loop fastener material 2138, 2142 may be formed of any material, such as metal or plastic.

2.1.2 Adhesive and Hook and Loop Fastening Material Second Embodiment

Figure 50B:
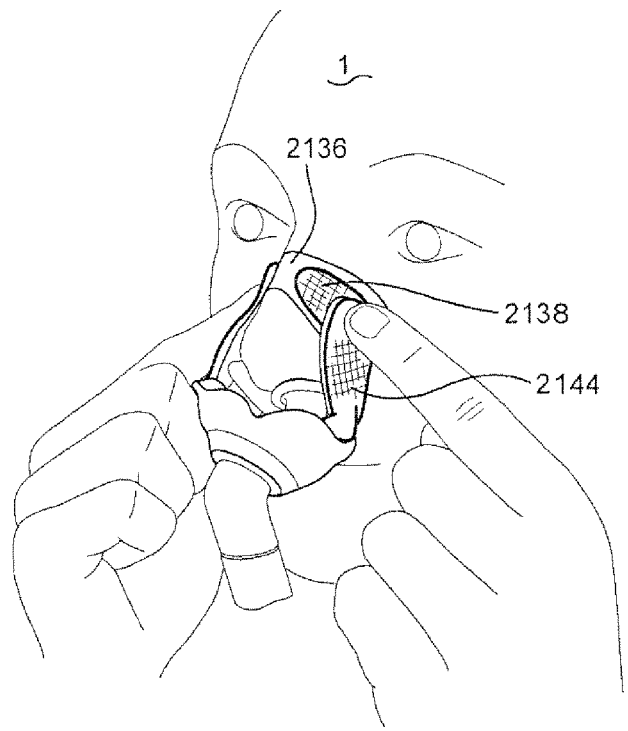
Figure 50C:
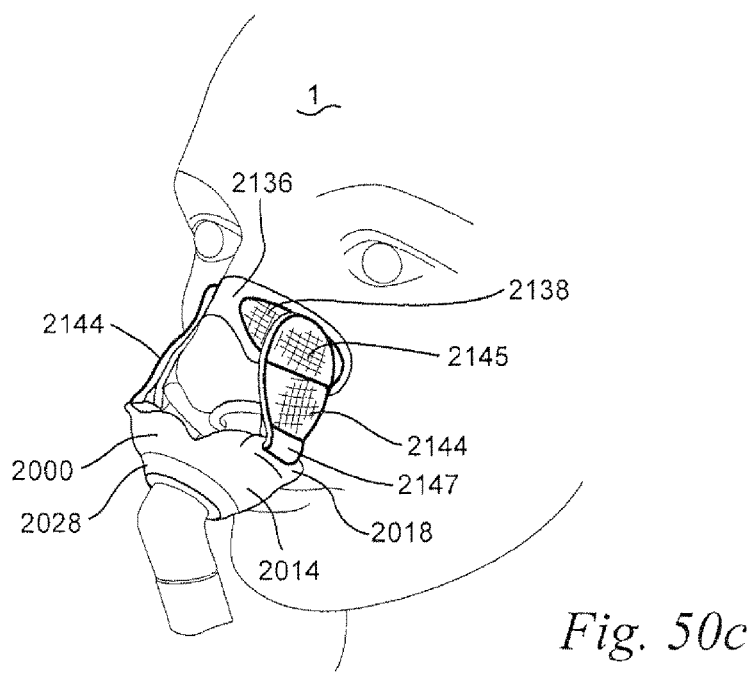

Referring to FIGS. 50a-50c, the patient interface structure 2000 may comprise connector strips 2144 provided at opposite ends. The connector strips 2144 may comprise hook or loop fastener material 2145 that is securable to the loop or hook fastener material 2138 of the adhesive strip 2136. The connector strips 2144 may be connected to the patient interface structure 2000 through, for example, loops 2018, 2147, as described above. For example, the loops 2018 may be integrally formed on opposite sides of the flexible base portion 2014 of the patient interface structure 2000. As another example, the connector strips 2144 may be connected to a sealing ring 2028 or a swivel elbow connected to the patient interface structure 2000.

As shown in FIGS. 48-50c, the adhesive strip 2136 may include a region in which no fastener material and/or adhesive is provided. For example, the portion of the adhesive strip 2136 between the fastener materials 2138 may not be provided with fastener material and/or adhesive. The adhesive strip 2136 may also include a peripheral region that does not include fastener material and/or adhesive, for example as shown in FIG. 48 that permits the adhesive strip to be engaged by the patient's or clinician's fingers to facilitate removal of the support 2140 or the connectors 2144 from the adhesive strip 2136 and/or to facilitate removal of the adhesive strip 2136 from the patient's face.

2.1.3 Adhesive and Hook and Loop Fastening Material Third Embodiment

Figure 51A:
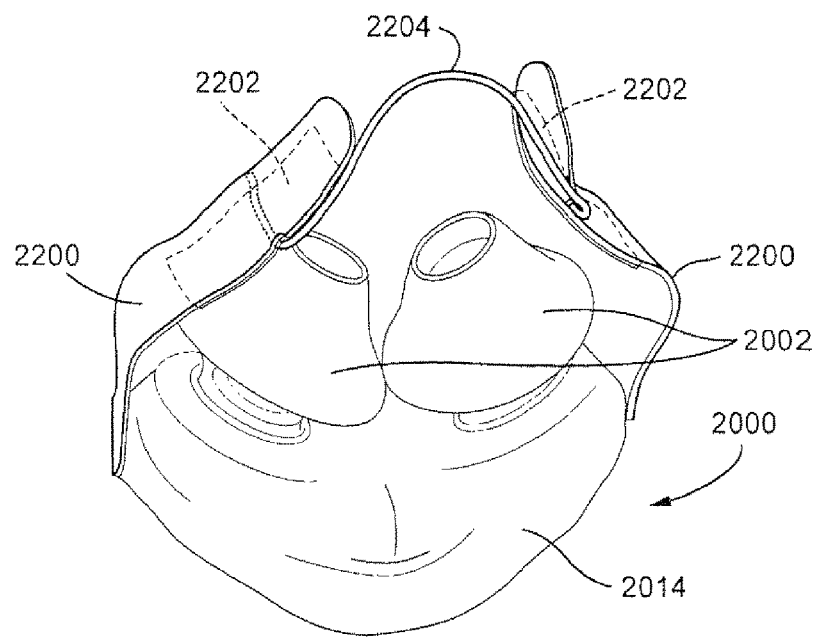
FIGS. 51a and 51b schematically illustrate an interface system according to another sample embodiment.
Figure 51B:
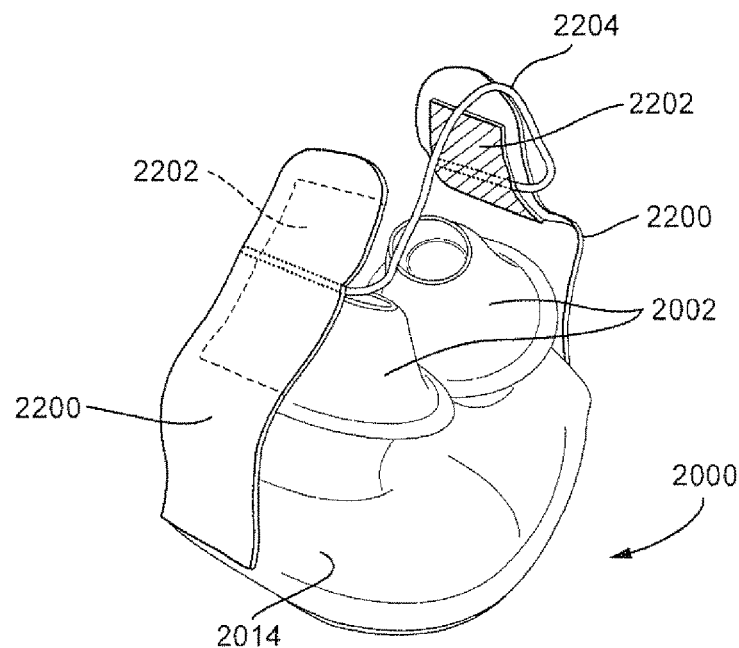

Referring to FIGS. 51a and 51b, a patient interface structure 2000 includes a flexible base portion 2014 and connectors 2200 provided on each side of the flexible base portion 2014. The connectors 2200 may each comprise hook material 2202 provided thereon. The hook material 2202 may be provided on an adhesive strip that is adhered to the connector 2200. It should be appreciated, however, that the hook material may be attached to the connectors 2200 by other mechanisms.

The hook material 2202 is configured to engage with loop material provided on an adhesive nasal strip (not shown, but may be similar to, for example, the adhesive strip 2136 shown in FIGS. 5a-50c) that is configured to be placed across the bridge of the patient's nose. It should also be appreciated that the connectors 2200 may have the loop material provided thereon and the adhesive nasal strip may have hook material provided thereon.

A wire 2204 may be connected between the connectors 2200. For example, the ends of the wire 2204 may be connected to the connectors 2200 by adhesive strips on which the hook material 2202 is provided. The wire 2204 may be preloaded to force the patient's nostrils to flare outwards when the hook material 2202 is connected to the loop material of the adhesive nasal strip that is adhered across the bridge of the patient's nose.

The wire may be formed, for example, of metal and may be connected to the loop or hook material 2202 by adhesive or co-molding, or any other mechanism.

2.1.4 Adhesive and Hook and Loop Fastening Material Fourth Embodiment

Figure 52A:
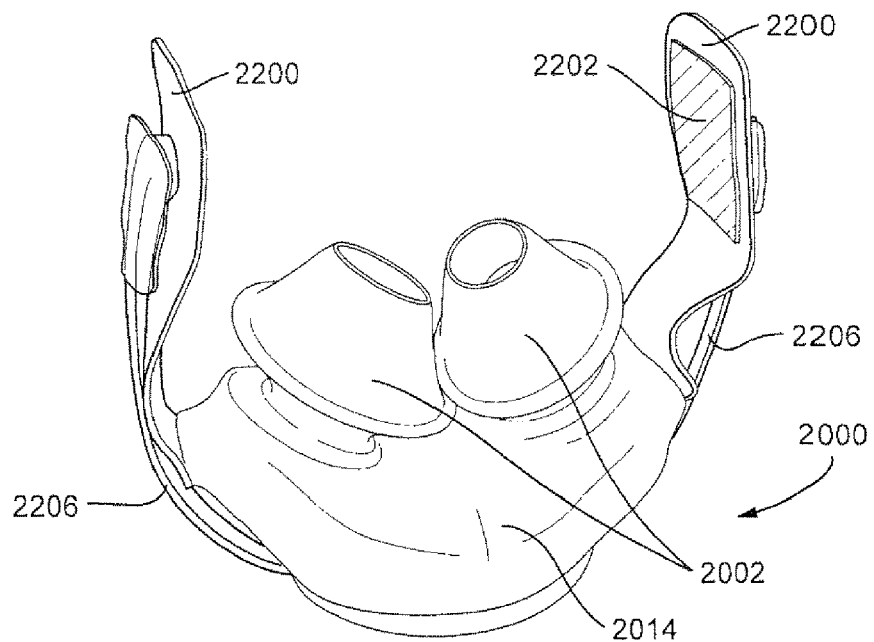
FIGS. 52a and 52b schematically illustrate an interface system according to another sample embodiment.
Figure 52B:
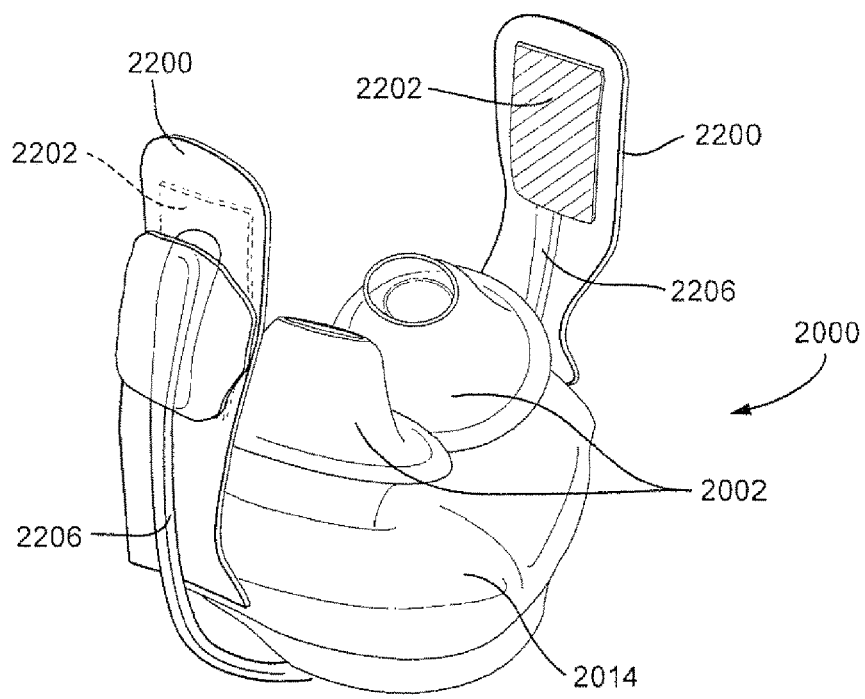

Referring to FIGS. 52a and 52b, the patient interface structure 2000 may comprise the flexible base portion 2014 and a pair of stiffening members 2206 that connect to the flexible base portion 2014 and extend along the connectors 2200 that include the hook material 2202. The stiffening members 2206 may be configured to provide an outward bias to the connectors 2200 to force the patient's nostrils to flare outwards when the hook material 2202 is connected to the loop material of the adhesive nasal strip across the bridge of the patient's nose. The stiffening members 2206 may be formed of, for example, metal, TPE, polycarbonate, polypropylene, and may be connected to the connectors 2200 by, for example, adhesive or co-molding.

2.1.5 Adhesive and Hook and Loop Fastening Material Fifth Embodiment

Figure 53:
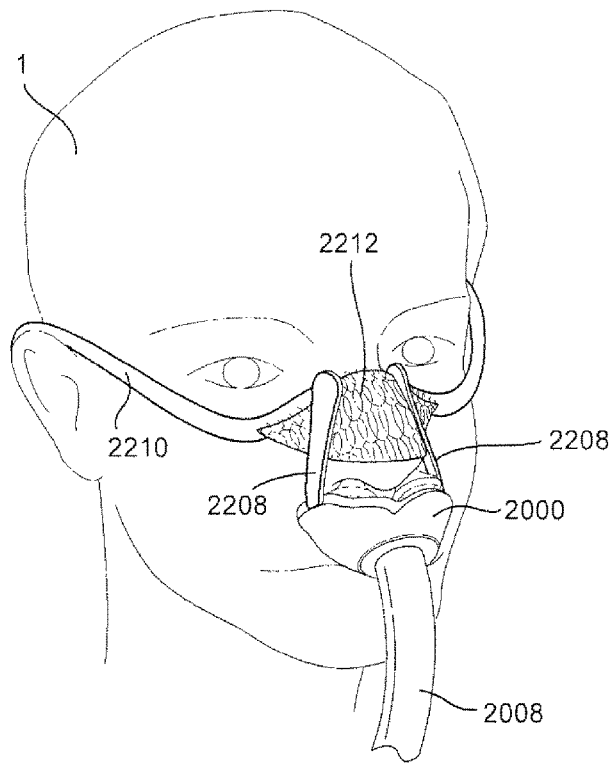
FIG. 53 schematically illustrates an interface system according to another sample embodiment.

Referring to FIG. 53, the patient interface structure 2000 may be held in engagement with the nares of the patient by connectors 2208 that are fastened to a nose cap 2212 that is held across the patient's nose by a head strap 2210. The nose cap 2212 may include loop material that fastens with hook material provided on the connectors 2208, or vice versa.

The head strap 2210 loops around the patient's head and hooks over the patient's ears to avoid the patient's eyes. The nose cap 2212 may be configured to cover all, or part, of the patient's nose. The head strap 2210 and/or the nose cap 2212 may be made from a rigid material, or a flexible material (e.g. TPE), or a combination of rigid and flexible material.

It should be appreciated that the connectors 2208 may connect to the nose cap 2212 by other fastening mechanisms, for example, magnetic or electrostatic.

2.1.6 Adhesive and Hook and Loop Fastening Material Sixth Embodiment

Figure 57:
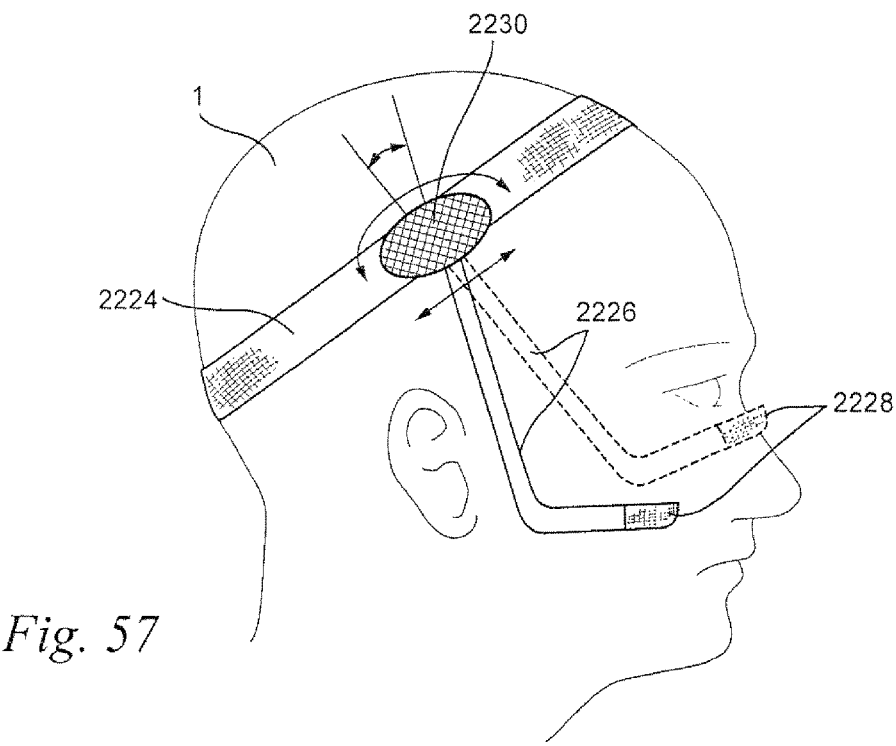
FIG. 57 schematically illustrates an interface system according to another sample embodiment.

Referring to FIG. 57, a patient interface system may comprise a head strap 2224 that is configured to extend around the head of the patient. The head strap 2224 may comprise an adjustment mechanism 2230, for example, a hook or loop fastening material. A stiffening element, or rigidizer, 2226 may be connected to the adjustment mechanism 2230, for example, by respective loop or hook fastening material. The rigidizer 2226 may be rotated or slid along the head strap 2224 to allow adjustment of the position of the rigidizers 2226. Each rigidizer (only one shown in FIG. 57) may comprise connectors 2228 configured to connect to a patient interface structure that engages with the nose of the patient, for example, by being connected to connectors provided to the patient interface structure. The connectors 2228 may be hook or loop fastening material, magnetic, or electrostatic connecting mechanisms.

2.1.7 Adhesive and Hook and Loop Fastening Material Seventh Embodiment

Figure 59A:
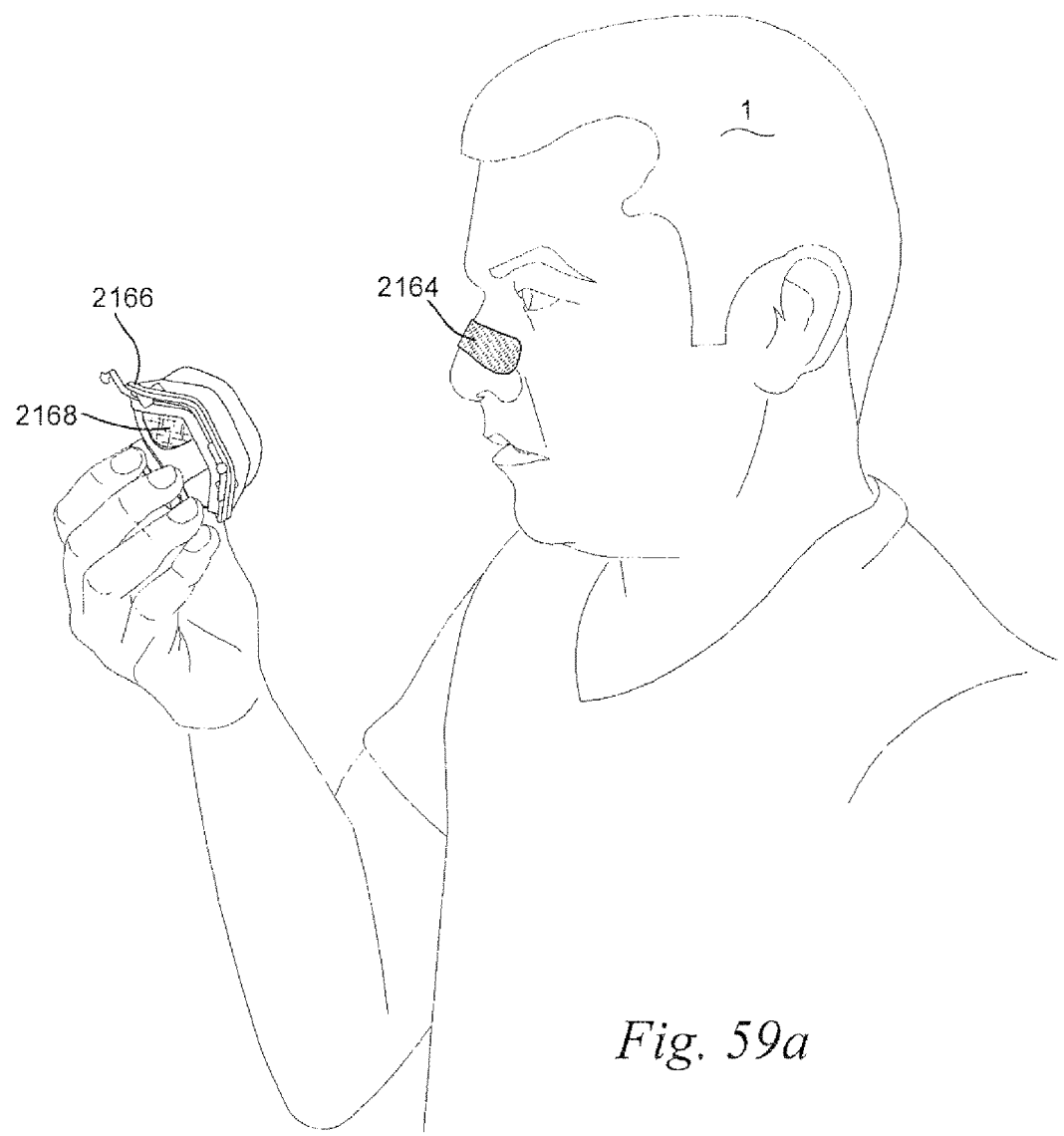
FIGS. 59a and 59b schematically illustrate an interface system according to another sample embodiment.
Figure 59B:
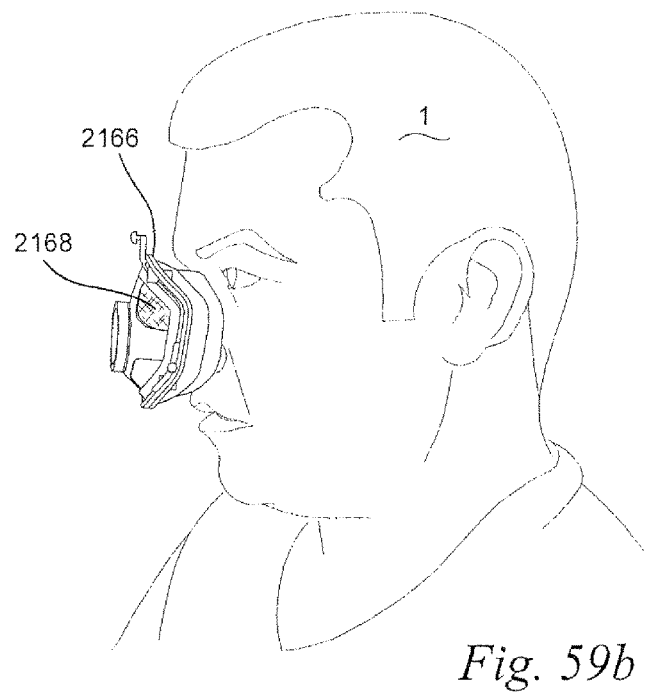

Referring to FIGS. 59a and 59b, an adhesive strip 2164 comprising hook fastener material may be secured to, for example, the bridge of the patient's nose. A patient interface 2166, for example a nasal mask which may comprise a mask frame and a cushion, may be provided with loop fastener material 2168 on an interior portion thereof for engagement with the hook fastener material of the adhesive strip 2164. As shown in FIG. 59b, the patient secures the nasal mask 2166 in sealing engagement by securing the loop fastener material 2168 of the nasal mask 2166 with the hook fastener material of the adhesive strip 2164.

The loop fastener material 2168 is placed on the inner surface of the frame of a nasal mask, for example at the nasal bridge region. The loop fastener material 2168 in the frame of the nasal mask 2166 may need to be 'built up' or thickened so as to contact the patient's nose where the adhesive strip 2164 with corresponding hook fastener material is attached.

It should also be appreciated that the configuration shown is not the only possible location for attachment of the hook and loop materials. For example, the mask may be a full face mask and the adhesive strip(s) 2164 may be provided in, for example, the cheek region, the upper lip region, and/or a chin region. The hook and loop materials may also be in the reversed configuration, i.e. hook fastener material inside the mask and loop fastener material on the adhesive strip.

The embodiments shown in FIGS. 48-53, 57 and 59*a*-59*b* include hook and loop fastener material. However, it should be appreciated that other forms of attachment may be used, for example magnets. The magnets may be provided to the adhesive strip and/or the frame or support and/or the connector strips 2144. The magnets may be connected by any method, for example gluing, welding, co-molding, or an interference fit.

The adhesive strip 2164 may be configured to extend across the bridge of the patient's nose but avoid the soft skin under the eyes. The adhesive strip 2164 may also be configured to not extend along the creases where the nose meets the sides of the patient's cheeks. The adhesive strip 2164 may also be configured not to cover areas of the patient's face that move. The adhesive strip 2164 may have an area that is large enough to assemble the patient interface structure to the adhesive strip and maintain the connection between the hook and loop fastener materials.

2.1.8 Adhesive and Hook and Loop Fastening Material Eighth Embodiment

Referring to FIGS. 78-81, a patient interface system includes a patient interface structure 6000 having connectors 6002 on opposite sides. The connectors 6002 may be integrally formed with the patient interface structure 6000, although it should be appreciated that they may be separately provided and attached to the patient interface structure 6000. A flow of breathable gas is delivered through a tube, or conduit, 2008 that is connected to the patient interface structure 6000 by an elbow 6006. The patient interface structure 6000 is secured to the patient in sealing engagement with the patient's airways by an adhesive strip 6004 that is configured to be connected with the connectors 6002. The connector 6002 may have hook fastening material 6008 that engage loop fastening material on the adhesive strip 6004. As shown in FIGS. 80 and 81, the hook fasteners 6008 may be secured to the connector 6002 by, for example, ultrasonic welding the hook fastener 6008 to the connector 6002. A backing pad 6010 may be provided on the opposite side of the connector 6002 to allow the hook fastener 6008 to be ultrasonically welded to the connectors 6002, i.e. to prevent damaging the hook fasteners.

2.1.9 Adhesive and Hook and Loop Fastening Material Ninth Embodiment

Referring to FIGS. 82-84, in another sample embodiment, the patient interface structure 6000 may be held in sealing engagement with the patient's airways by connectors 6014 that are connected to the elbow 6012. The ends 6020 of the connectors 6014 may include hook fasteners that engage loop fasteners provided on an adhesive strip 6004 that is adhered across the bridge of the patient's nose. As shown in FIG. 84, the hook fastener 6016 may be connected to the ends 6020 of the connector 6014 by, for example, ultrasonic welding. The connector 6014 may include living hinges 6018 that allow the ends 6020 of the connector 6014 to extend around the patient interface structure 6000 and engage the adhesive strip 6004.

2.1.10 Adhesive and Hook and Loop Fastening Material Tenth Embodiment

As shown in FIGS. 85-87, a patient interface system according to another sample embodiment includes a patient interface structure 6000 configured to sealingly engage the airways of the patient, e.g. the nares. The patient interface structure 6000 may include nasal puffs or pillows or prongs that are configured to engage the nares of the patient. Connectors 6022 are connected to the patient interface structure 6000 by retention portions 6024 that secure the ends of the connector 6022 to the patient interface structure 6000. The patient interface structure 6000 may include slots through which the connector 6022 may be inserted until the retention portions 6024 engage the patient interface structure 6000. As shown in FIG. 87, the connectors 6022 include hook fasteners 6026 that are connected to the connectors by, for example, ultrasonic welding. The connectors 6022 may be formed of, for example, fabric. The retention portions 6024 of the connectors 6022 may be formed by heat.

2.1.11 Adhesive and Hook and Loop Fastening Material Eleventh Embodiment

Figure 135:
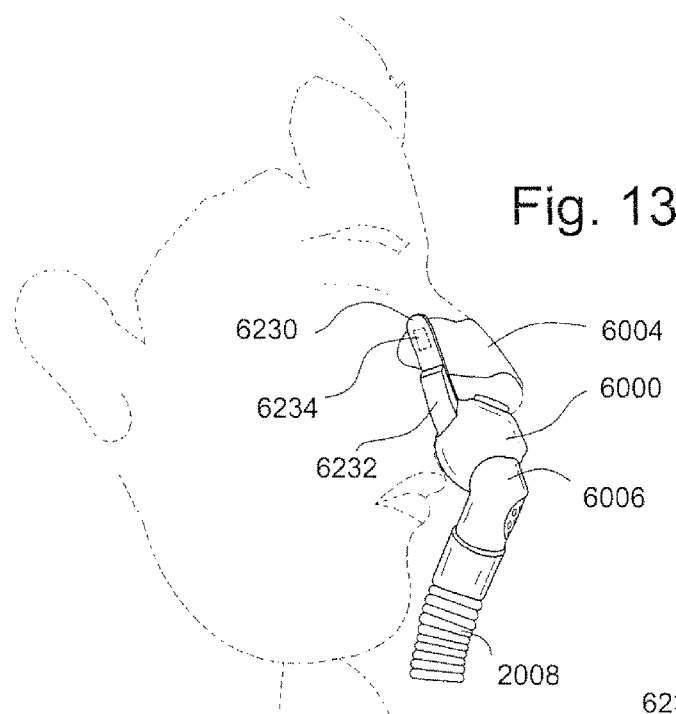
FIGS. 135-137 schematically depict a patient interface system according to another sample embodiment.
Figure 137:
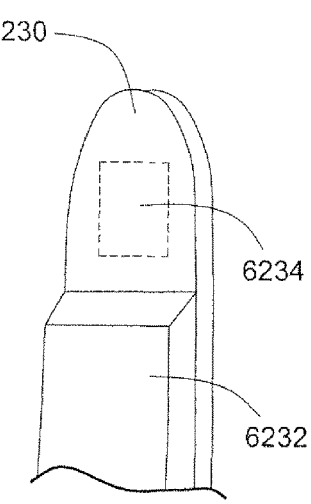
Figure 136:
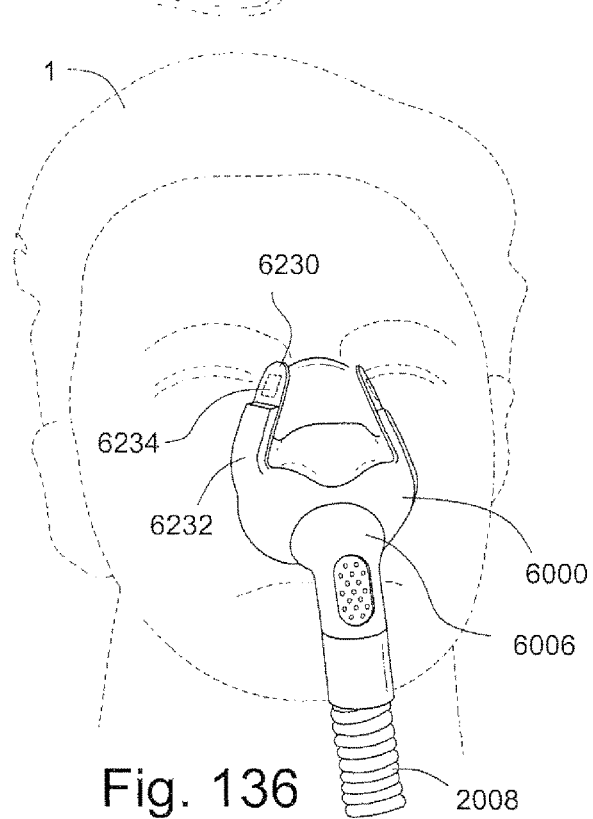

Referring to FIGS. 135-137, the patient interface structure 6000 may be connected to a tube 2008 for delivering a flow of breathable gas by an elbow 6006. The patient interface structure 6000 may also comprise connectors 6230 that include hook fasteners 6234 that engage loop fasteners provided on an adhesive strip 6004 that is adhered to the patient's nose. The connectors 6230 may include a thickened portion 6232 that reduce the torsional force translated to the end of the connector 6230 that includes the hook fasteners 6234.

2.1.12 Adhesive and Hook and Loop Fastening Material Twelfth Embodiment

Figure 138:
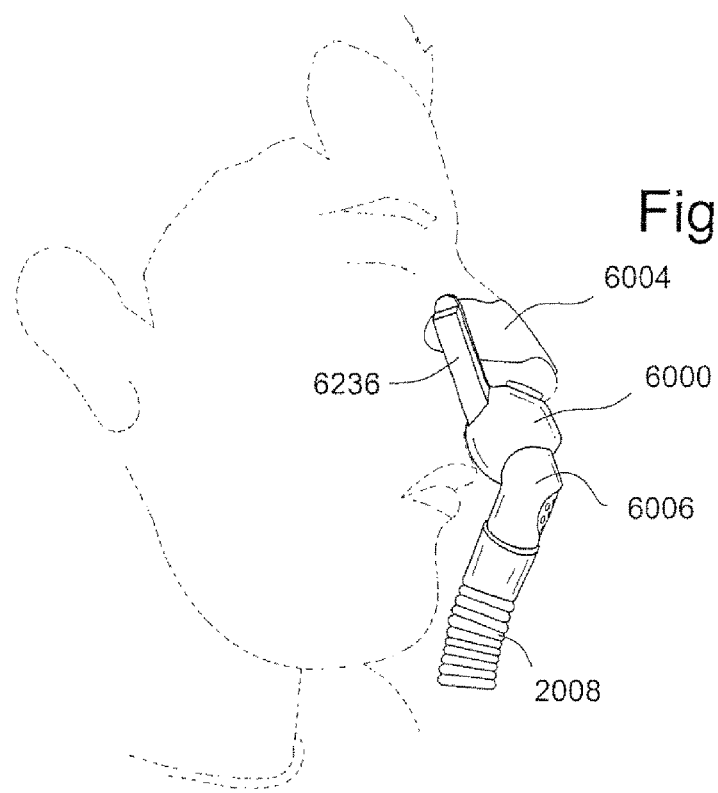
FIGS. 138 and 139 schematically depict a patient interface system according to another sample embodiment.
Figure 139:
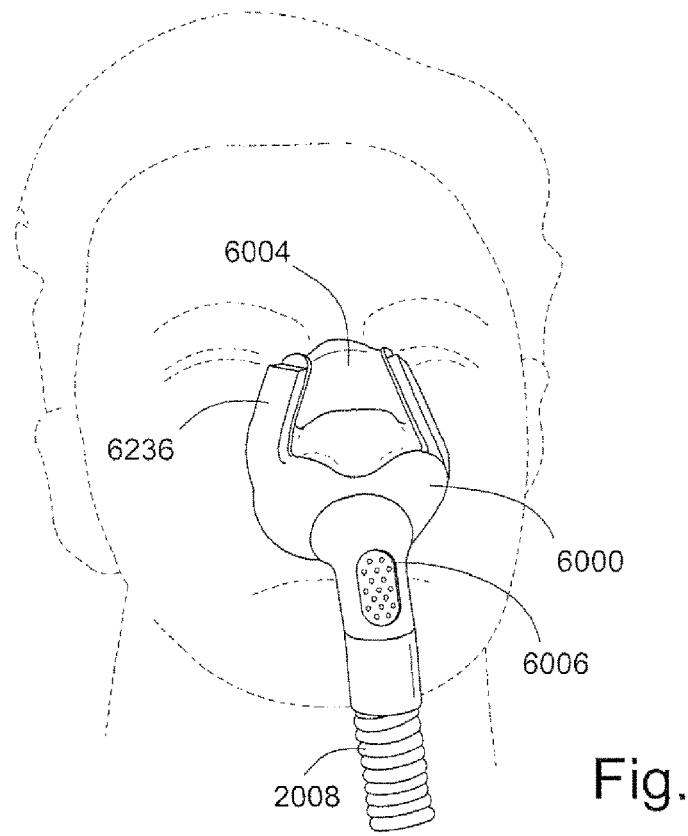

Referring to FIGS. 138 and 139, the connectors 6236 may be thickened throughout the entire length of the connector 6236. The connectors 6236 may be stiffer than other sample embodiments disclosed herein but may provide a more secure feeling to the patient.

2.1.13 Adhesive and Hook and Loop Fastening Material Thirteenth Embodiment

Figure 140:
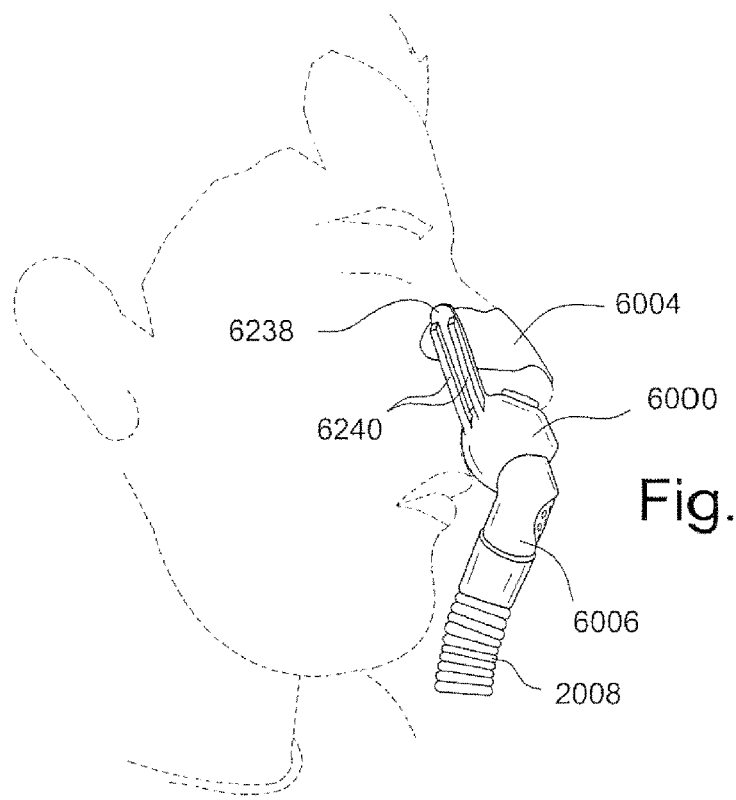
FIGS. 140 and 141 schematically depict a patient interface system according to another sample embodiment.
Figure 141:
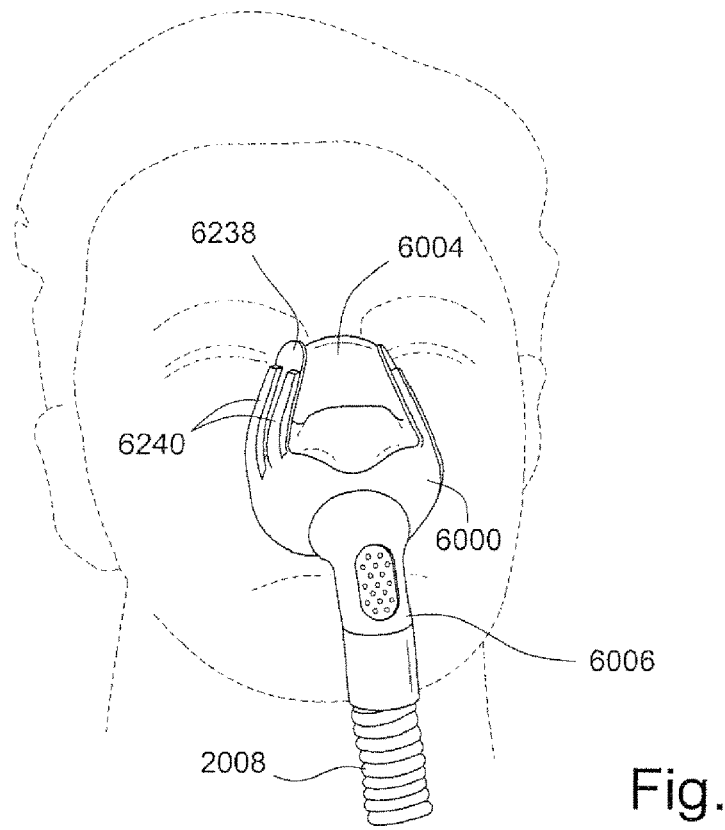

Referring to FIGS. 140 and 141, the connectors 6238 of the patient interface structure 6000 may include ridges 6240 on edges of the connectors 6238 that provide stiffening of the connectors 6238. The ridges 6240 allow the connectors 6238 to twist about a longitudinal axis of the connector 6238 to adapt the fit to the nose of the patient, but provide a stiffer feeling in a direction perpendicular to the longitudinal direction of the connector 6238 along the sides of the patient's nose.

2.1.14 Adhesive and Hook and Loop Fastening Material Fourteenth Embodiment

Figure 142:
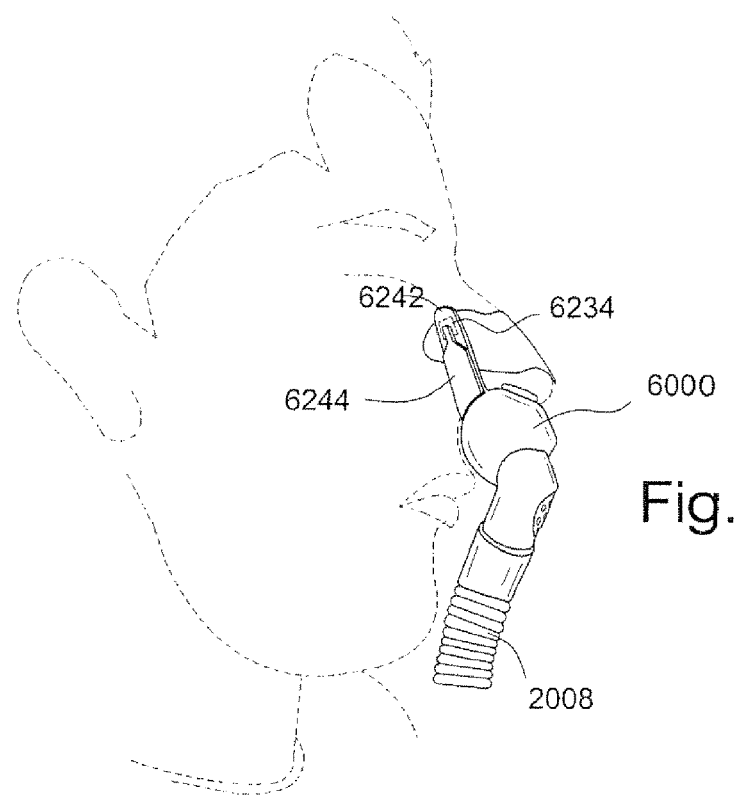
FIGS. 142 and 143 schematically depict a patient interface system according to another sample embodiment.
Figure 143:
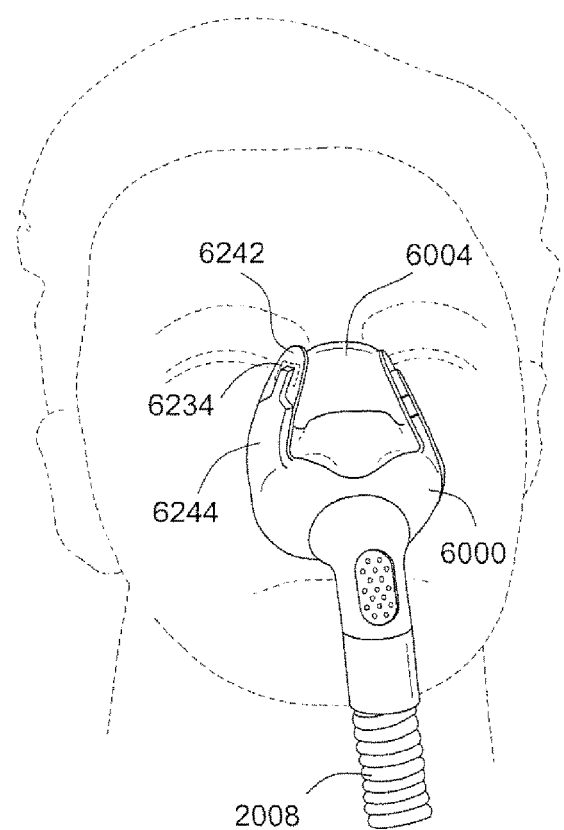

As shown in FIGS. 142 and 143, according to another sample embodiment, the connector 6242 of the patient interface structure 6000 include a thickened portion 6244 that narrows at a position corresponding to the hook fasteners 6234. This arrangement may provide a secure feeling to the patient, while retaining comfort.

2.1.15 Adhesive and Hook and Loop Fastening Material Fifteenth Embodiment

Figure 144:
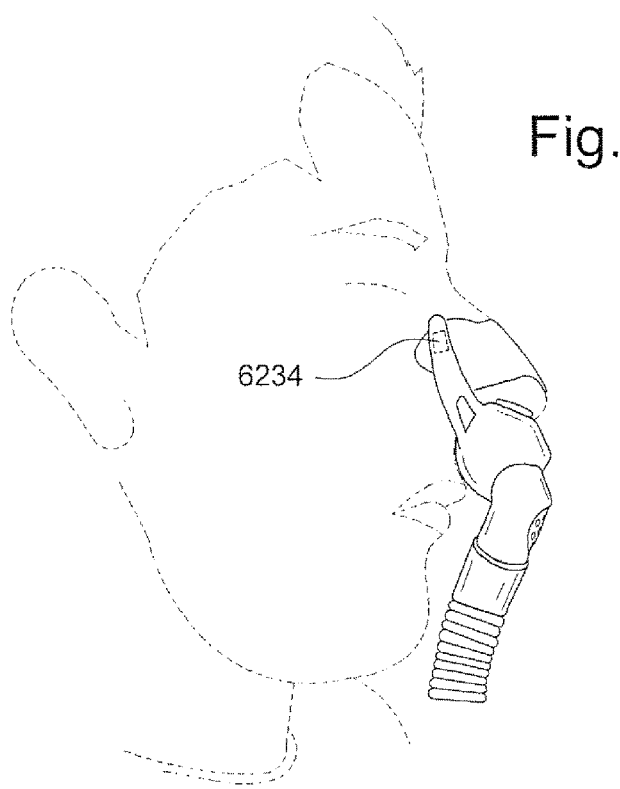
FIGS. 144-146 schematically depict a patient interface system according to another sample embodiment.
Figure 146:
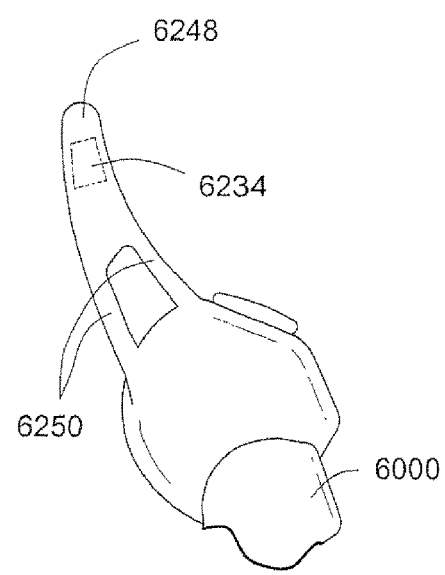
Figure 145:
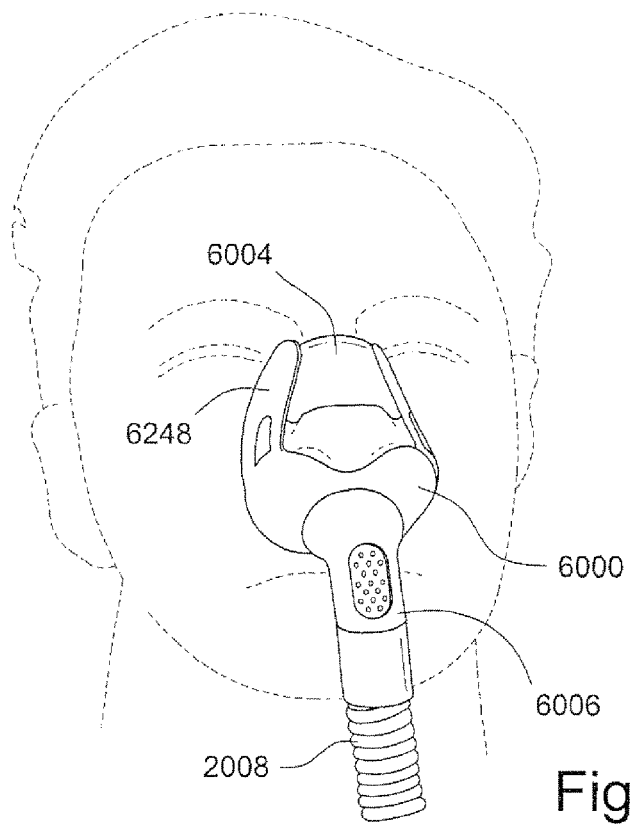

Referring to FIGS. 144-146, the connectors 6248 of the patient interface structure 6000 include legs 6250. The length of the legs 6250 may be adjusted for individual patients to provide the most secure and comfortable fit.

2.1.16 Adhesive and Hook and Loop Fastening Material Sixteenth Embodiment

Figure 147:
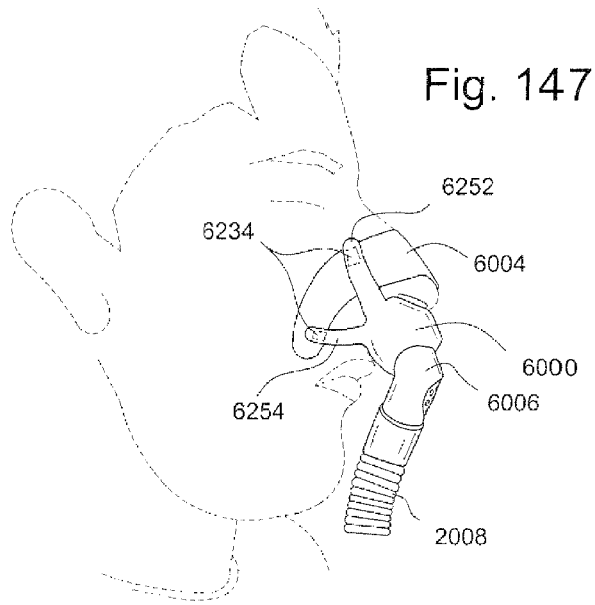
FIGS. 147 and 148 schematically depict a patient interface system according to another sample embodiment.
Figure 148:
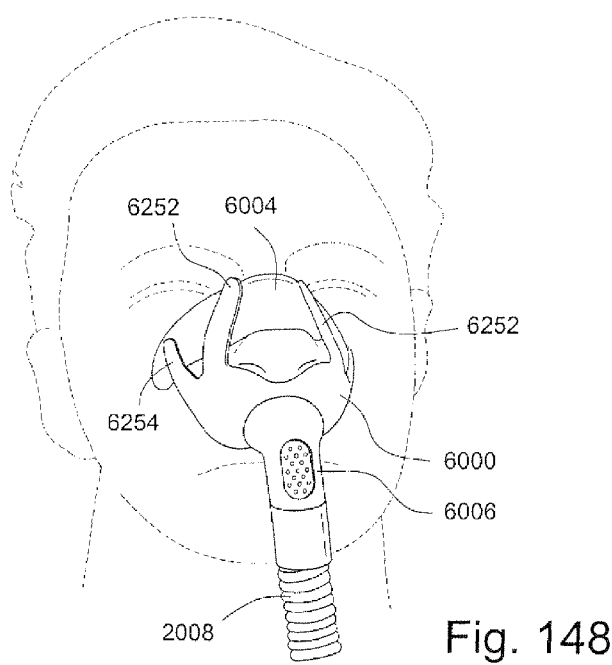

As shown in FIGS. 147 and 148, the adhesive strip 6004 including the loop fasteners may be provided to extend from the bridge of the patient's nose to the upper lip region. The patient interface structure 6000 may include connectors 6252, 6254 that include hook fasteners 6234 that engage the loop fasteners of the adhesive strip 6004. The connection of the hook fasteners 6234 to the loop fasteners of the adhesive strip 6004 provide forces that seal and stabilize the patient interface structure 6000 in engagement with the patient's nose.

2.2.1 Positioning and Stabilizing Using Adhesive and Providing Nasal Dilation First Embodiment Referring to FIGS. 65*a* and 65*b*, the patient interface structure 2000 may comprise a spring 2174 that is configured to engage the nares of the patient's nose. The spring 2174 may be attached at opposite ends to adhesive strips 2172. The spring 2174 is configured to bias the bottom of the nasal prongs or pillows 2002 to a dilated position. The adhesive strips 2174 are configured to be attached to the sides of the patient's nose to secure the patient interface structure 2000 in sealing engagement with the patient's nares.

Figure 66:
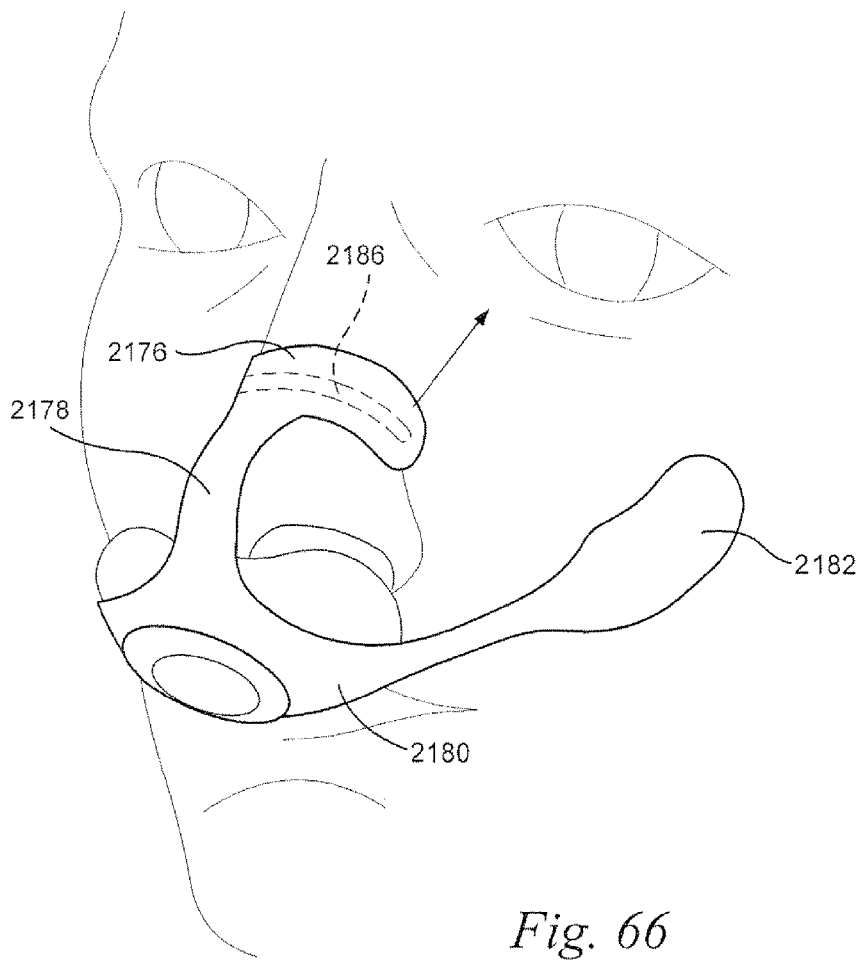
FIGS. 66 and 67 schematically illustrate an interface system according to another sample embodiment.

2.2.2 Positioning and Stabilizing Using Adhesive an Providing Nasal Dilation Second Embodiment Referring to FIG. 66, the patient interface system may comprise a lateral nasal bridge adhesive strip 2176 configured to extend across the bridge of the patient's nose. The lateral strip 2176 may also be configured to dilate the nasal passages, e.g., as done by Breathe Right Strips™. The lateral strip 2176 may be integrated with a longitudinal nasal bridge adhesive strip 2178 which is incorporated with a looped adhesive strip 2180 that is configured to adhesively engage the cushion and lateral adhesive strips 2182 that are configured to adhesively engage the sides of the patient's face, e.g. the cheeks.

2.3 Positioning and Stabilizing Nasal Cradle and Adhesive

Figure 60A:
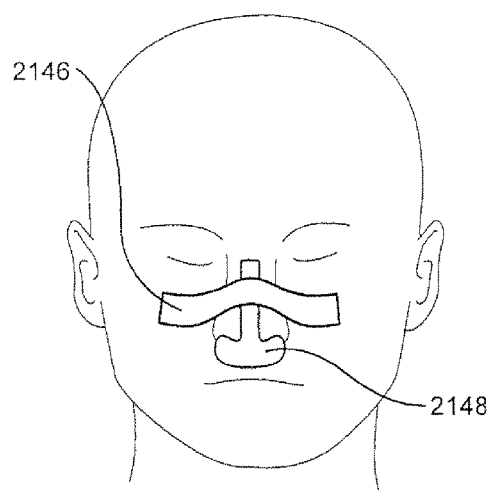
FIGS. 60a and 60b schematically illustrate a nasal cradle and adhesive for positioning an interface system according to a sample embodiment.
Figure 60B:
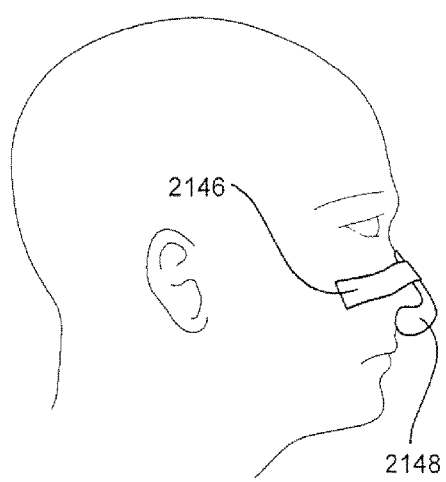

Referring to FIGS. 60*a* and 60*b*, a semi-rigid or rigid cradle 2148 may extend along the bridge of the patient's nose and form a cup under, or at, the nares of the patient. A cradle 2148 is configured to position the interface system at the nares of the patient. An adhesive strip 2146 may be provided to secure the cradle 2148 on the bridge of the patient's nose. The adhesive strip 2146 may extend, for example, to the cheeks of the patient for additional adhesion strength.

Figure 61:
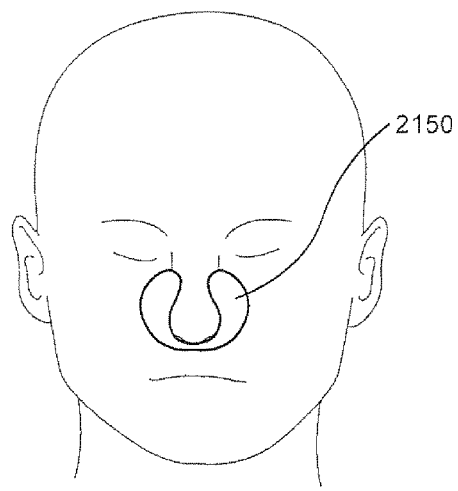
FIG. 61 schematically illustrates an adhesive strip for positioning an interface system according to another sample embodiment.
Figure 62:
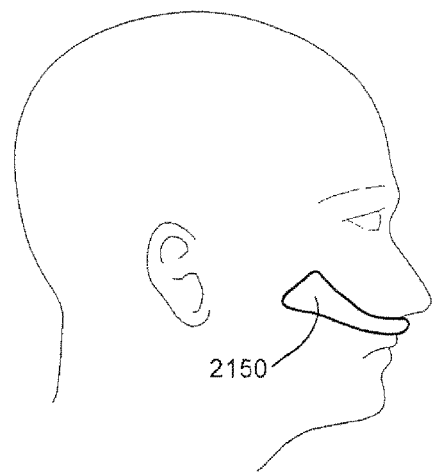
FIG. 62 schematically illustrates an adhesive strip for positioning an interface system according to another sample embodiment.

2.4 Positioning and Stabilizing Adhesive Strips with Multiple Contact Points Referring to FIGS. 61 and 62, an adhesive strip 2150 may be secured to the patient interface system and connect to the face of the patient at two points. As shown in FIG. 61, the adhesive strip 2150 may connect to the sides of the patient's nares and/or nasal bridge. As shown in FIG. 62, the adhesive strip 2150 may connect to the face of the patient at the cheeks.

Figure 63A:
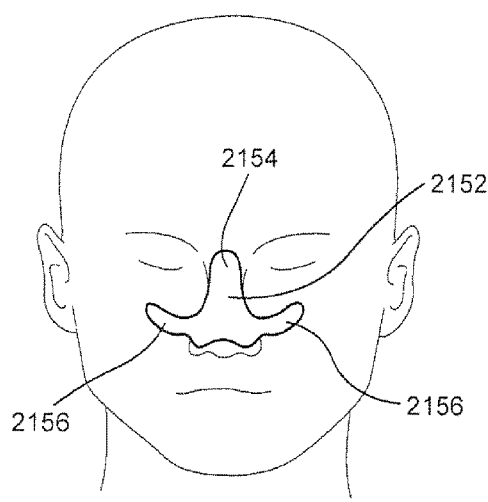
FIGS. 63a and 63b schematically illustrate an adhesive strip for positioning an interface system according to another sample embodiment.
Figure 63B:
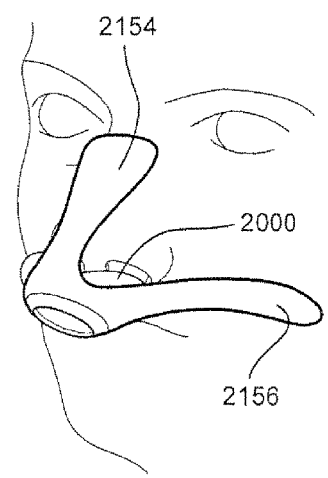

As shown in FIGS. 63*a* and 63*b*, the adhesive strip 2152 may secure the patient interface system, for example the patient interface structure 2000, to the patient's face at three points. The adhesive strip 2152 may include a nasal bridge strip 2154 configured to extend along the patient's nasal bridge and may comprise lateral strips 2156 configured to extend across the bridge of the patient's nose as shown in FIG. 63*a*, or along the cheeks of the patient as shown in FIG. 63*b*.

An adhesive strip 2158 may be provided to connect to the patient's face at four points, as shown in FIG. 64. The adhesive strip 2158 may comprise nasal bridge strips 2160 configured to engage the sides of the patient's nose and lateral strips 2162 configured to engage the cheeks of the patient.

It should also be appreciated that the connection between the strip(s) on the patient interface structure and the strip(s) on the patient may be formed by other methods, including, for example, friction or electrostatic connection.

3.0 Positioning and Stabilizing Using Additional Arrangements

3.1.1 Positioning and Stabilizing Additional Arrangement First Embodiment

Figure 54:
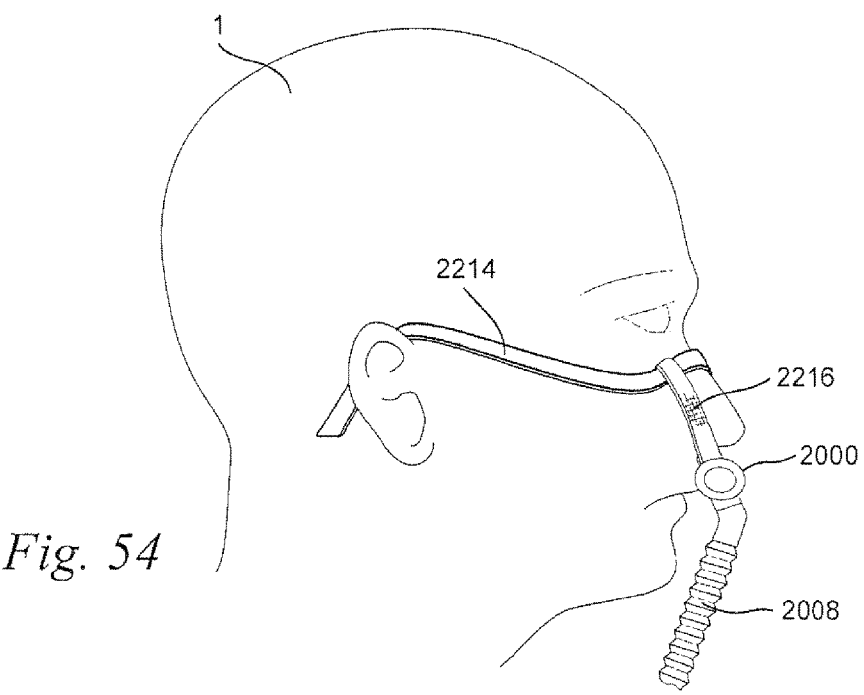
FIG. 54 schematically illustrates an interface system according to another sample embodiment.

Referring to FIG. 54, a patient interface structure 2000 is connected to a tube 2008 for delivery of a flow of breathable gas. The patient interface structure 2000 is connected to a rigid glasses type frame 2214 by connectors 2216 on opposite sides of the patient's nose (only one connector shown in FIG. 54). The rigid glasses type frame 2214 acts as a head strap in maintaining the patient interface structure 2000 in engagement with the nose of the patient.

3.1.2 Positioning and Stabilizing Additional Arrangement Second Embodiment

Figure 55:
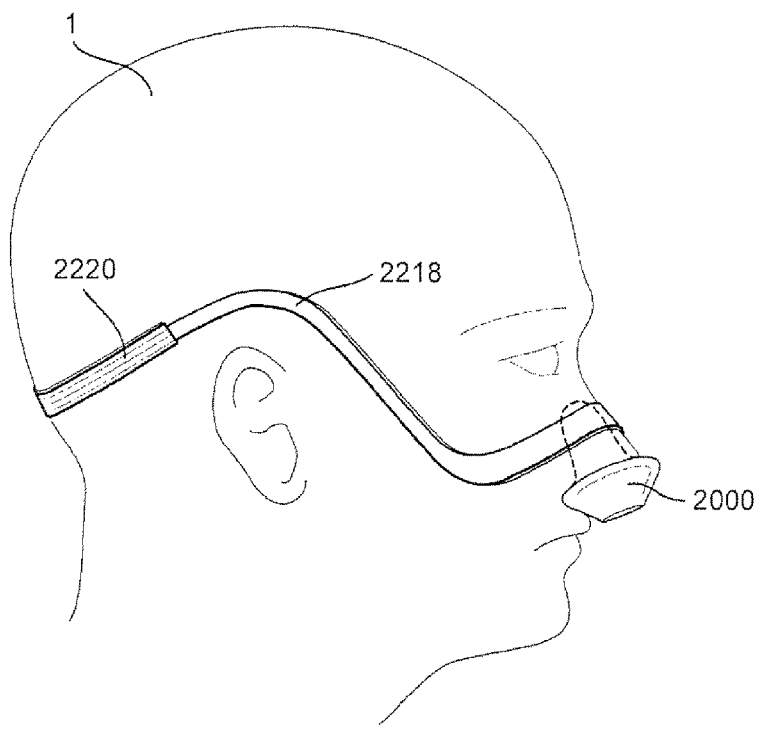
FIG. 55 schematically illustrates an interface system according to another sample embodiment.

As shown in FIG. 55, a patient interface structure 2000 is held in engagement with the nose of the patient by a rigid, or semi-rigid, first head strap portion 2218 that is connected to a flexible second head strap 2220 that allows for adjustment of the first head strap 2218.

3.1.3 Positioning and Stabilizing Additional Arrangement Third Embodiment

Figure 56:
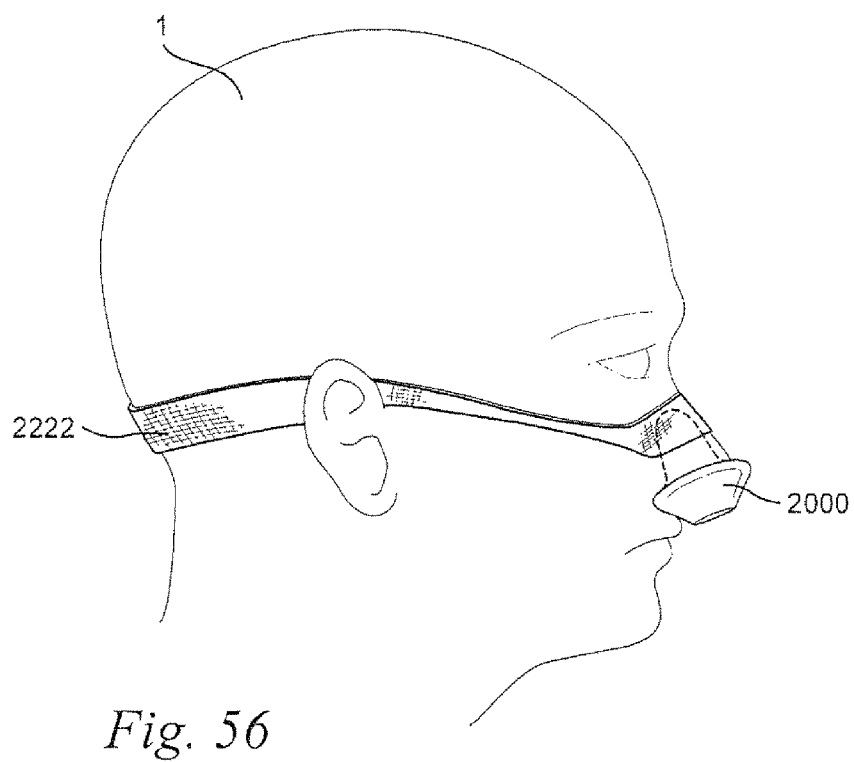
FIG. 56 schematically illustrates an interface system according to another sample embodiment.

As shown in FIG. 56, the patient interface structure 2000 may be held in engagement with a nose of the patient by a flexible head strap 2222 that passes over the ears of the patient.

3.1.4 Positioning and Stabilizing Additional Arrangement Fourth Embodiment

Figure 58:
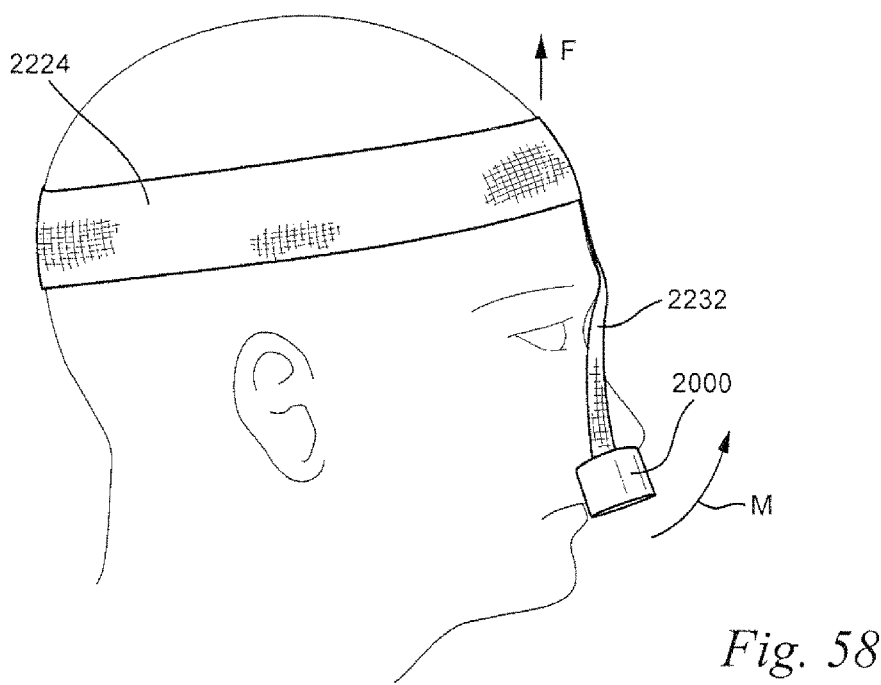
FIG. 58 schematically illustrates an interface system according to another sample embodiment.

Referring to FIG. 58, the patient interface system may include a head strap 2224 that is connected to a vertical connector 2232 that is connected to the patient interface structure 2000 to maintain the patient interface structure 2000 in engagement with the nose of the patient. The vertical connector 2232 may be connected between the head strap 2224 and the patient interface structure 2000 to provide a force F that produces a moment M that acts to maintain the patient interface structure 2000 in engagement with the nose of the patient.

3.2 Positioning and Stabilizing—Headgear

3.2.1 Positioning and Stabilizing—Headgear First Embodiment

Figure 88:
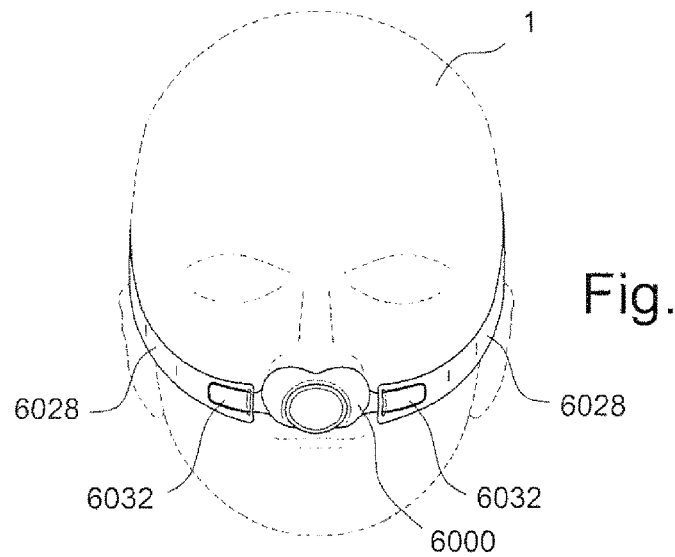
FIGS. 88-90 schematically illustrate a patient interface system according to another sample embodiment.
Figure 89:
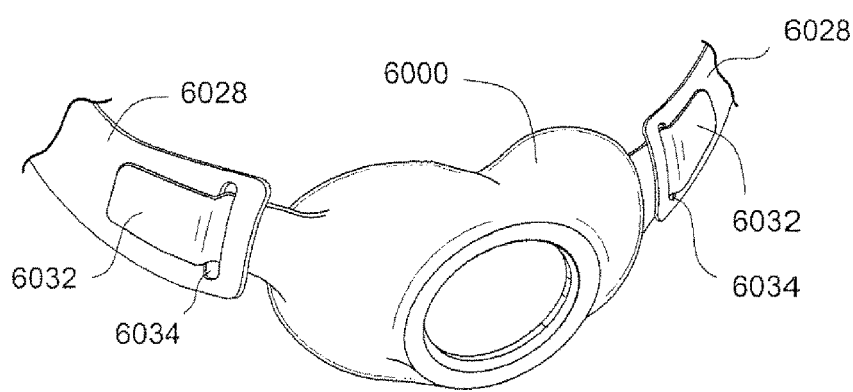
Figure 90:
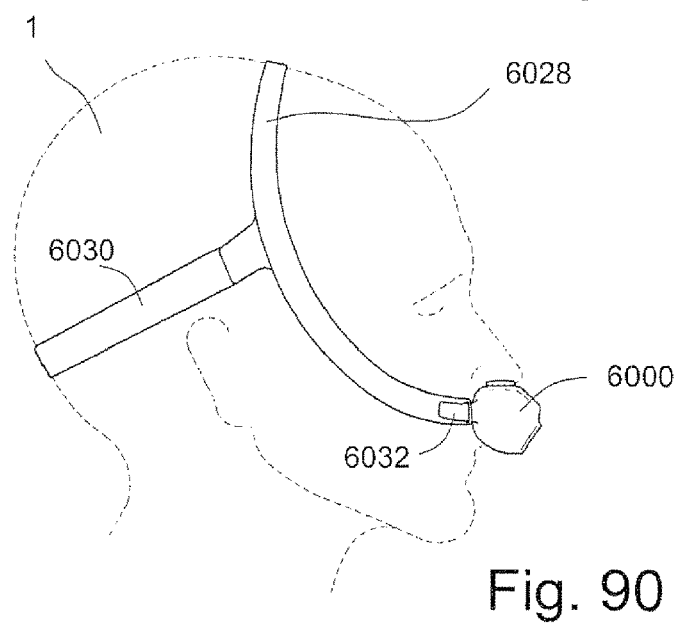

Referring to FIGS. 88-90, a patient interface system comprises a patient interface structure 6000 having connectors 6032 on opposite sides. The connectors 6032 may comprise hook fasteners that are, for example, molded in place. The connectors 6032 are connected to a strap 6028 that is configured to extend around the face of the patient past the patient's cheeks and extending over and around the forehead of the patient. The straps 6028 may comprise loop fasteners that engage the hook fasteners on the connectors 6032. The straps 6028 may further comprise apertures (or slots) 6034 through which the straps 6028 may be inserted. A back strap 6030 may be provided to extend around the back of the patient's head to assist in maintaining the straps 6028 in engagement with the patient's face.

3.2.2 Positioning and Stabilizing—Headgear Second Embodiment

Figures 91, 92:
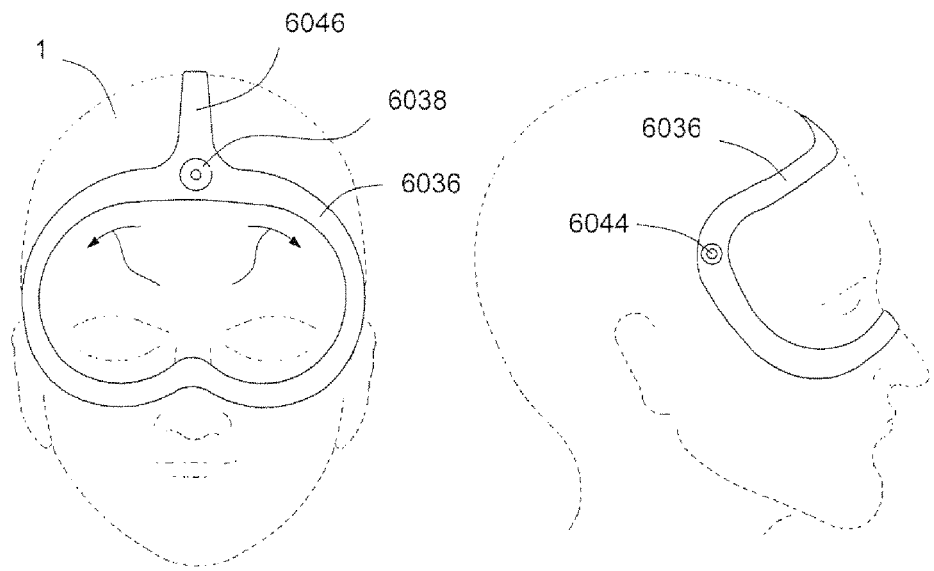
FIGS. 91 and 92 schematically illustrate a patient interface positioning and stabilizing structure according to a sample embodiment.

As shown in FIGS. 91 and 92, a patient interface system according to another sample embodiment includes a patient interface positioning and stabilizing structure 6036 that is configured to engage the face of the patient. The positioning and stabilizing structure 6036 may take the form of a band that extends around the forehead of the patient, the eyes of the patient and over the bridge of the patient's nose. The positioning and stabilizing structure 6036 may be formed of, for example, TPE. The positioning and stabilizing structure 6036 may include a backwardly extending portion 6046 that engages the top of the patient's head and provides spring forces to the positioning and stabilizing structure 6036 to assist in retaining the positioning and stabilizing structure 6036 in engagement with the face of the patient.

The positioning and stabilizing structure 6036 may also include a connector 6038 that is configured to be connected to a vertical connector, such as for example the one shown in FIG. 58, to maintain a patient interface structure in sealing engagement with the nose of the patient. The connectors 6038 may comprise, for example, adhesive or a hook or loop fastener material that is configured to connect to the vertical connector.

As shown in FIG. 92, the positioning and stabilizing structure 6036 may comprise an adhesive tab 6044 to assist in maintaining the positioning and stabilizing structure 6036 in engagement with the face of the patient.

3.2.3 Positioning and Stabilizing—Headgear Third Embodiment

Figures 93, 94:
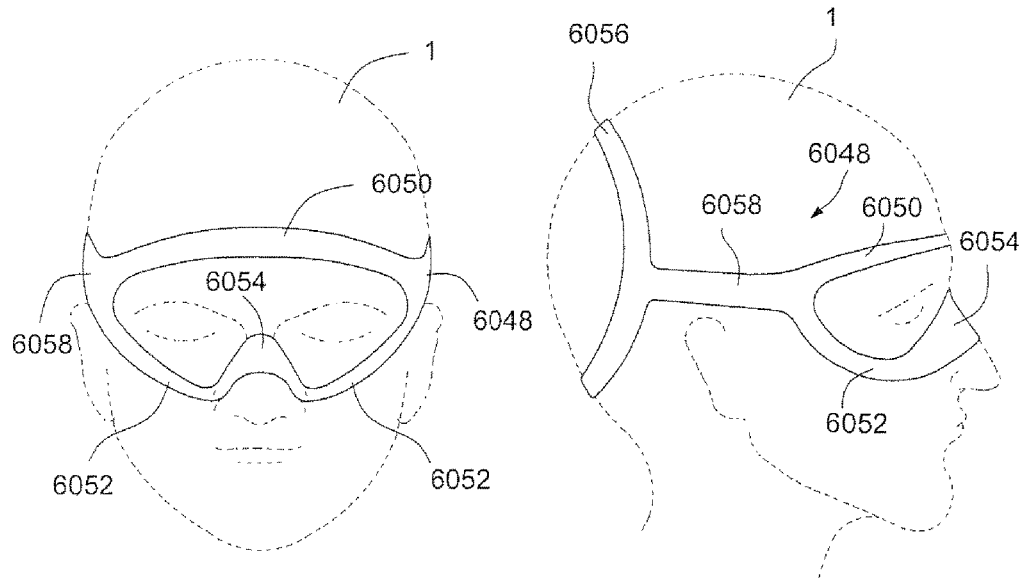
FIGS. 93 and 94 schematically illustrate a patient interface positioning and stabilizing structure according to another sample embodiment.

Referring to FIGS. 93 and 94, a patient interface positioning and stabilizing structure 6048 includes a strap 6050 extending generally across the forehead of the patient and side straps 6052 generally extending along the cheeks of the patient and connected to a nasal bridge strap 6054 extending across the bridge of the patient's nose. Side straps 6058 extend along the sides of the patient's head and connect to a back strap 6056 that is configured to engage the back of the patient's head, for example, by circling the back of the patient's head. The nasal bridge strap 6054 may include loop fasteners that engage hook fasteners provided on connectors that are connected to the patient interface structure to maintain the patient interface structure in sealing engagement with the nose of the patient.

3.2.4 Positioning and Stabilizing—Headgear Fourth Embodiment

Figures 95, 96:
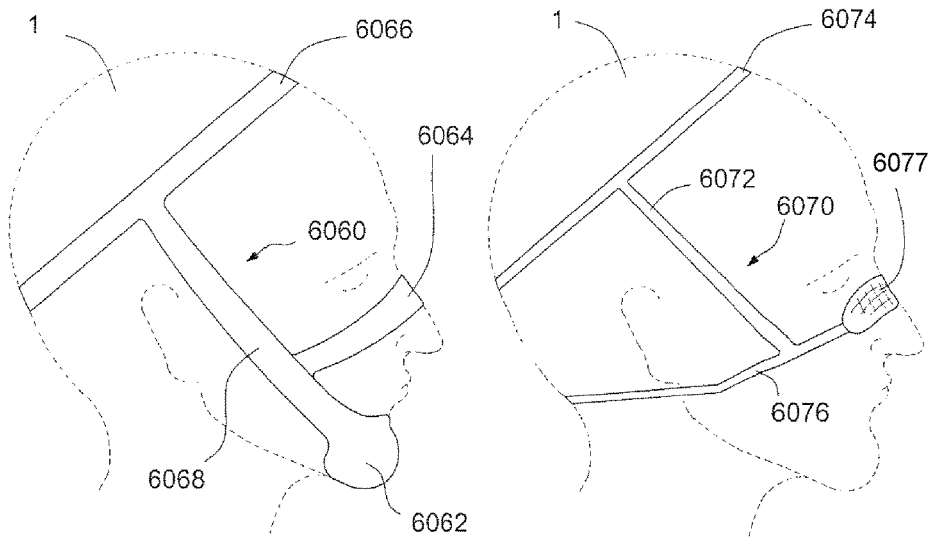
FIG. 95 schematically illustrates a patient interface positioning and stabilizing structure according to another sample embodiment.
FIG. 96 schematically illustrates a patient interface positioning and stabilizing structure according to another sample embodiment.

A patient interface positioning and stabilizing structure 6060 according to another sample embodiment is shown in FIG. 95 and comprises a crown strap 6066 that is configured to engage the crown of the patient's head. Side straps 6068 extend from the crown strap 6066 and are connected to a chin strap 6062. A nasal bridge strap 6064 is connected between the side strap 6068 and is configured to engage the bridge of the patient's nose. The nasal bridge strap 6064 may include, for example, loop fastener material configured to connect to hook fastener material provided on connectors of a patient interface structure. It should be appreciated that the nasal bridge strap 6064 may be formed as a rigid member.

3.2.5 Positioning and Stabilizing—Headgear Fifth Embodiment

Referring to FIG. 96, a patient interface positioning and stabilizing structure 6070 may include a crown strap 6074 and side straps 6072. Lower straps 6076 may extend around the patient's head under the patient's ears and be connected to a strip 6077 of loop fastener material that may include adhesive to adhere the strip 6077 to the nose of the patient 1.

3.2.6 Positioning and Stabilizing—Headgear Sixth Embodiment

Figures 97, 98:
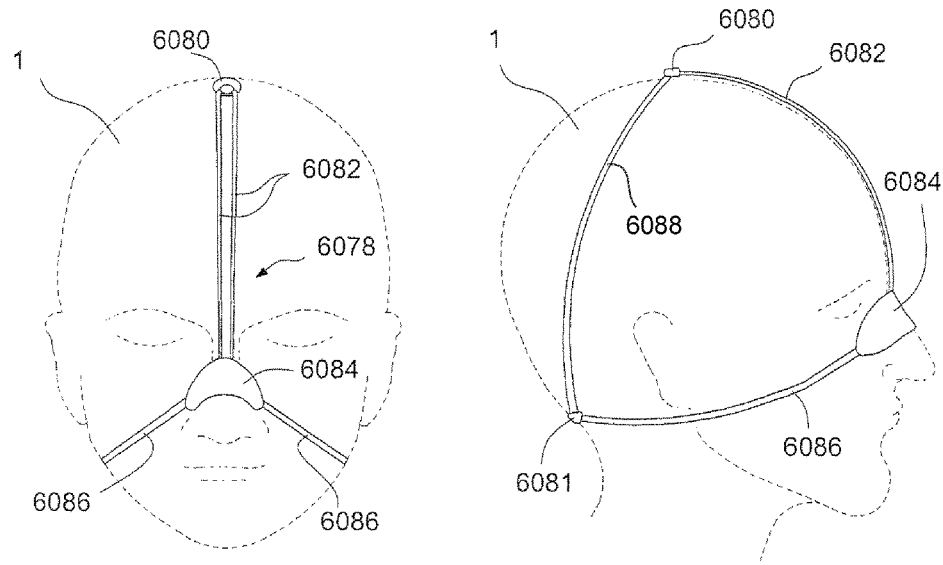
FIGS. 97 and 98 schematically illustrate a patient interface and stabilizing structure according to another sample embodiment.

As shown in FIGS. 97 and 98, a patient interface positioning and stabilizing structure 6078 according to another sample embodiment includes vertical straps 6082 that extend from a connector 6080 that is connected to back straps 6088. Side straps 6086 are connected to a strip of loop fastener material 6084 which is also connected to the vertical strap 6082. The side straps 6086 and the back straps 6088 are connected by connectors 6081 at the back of the patient's head.

3.2.7 Positioning and Stabilizing—Headgear Seventh Embodiment

Figure 99:
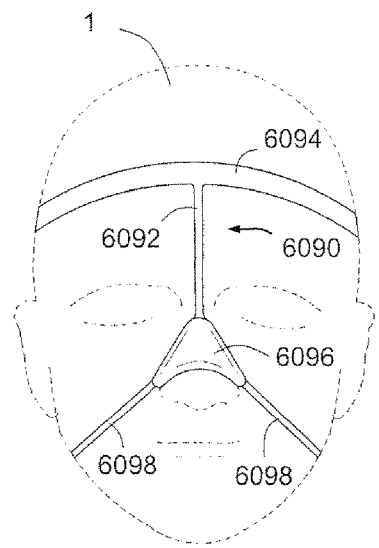
FIGS. 99 and 100 schematically illustrate a patient interface positioning and stabilizing structure according to another sample embodiment.
Figure 100:
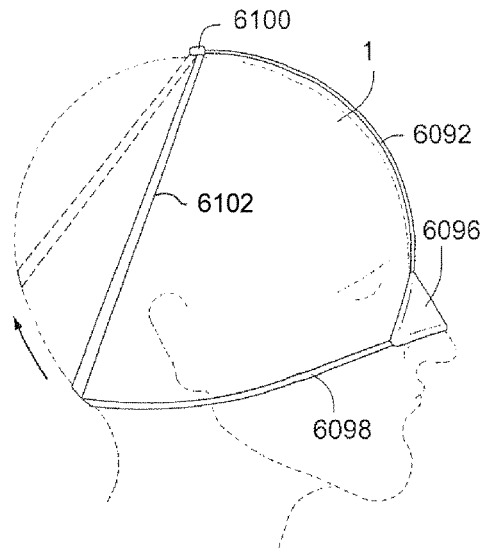

Referring to FIGS. 99 and 100, a patient interface positioning and stabilizing structure 6090 according to another sample embodiment includes a vertical strap 6092 that extends from a crown strap 6094. The vertical strap 6092 is connected to a strip of loop fastener material 6096 that is configured to engage hook fastener material provided on connectors of a patient interface structure that sealingly engages the nose of the patient. The strip 6096 may comprise adhesive to adhere the strip to the patient's nose. Side straps 6098 are also connected to the strip 6096 and extend around the sides of the patient's face beneath the patient's ears as shown in FIG. 100. Back straps 6102 are connected to the side straps 6098 and to the crown strap 6094 at a connector 6100. As shown in FIG. 100, the position of the back straps 6102 may be adjusted, as shown by the arrow, to accommodate patients having different head sizes, or to adjust the fit of a particular patient according to the comfort of the patient.

3.2.8 Positioning and Stabilizing—Headgear Eighth Embodiment

Figure 101:
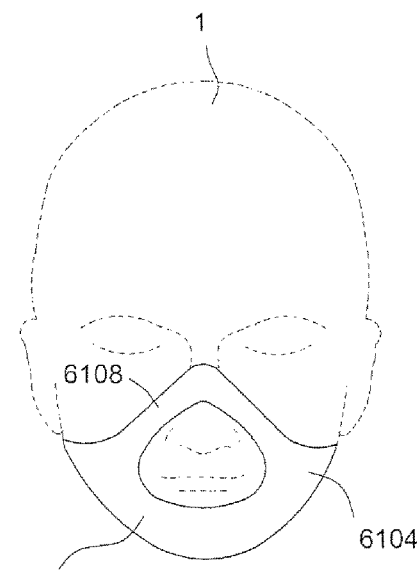
FIGS. 101 and 102 schematically illustrate a patient interface positioning and stabilizing structure according to another sample embodiment.
Figure 102:
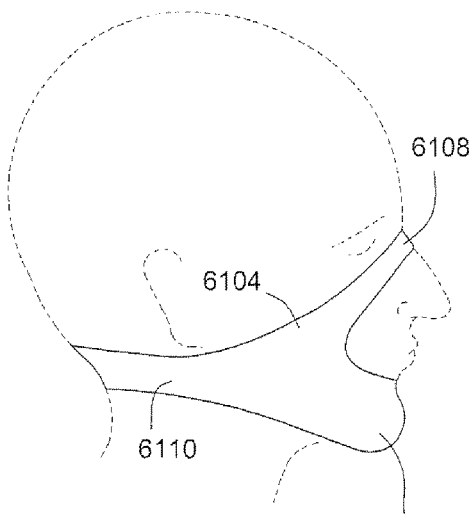

As shown in FIGS. 101 and 102, a patient interface positioning and stabilizing structure 6104 according to another embodiment comprises a nasal bridge strap 6108 that extends across the bridge of the patient's nose. The nasal bridge strap 6108 is connected to a chin strap 6106 that engages the chin of the patient. A back strap 6110 is connected to the nasal bridge strap 6108 and the chin strap 6106 and extends around the back of the patient's head to secure the patient interface positioning and stabilizing structure 6104 on the face of the patient.

3.2.9 Positioning and Stabilizing—Headgear Ninth Embodiment

Figure 103:
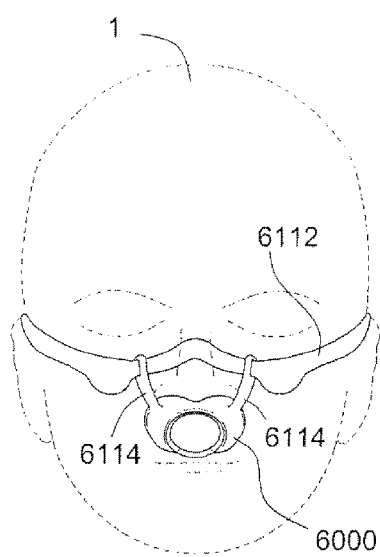
FIGS. 103 and 104 schematically illustrate a patient interface system according to another sample embodiment.
Figure 104:
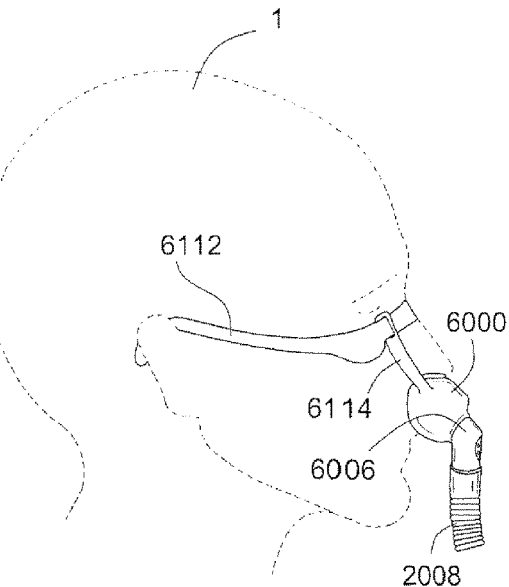

As shown in FIGS. 103 and 104, a patient interface positioning and stabilizing structure comprises rigid member 6112 that extends across the face of the patient and engages the ears of the patient. The patient interface structure 6000 includes connectors 6114 that engage the rigid member 6112 to position and stabilize the patient interface structure 6000 in sealing engagement with the nose of the patient. The connectors 6114 may adjustably engage the rigid member 6112 to allow the fit of the patient interface structure 6000 with the nose of the patient to be adjusted.

3.2.10 Positioning and Stabilizing—Headgear Tenth Embodiment

Figure 105:
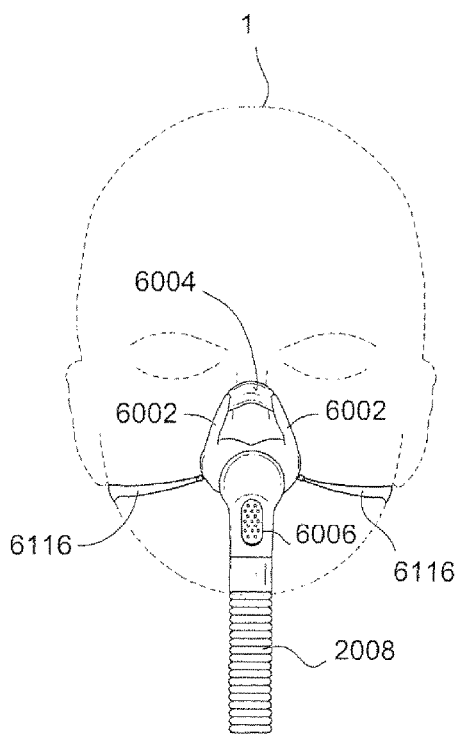
FIGS. 105 and 106 schematically illustrate a patient interface system according to another sample embodiment.
Figure 106:
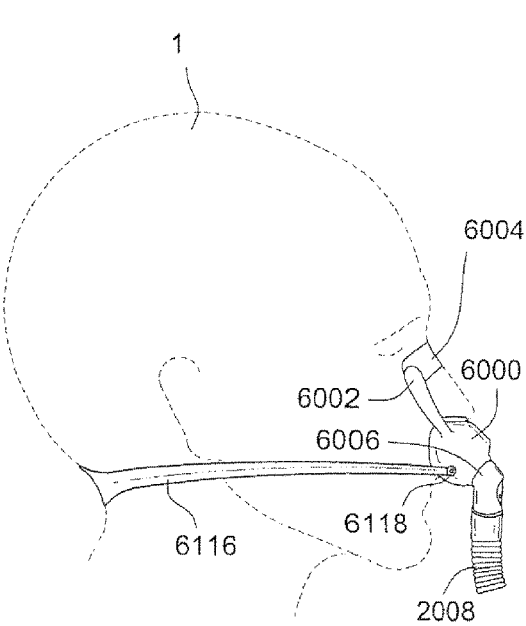

Referring to FIGS. 105 and 106, the patient interface structure 6000 includes connectors 6002 that include, for example, hook fasteners. The connectors 6002 engage an adhesive strip 6004 that extends across the bridge of the patient's nose and includes loop fasteners that engage the hook fasteners of the connector 6002. A strap 6116 may be connected to the patient interface structure 6000 by connector 6118 and extend around the back of the patient's head to assist in maintaining the patient interface structure 6000 in engagement with the nose of the patient. The strap 6116 may be, for example, a high stretch tape.

3.2.11 Positioning and Stabilizing—Headgear Eleventh Embodiment

Figure 107:
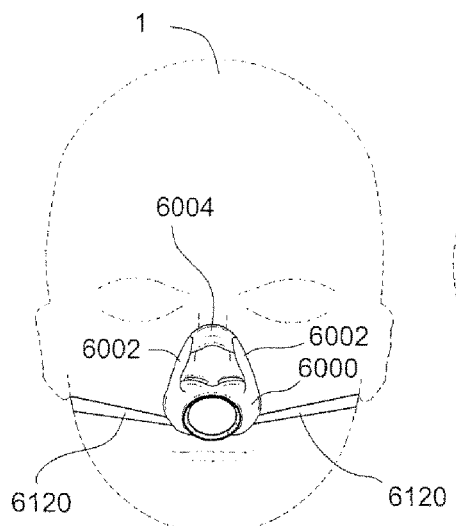
FIGS. 107 and 108 schematically illustrate a patient interface system according to another sample embodiment.
Figure 108:
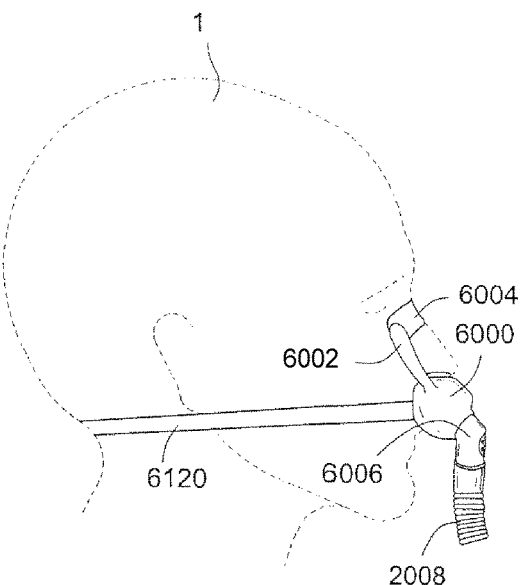

As shown in FIGS. 107 and 108, the sealing engagement of the patient interface structure 6000 with the nose of the patient may be assisted by a strap 6120 that is connected to the patient interface structure 6000 and extends around the patient's head, for example, under the ears of the patient. The straps 6120 may be an elastic strap.

3.2.12 Positioning and Stabilizing—Headgear Twelfth Embodiment

Figure 109:
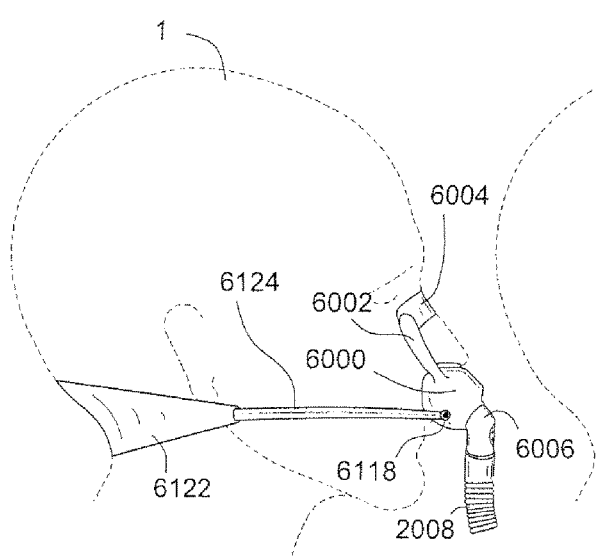
FIGS. 109 and 110 schematically illustrate a patient interface system according to another sample embodiment.

Another sample embodiment is shown in FIG. 109 which depicts the patient interface structure 6000 connected to straps 6124 by connectors 6118. The straps 6124 may be connected to a strap 6122 that extends around the back of the patient's head. The straps 6124 may be formed of, for example, elastic, TPE, or silicone. The strap 6122 may be, for example, a soft textile strap.

3.2.13 Positioning and Stabilizing—Headgear Thirteenth Embodiment

Figure 110:
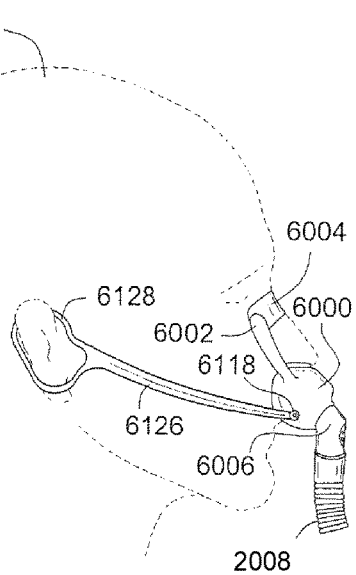

As shown in FIG. 110, the sealing engagement of the patient interface structure 6000 with the nose of the patient may be assisted by straps 6126 that are connected to the patient interface structure 6000 by connectors 6118. The straps 6126 may include ear loops 6128 that are configured to loop around the ears of the patient to maintain the straps 6126 in engagement with the face of the patient to permit the straps 6126 to assist in maintaining the patient interface structure 6000 in sealing engagement with the patient's nose.

3.3 Positioning and Stabilizing—Headgear Tabs

3.3.1 Positioning and Stabilizing—Headgear Tabs First Embodiment

Figures 115, 116, 117:
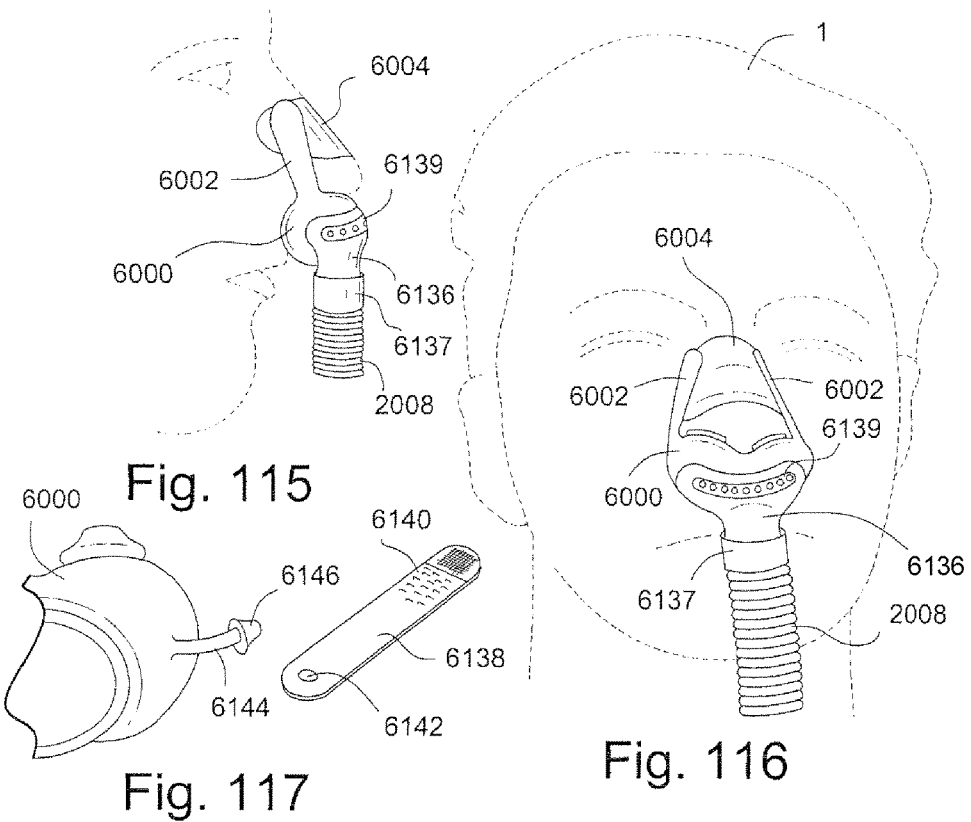
FIGS. 115 and 116 schematically illustrate a patient interface system according to another sample embodiment.
FIG. 117 schematically illustrates a patient interface structure and connector according to a sample embodiment.
Figures 118, 119:
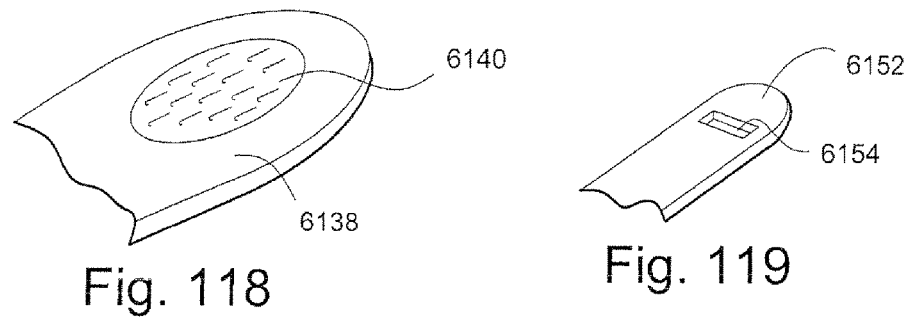
FIG. 118 schematically illustrates a patient interface structure connector according to a sample embodiment.
FIGS. 119-121 schematically illustrate a patient interface structure connector according to another sample embodiment.

Referring to FIG. 117, a connector 6138 configured to connect the patient interface structure 6000 to a strip 6138 that may be adhered to the nose of the patient and that includes hook fasteners 6140. The hook fasteners 6140 are configured to engage loop fasteners on a strip adhered to the nose of the patient. The connector 6138 includes an aperture 6142 that is configured to receive a tab 6144 of the patient interface structure 6000. The tab 6144 includes an enlarged end 6146 that passes through the aperture 6142 and acts to prevent removal of the connector 6138 once the enlarged end 6146 is passed through the aperture 6142. The connector 6138 and the tab 6144 may be formed of flexible material to allow the connector 6138 to be removed from the tab past the enlarged end 6146. The connector 6138 may be formed by, for example, die cutting to reduce the expense of forming the connector 6138. The connectors 6138 may thus be disposable and replaced, for example on a weekly basis. Referring to FIG. 118, the hook fastener 6140 may be glued to the connector 6138.

3.3.2 Positioning and Stabilizing—Headgear Tabs Second Embodiment

Figures 120, 121:
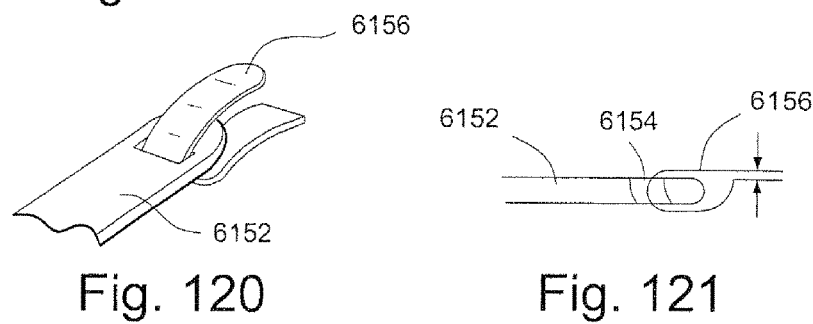

Referring to FIGS. 119-121, the connectors 6152 may include a slot 6154. A strap 6156 which may comprise hook fasteners is threaded through the slot 6154 and may be ultrasonically welded, as shown by the arrows in FIG. 121, to connect the strap to the connector 6152.

3.3.3 Positioning and Stabilizing—Headgear Tabs Third Embodiment

Figure 122:
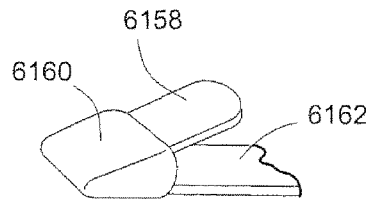
FIG. 122 schematically illustrates a patient interface structure connector according to another sample embodiment.

Referring to FIG. 122, the tab 6162 of the patient interface structure may be connected to a connector 6158 by a junction 6160.

3.3.4 Positioning and Stabilizing—Headgear Tabs Fourth Embodiment

Figure 123:
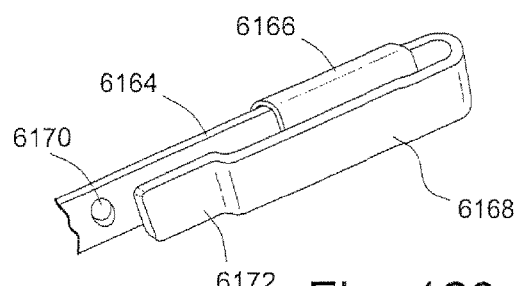
FIGS. 123 and 124 schematically illustrate a patient interface structure connector according to another sample embodiment.
Figure 124:
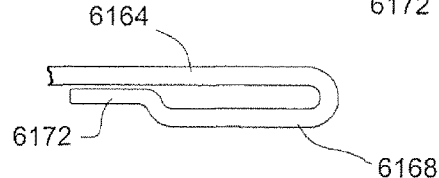

Referring to FIGS. 123 and 124, the tab 6164 includes a folded portion 6168 that folds over a strip 6166. An end portion 6172 of the tab 6164 is secured to the tab 6164. The tab 6164 also includes an aperture 6170 that is configured to connect the tab 6164 to the patient interface structure.

3.3.5 Positioning and Stabilizing—Headgear Tabs Fifth Embodiment

Figure 125:
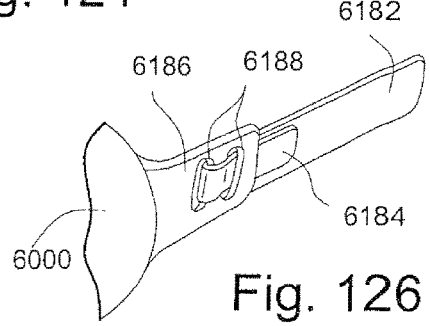
FIG. 125 schematically illustrates a patient interface structure and connector according to a sample embodiment.

As shown in FIG. 125, the patient interface structure 6000 includes a tab 6174 that includes a slot 6180. A connector 6176, that may include hook fasteners, includes an end portion 6178 that is passed through the slot 6180 and folded back on to the connector 6176 and attached thereto.

3.3.6 Positioning and Stabilizing—Headgear Tabs Sixth Embodiment

Figure 126:
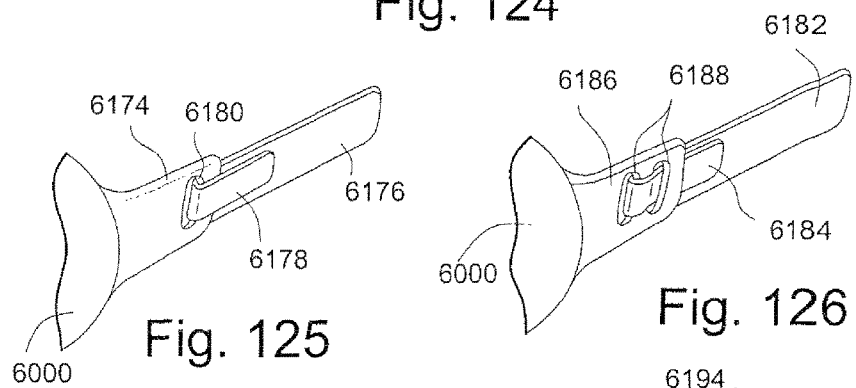
FIG. 126 schematically illustrates a patient interface structure and connector according to another sample embodiment.

Referring to FIG. 126, according to a variation, the tab 6186 comprises two slots 6188 and an end portion 6184 of a connector 6182 is threaded through the two slots 6188 to secure the end portion 6184 to the connector 6182.

3.3.7 Positioning and Stabilizing—Headgear Tabs Seventh Embodiment

Figure 127:
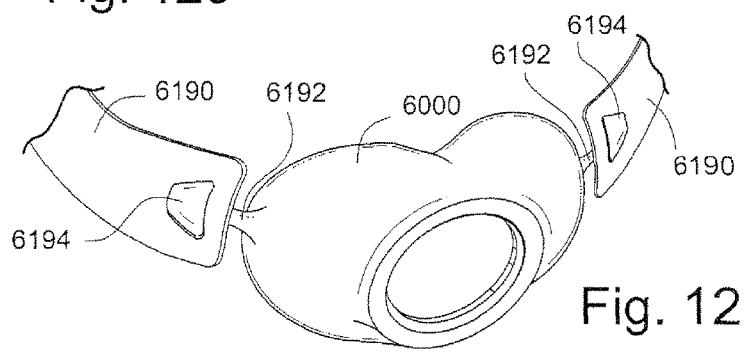
FIG. 127 schematically illustrates a patient interface structure and connector according to another sample embodiment.

Referring to FIG. 127, the patient interface structure 6000 includes tabs 6192 having enlarged end portions 6194. The enlarged end portions 6194 pass through apertures in connectors 6190 to secure the patient interface structure 6000 to the connector or patient interface positioning and stabilizing structure 6190.

3.3.8 Positioning and Stabilizing—Headgear Tabs Eighth Embodiment

Figure 128:
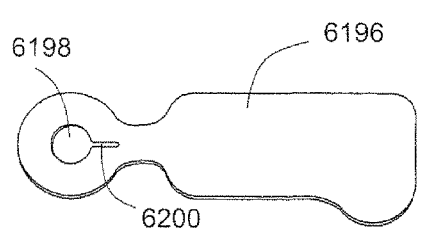
FIGS. 128 and 129 schematically illustrate a patient interface structure connector according to another sample embodiment.
Figure 129:
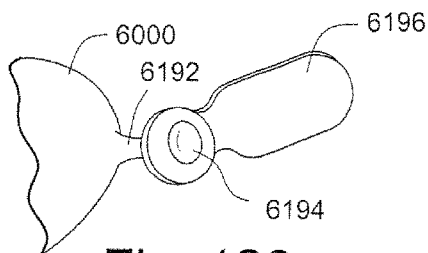

Referring to FIGS. 128 and 129, connectors 6196 may comprise apertures 6198 to engage tabs of a patient interface structure. The apertures 6198 include slots 6200 that assist in inserting the enlarged end portion 6194 of the tabs of the patient interface structure 6000 through the apertures 6198.

3.3.9 Positioning and Stabilizing—Headgear Tabs Ninth Embodiment

Figure 130:
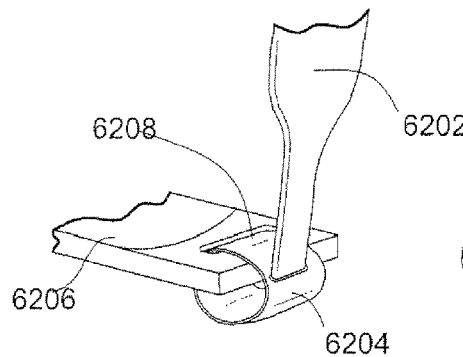
FIG. 130 schematically illustrates a patient interface structure connector according to another sample embodiment.

Referring to FIG. 130, the tab 6206 comprises a slot 6208. The connector 6202 is connected to a loop 6204 that is provided through the slot 6208.

3.3.10 Positioning and Stabilizing—Headgear Tabs Tenth Embodiment

Figure 131:
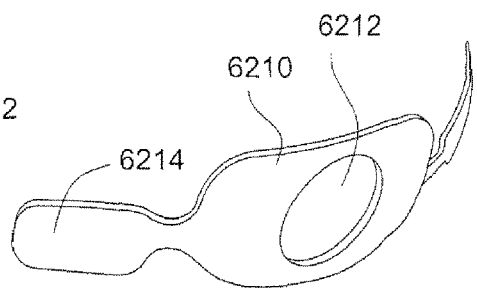
FIG. 131 schematically illustrates a patient interface structure connector according to another sample embodiment.
Figure 132:
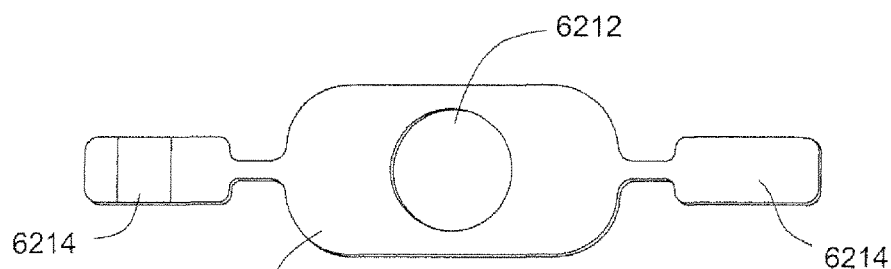
FIG. 132 schematically illustrates a patient interface structure connector according to another sample embodiment.

Referring to FIGS. 131 and 132, a tab 6210 is configured to support a patient interface structure. The tab 6210 comprises an aperture 6212 that corresponds to the aperture of the patient interface structure. The aperture 6212 is configured to receive an elbow or a sealing ring connected to a tube for delivery of the flow of breathable gas. The tab 6210 comprises connector portions 6214 that are configured to be connected to a patient interface positioning and stabilizing structure, for example an adhesive strip comprising fastener material such as loop fasteners, or to a headgear.

3.3.11 Positioning and Stabilizing—Headgear Tabs Eleventh Embodiment

Figure 133:
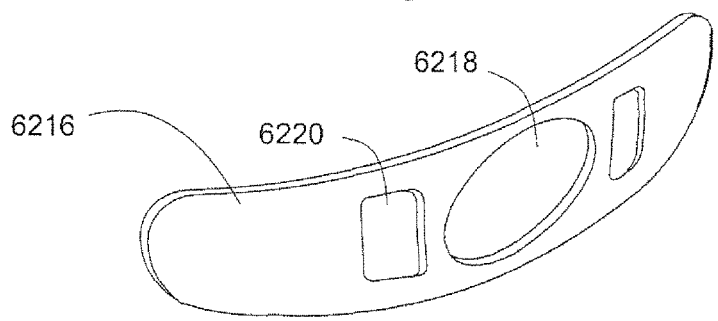
FIG. 133 schematically illustrates a patient interface structure connector according to another sample embodiment.

As shown in FIG. 133, the tab 6216 may comprise an aperture 6218 for receiving a sealing ring or an elbow connected to a tube to deliver a flow of breathable gas. Additional aperture 6220 may be provided for receiving the ends of connectors or a patient interface stabilizing and positioning structure having connectors insertable into the aperture 6220.

It should be appreciated that the tabs shown in FIGS. 131-133 may be formed by die cutting.

3.3.12 Positioning and Stabilizing—Headgear Tabs Twelfth Embodiment

Figure 134:
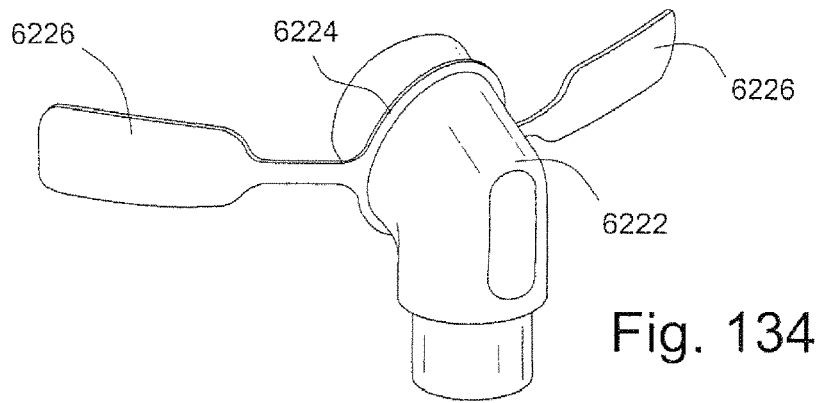
FIG. 134 schematically illustrates a patient interface structure connector according to another sample embodiment.

Referring to FIG. 134, a tab 6224 may be formed by molding the tab 6224 on an elbow 6222 that is configured to be connected to a tube for delivering a flow of breathable gas. The tab 6224 may comprise end portions 6226 that are configured to be connected to a patient interface positioning and stabilizing structure, such as an adhesive strip attached to the patient's nose that includes fastener material, or to a headgear.

3.4 Positioning and Stabilizing—Elbow and Swivel

3.4.1 Positioning and Stabilizing—Elbow and Swivel First Embodiment

Referring to FIGS. 111 and 112, a patient interface system according to another sample embodiment includes an elbow 6006 that includes an angled portion 6006a that is connected to the patient interface structure 6000. The angled portion 6006a of the elbow 6006 positions the tube 2008 so that it extends straight down from the face of the patient and avoids the patient's chin. As shown in FIGS. 111 and 112, the elbow 6006 is fixed with respect to the cushion 6000 and does not rotate. The elbow 6006 may include a diffuser vent 6011. The tube 2008 is connected to the elbow 6006 through a swivel 6130 that permits the tube 2008 to swivel 360° with respect to the elbow 6006.

3.4.2 Positioning and Stabilizing—Elbow and Swivel Second Embodiment

As shown in FIGS. 113 and 114, according to another sample embodiment, the tube 2008 may be connected to the patient interface structure 6000 by a gusset 6132. The gusset 6132 is expandable as shown by the arrow to reduce tube drag. A swivel 6134 may be provided between the gusset 6132 and the tube 2008 to allow the tube 2008 to swivel with respect to the patient interface structure 6000.

The patient interface structure 6000 may include a vent 6133 that is integrally formed with the patient interface structure 6000. It should be appreciated that the vent 6133 may be provided as a separate part that is attached to the patient interface structure 6000.

3.4.3 Positioning and Stabilizing—Elbow and Swivel Third Embodiment

Referring to FIGS. 115 and 116, the patient interface structure 6000 may be connected to the tube 2008 by an elbow 6136. The elbow 6136 is not round and is attached to the patient interface structure 6000. The elbow 6136 includes a vent 6139 that is easier to form than a vent formed in the patient interface structure 6000. A swivel 6137 may be provided between the elbow 6136 and the tube 2008. The swivel 6137 may be molded in a cuff of the tube 2008.

4.1 Patient Interface With Inflatable Pillows First Embodiment

Figure 71:
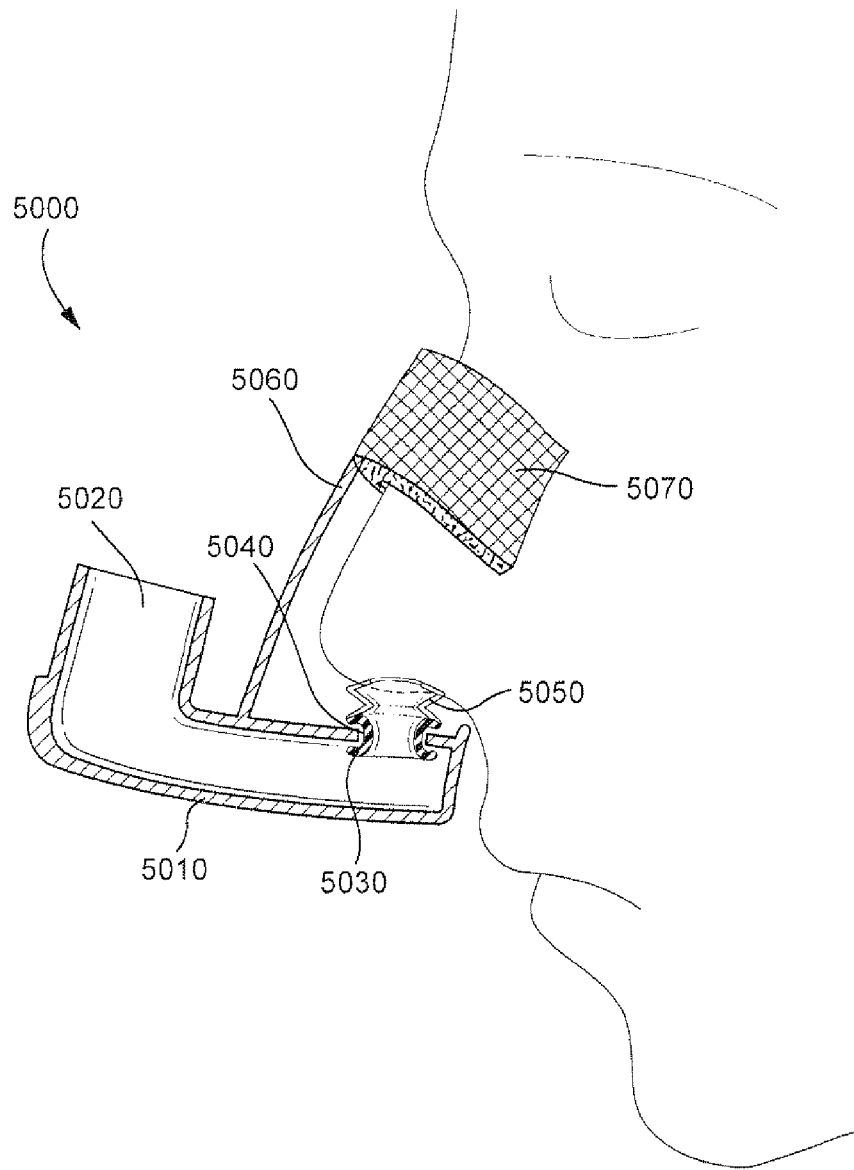
FIGS. 71 and 72 schematically illustrate a patient interface system according to another sample embodiment.
Figure 72:
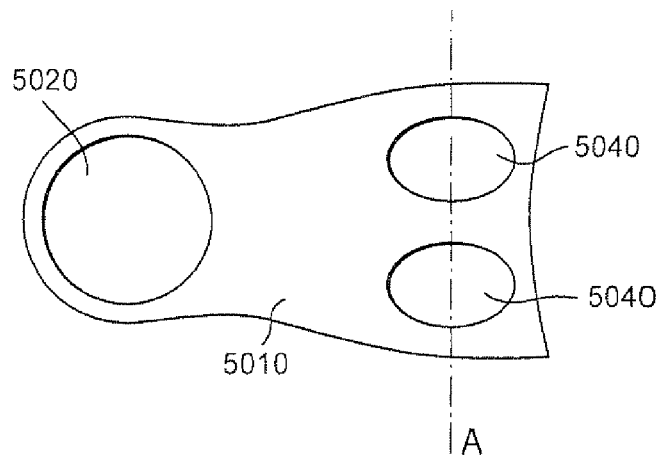

Referring to FIGS. 71 and 72, a patient interface system 5000 comprises a patient interface support structure 5010 that includes a tube connection portion 5020 that is configured to be connected to an air delivery hose, tube or conduit. The patient interface support structure 5010 comprises two openings 5040 that are configured to receive nasal pillows 5030 that are configured to be inserted into, and removable from, the openings 5040. As shown in FIG. 71, each nasal pillow 5030 comprises a bellows 5050. When a flow of breathable gas is introduced into the interface support structure 5010 from a hose, tube or conduit, the pressure created in the patient interface support structure 5010 inflates each pillow 5030 inserted into each of the patient's nares. The pillows 5030 seal against the interior walls of the patient's nares. As the pillows 5030 are removable from the openings of the patient interface support structure 5010, the pillows 5030 may be removed, for example, for cleaning, or for disposal.

The patient interface support structure 5010 may include a support 5070 that is configured to engage the bridge of the patient's nose to support the patient interface system 5000 in sealing engagement with the patient's nares. The support 5070 may be connected to the patient interface support structure 5010 by a connecting member 5060.

4.2 Patient Interface With Inflatable Pillows Second Embodiment

Figure 73:
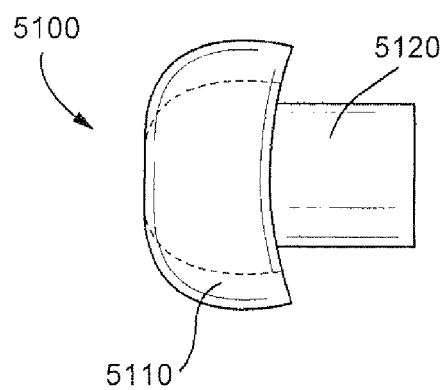
FIG. 73 schematically illustrates a patient interface structure according to another sample embodiment.

Referring to FIG. 73, another sample embodiment of a nasal pillow 5100 usable with the patient interface support structure 5010 comprises a base portion 5110 that is receivable in the opening 5040 of the patient interface support structure 5010 and a sealing portion 5120 that is insertable into the nare of the patient. The sealing portion 5120 may expand from the pressure created in the patient interface support structure 5010 when a flow of breathable gas is introduced therein. The sealing portion 5120 may also include a textured outer surface to improve the sealing against the interior of the patient's nares and/or improve the wearing comfort of the pillows towards the nasal septum.

4.3 Patient Interface With Inflatable Pillows Third Embodiment

Figure 74:
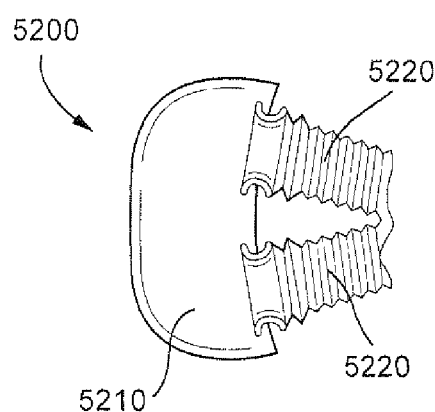
FIG. 74 schematically illustrates a patient interface structure according to another sample embodiment.

Referring to FIG. 74, another sample embodiment of a nasal pillow 5200 usable with the patient interface support structure 5010 comprises a base portion 5210 that is receivable in the opening 5040 of the patient interface support structure 5010. Each pillow 5200 comprises sealing portions 5220 that are insertable into the nare of the patient and that expand from pressure created in the patient interface support structure 5010 when a flow of breathable gas is introduced therein. The sealing portions 5220 may comprise bellows to assist in expanding the sealing portions 5220 upon application of the pressure. The sealing portions 5220 expand and seal against the interior of the patient's nares upon the application of the pressure.

The support 5070 and the connecting member 5060 may be integrally formed with the patient interface support structure 5010, for example as shown in FIG. 71. In another sample embodiment, shown in FIGS. 75 and 76, the support 5070 and the connecting member 5060 may be formed separately. The support 5070 may be, for example, secured to the bridge of the patient's nose by adhesive. The connecting member 5060 may include slots 5090 configured to receive straps configured to hold the patient interface system 5000 in sealing engagement with the patient.

Figure 75:
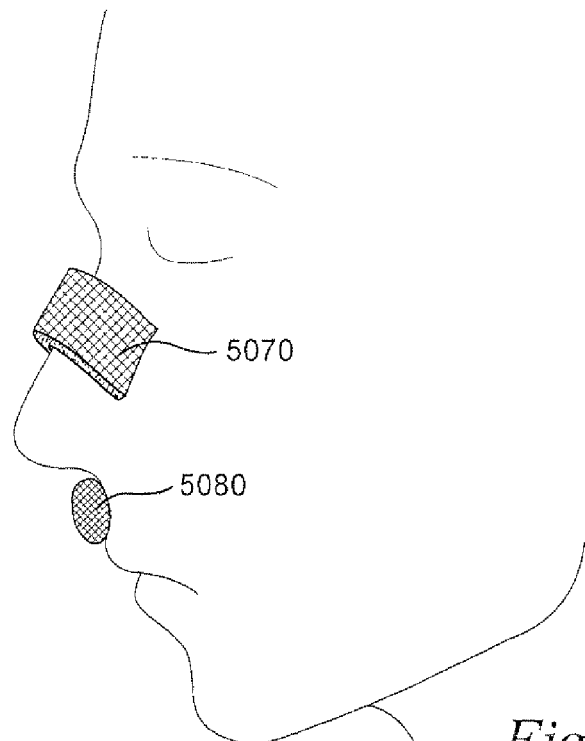
FIG. 75 schematically illustrates a patient interface structure support system according to a sample embodiment.

As shown in FIG. 75, an upper lip support 5080 may also be provided to support the patient interface support structure 5010. The upper lip support 5080 may be, for example, connected to the patient interface support structure 5010 and/or the patient's upper lip by adhesive.

4.4 Patient Interface With Inflatable Pillows Fourth Embodiment

Figure 77:
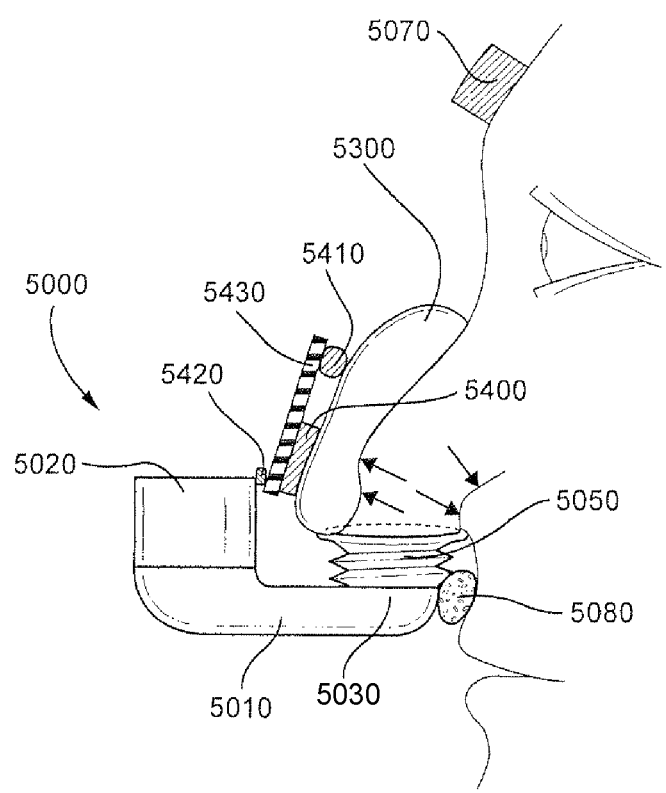
FIG. 77 schematically illustrates a patient interface system according to another sample embodiment.

Referring to FIG. 77, a patient interface system 5000 according to another sample embodiment includes a patient interface support structure 5010 that includes a connection portion 5020 configured to be connected to a hose, tube or conduit that delivers a flow of breathable gas. An upper lip support 5080 may be provided to support the patient interface support structure 5010 against the patient's upper lip. An inflatable membrane 5300 is connected to the patient interface support structure 5010 and is configured to be inflated when pressure is created by a flow of breathable gas into the patient interface support structure 5010. The inflatable membrane 5300 may be formed, for example, of elastic material. The inflatable membrane 5300 is connected to a pair of nasal pillows 5030 that each includes a bellows 5050 that is inflatable upon inflation of the inflatable membrane 5300.

A flexible membrane support 5430 is connected to the flexible membrane 5300 by connectors 5400, 5410. A stop 5420 may be provided to the flexible membrane support 5430 to prevent the flexible membrane 5300 from being overinflated.

Figure 76:
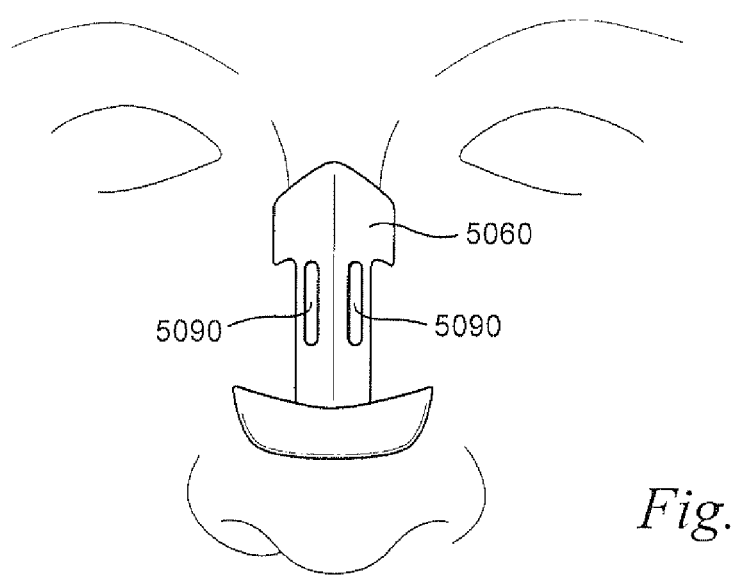
FIG. 76 schematically illustrates a patient interface structure support system according to another sample embodiment.

The patient interface system 5000 may comprise the support 5070 and the support 5070 may be connected to the flexible membrane support 5430 by a connecting member (not shown), such as shown in FIG. 76, for example. The connecting member may comprise slots configured to receive straps for supporting the patient interface system 5000 in sealing engagement with the patient's nares.

The nose may act as a bearing for the inflated membrane 5300. The contact pressure for inflating the membrane 5300 and sealing the pillows 5020 is adjusted by the therapy pressure and not by the mounting system of the patient interface at the patient's head. The inflatable membrane 5300 is mounted to the bellows 5050 which keep the membrane 5300 in position and movements of the remaining patient interface system, e.g. the patient interface support structure, are offset. The combination of the elastic membrane and the bellows 5050 enables freedom of movement of the patient interface support structure 5010, for example movement caused by tube drag, before leakage occurs.

5.0 Leak Guards

Figure 67:
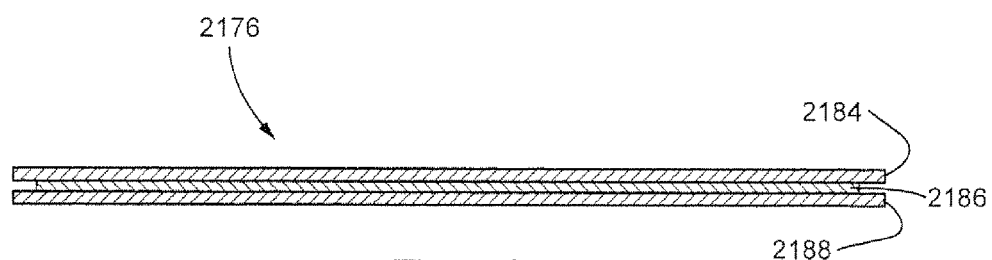

As shown in FIG. 67, the lateral strip 2176 may comprise an outer strip 2184 and an adhesive strip 2188 configured to be adhered to the patient, e.g. across the nasal bridge. A dilation strip 2186 may be provided between the strips 2184, 2188.

Figure 68:
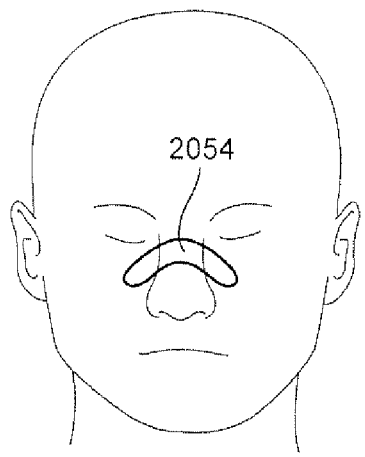
FIGS. 68-70 schematically illustrate leak guards according to various sample embodiments.
Figure 69:
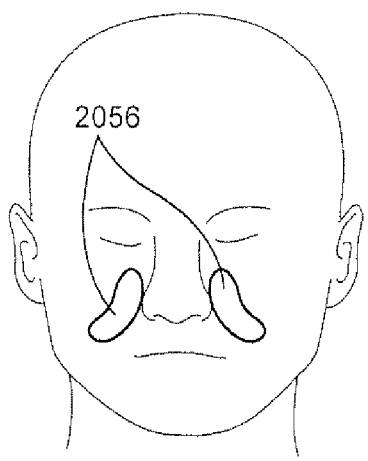
Figure 70:
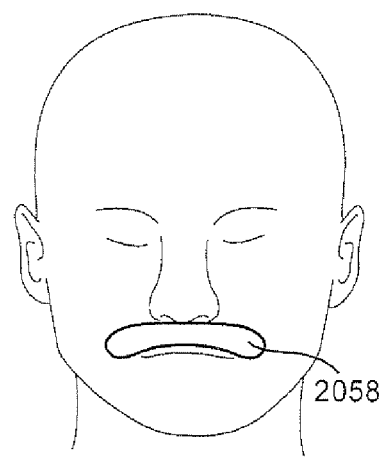

Referring to FIGS. 68-70, leak guards may be provided to the face of the patient 1. As shown in FIG. 68, a leak guard 2054 may be secured across the bridge of the nose of the patient. As shown in FIG. 69, leak guards 2056 may be provided at the creases between the sides of the nose of the patient and the patient's cheeks. As shown in FIG. 70, a leak guard 2058 may be provided across the upper lip of the patient. Such a leak guard 2058 may be used, for example, to eliminate leaks potentially caused by patients with mustaches.

The leak guards shown in FIGS. 68-70 may be foam-backed strips that are adhesively attached to the face of the patient. Alternatively, the leak guards may be mechanically secured to the face of the patient, for example by securement to a cushion or mask.

6.0 Adhesive Properties

In the sample embodiments discussed above, the adhesive can be connected to the interface in such a way that the patient interface structure and adhesive may be simultaneously removed and replaced. The swivel ring can be permanently fixed to the adhesive tape, air delivery tube or patient interface structure. The patient interface structure may be fixed to the adhesive tape.

The adhesive and interface should not leave visible signs of CPAP use following treatment, for example pressure sores or messed up hair. This will increase patient comfort and compliance with treatment. The adhesive also should not leave a residue on the patient's face. However, if a residue does remain, it should be easily removed, for example by a wet cloth or alcohol swab.

The adhesive and interface may be durable. Alternatively, the adhesive and/or interface may be disposable. There may also be an 'end of life' indicator on the adhesive and/or interface to alert the patient to change their adhesive and/or interface or part thereof. This is to improve hygiene and interface function.

The adhesive may be formed in strips that are, for example, generally rectangular. Such strips may be aligned on the patient's face in positions (vectors) that are sufficient to locate or locate and seal the interface to the nares and/or mouth of the patient. Alternatively, the strips may be triangular, circular or any other desired shape. In another form, an adhesive fitting guide may be provided with the interface, for example alignment markings on the adhesive, drawings and descriptions of correctly aligned interfaces.

The adhesive and interface should be able to function with about 2 cm $H_2O$-30 cm$H_2O$ pressure applied from a flow generator. In another form, the adhesive and interface should be able to function with about 4 cm $H_2O$-12 cm $H_2O$ pressure applied from a flow generator. It should be appreciated that these pressures are for use of the interface with a CPAP apparatus, i.e. an apparatus in which the interface sealingly engages the patient's airways. Other pressure ranges may be possible with different apparatus, e.g. an apparatus in which the interface does not sealingly engage the patient's airways.

In one form, the adhesive may have a high tensile strength.

The tensile strength of the adhesive may be related to the size of the adhesive strip. The adhesive may have a higher tensile strength on smaller adhesive strips and may have a lower tensile strength on larger adhesive strips.

The adhesive may also be flexible. This allows the adhesive to conform to multiple areas of the face, for example cheeks and/or nose.

The adhesive may be able to endure the different environmental conditions found across the world, for example, humidity, temperature, and wind chill.

The adhesive may be no more than about 10 mm thick.

Preferably, the adhesive may remain sticky during the patient's sleep, for example, 4 hours, 8 hours, 12 hours.

The adhesive may be biocompatible. In another form, the adhesive may be biodegradable.

The adhesive may be zinc oxide based, synthetic rubber (e.g. hydrocolloid), acrylic, silicone gel, polyurethane, hydrocolloid, etc.

The adhesive may be clear. Alternatively, the adhesive may be neutral or skin toned. Alternatively, the adhesive may be any color. In another form, the color of the adhesive may be used as an 'end of life' indicator, e.g. fade to white when it needs to be disposed of.

The adhesive strips, hook and loop fastener material, and any other material used in the interface system may be transparent, neutral or skin toned to be as unobtrusive as possible. The adhesive strips, hook and loop fastener material or any other material may be colored or patterned to suit various users. For example, pink may be provided for female users.

The adhesive may be covered after use with a non-adhesive strip, or release paper. The adhesive may be covered after multiple uses with the non-adhesive strip. For example, the adhesive may be re-covered at least 5 times without losing integrity. Additionally, the non-adhesive strip may be used to package and store the adhesive for long periods. The adhesive should not deteriorate while in storage.

The adhesive on the strip may not cover the entire surface of the adhesive strip. For example, the adhesive may selectively be applied to the adhesive strip to enable easier peel from the patient's face, better performance of the adhesive strip in shear, and/or to rest certain areas of the patient's skin with repeated use. For example, the adhesive may be applied in horizontal lines across the adhesive strip (when viewed in its in use orientation) so that the strip may perform better in shear and/or be easier to remove from the patient's skin when peeled laterally.

The interface should allow for venting. In another form, the adhesive may allow some/all venting to occur. For example, a vent hole(s) may be provided on the adhesive proximal to the interface to allow the passage of expired air from the patient.

The adhesive strips may have a non-sticky end. The non-sticky end will enable the user to easily remove the adhesive once applied. It also means that should the interface need to be removed quickly; it can be done so simply and intuitively. Alternatively, another form of a safety disconnect feature may be included with the interface, for example perforations between the adhesive and patient interface structure.

The adhesive and interface may be coupled with a chest strap. The chest strap may be releasably connected to the air delivery tube. The purpose of the chest strap is to provide more stability of the interface by preventing the air delivery tube from a wide range of movement. Such chest straps have been disclosed in U.S. Patent Application Publication 2009/0078259 A1, the entire contents of which is incorporated herein by reference.

The adhesive may be able to be sterilized.

The adhesive used to stick the fastener or loop material to the patient's face, e.g. the nose, may be a light switching adhesive. Light switching adhesives are sticky in the dark and when exposed to light, the stickiness deactivates/breaks down such that the strip would come off the nose more easily after exposure to light, for example after the patient wakes up and turns on the light or exposes the adhesive strip to sunlight. This is desirable for sleeping as the patient's bedroom may be dark while the patient sleeps and the strip will be adhered to the nose. When the patient wakes up and opens their curtains or turns on a light, the strip would come off more easily. Such light switching adhesives may be available from Lumina Adhesives of Goteburg, Sweden.

The adhesive may be an adhesive silicone gel. In addition to use on the patient interface structure and/or the connectors, the adhesive silicone gel may be used as an accessory for a masked designed for elderly patients, for example to promote healing of scars caused by ill fitting masks. The adhesive silicone gel may also be used with other components, for example cheek supports and/or forehead supports. The mineral oil used in adhesive silicone gels may also be provided in the patient interface structure and/or connectors and/or the patient interface positioning and stabilizing structure to enhance wound care and promote skin healing. Alternatively, or in addition to, aloe vera may be used in the patient interface structure and/or connectors and/or the patient interface positioning and stabilizing structure.

Adhesive silicone gel as described above is available as Cica-Care™, available from Smith & Nephew. The adhesive silicone gel may be provided, for example, on adhesive strips as described herein. The adhesive silicone gel may soften, flatten and/or fade red, dark and/or raised scars, and relieve itching and discomfort. Cica-Care™ is available as an adhesive silicone contained within a gel sheet. Research suggests that the adhesive silicone in the gel sheet occludes the skin to hydrate a scar area. Moisture is locked into the skin around the scar, reducing the blood supply and deposit of collagen, which is what the body uses to rebuild wounded skin. The adhesive silicone gel acts to make scar tissue paler in color, closer to the patient's natural skin color.

Other adhesives suitable for use with the sample embodiments described herein include zinc oxide adhesive, ultra-thin hydrocolloid (HDx) and Skinz Tape™. Skinz Tape™ may be used for neonatal care and adheres to skin and silicone. Such adhesives may be obtained from Kree Tech International Corporation Inc. of Quebec.

Scapa North America of Windsor, Conn. provides silicone gel adhesive, BioFlex™ adhesives, and acrylic adhesives that may be used with the sample embodiments disclosed herein.

Acrylic, porous, and electrically conductive adhesives, available from Adhesive Research of Glen Rock, Pa., may also be used with sample embodiments disclosed herein. Dissolvable films available from Adhesives Research are also usable with sample embodiments disclosed herein.

The adhesives used with sample embodiments disclosed herein may also be acrylic adhesives and/or synthetic rubber adhesives available from, for example, MACtac of Stow, Ohio, e.g. MACtac TM8410.

Light switching, pressure sensitive acrylic adhesive may also be used with sample embodiments disclosed herein. Such adhesives are available from, for example, Lumina Adhesives of Goteborg, Sweden.

The adhesive strips described above placed over the bridge of the patient's nose may have perforated portions, for example in the regions positioned under the eyes and/or around the nose. The perforated portions may be easily torn off the adhesive strip to allow the patient to customize the shape of the adhesive strip to suit the patient's facial profile.

The adhesive may also be porous such that the adhesive itself is more flexible and conforming and allow the skin underneath the adhesive strip to move more readily. The adhesive may also be breathable. The adhesive may also be coated on a stretchable backing fabric that allows the skin to move more freely. The adhesive and/or the backing fabric may have a warming effect to relieve any jetting sensation from the flow of breathable gas.

The adhesive strip or patch may have an area in the range of 250 mm$^2$ to 300 mm$^2$, preferably 500 mm$^2$ to 2500 mm$^2$, more preferably 1,000 mm$^2$ to 1,500 mm$^2$ It should be appreciated that the patient interface structures disclosed above need not be limited to providing CPAP therapy, but may include any device that is attached to the nose under conditions where pressure on the face or back of the patient's head is not possible or advisable, for example for use with burn victims.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface system for delivering a flow of breathable gas to a patient, comprising:
    a patient interface support structure configured to be connected to a hose that delivers the flow of breathable gas;
    a pair of nasal pillows supported by the patient interface support structure, wherein each nasal pillow is configured to seal against an interior of the patient's nares;
    a support member configured to engage a bridge of the patient's nose; and a connecting member configured to connect the support member and the patient interface support structure, wherein said pair of nasal pillows is selectively repositionable in a plurality of positions relative to the support member while remaining engaged with the patient's nares.

2. A patient interface system according to claim 1, wherein each pillow comprises a bellows.

3. A patient interface system according to claim 1, wherein each pillow comprises a textured outer surface.

4. A patient interface system according to claim 1, wherein each pillow is received in an opening in the patient interface support structure and is removable from the opening.

5. A patient interface system according to claim 1, further comprising an upper lip support configured to support the patient interface support structure against the patient's upper lip.

6. A patient interface system according to claim 1, wherein the connecting member and the patient interface support structure are integrally formed.

7. A patient interface system according to claim 1, wherein the connecting member comprises a pair of slots configured to receive ends of a strap or straps.

8. A patient interface system according to claim 1, further comprising an elastic membrane connected to the pair of nasal pillows, wherein the elastic membrane is configured to be inflated by an increase of pressure in the patient interface support structure from receipt of the flow of breathable gas.

9. A patient interface system according to claim 8, further comprising an elastic membrane support connected to the elastic membrane.

10. A patient interface system according to claim 9, further comprising a stop connected to the elastic membrane support that is configured to limit inflation of the elastic membrane.

11. A patient interface system according to claim 1, wherein the support member is separable from the connecting member.

* * * * *